United States Patent
Iketaki et al.

(10) Patent No.: US 6,667,830 B1
(45) Date of Patent: Dec. 23, 2003

(54) SUPER-RESOLUTION MICROSCOPE SYSTEM AND METHOD FOR ILLUMINATION

(75) Inventors: Yoshinori Iketaki, Tokyo (JP); Masaaki Fujii, Kanagawa (JP); Takashige Omatsu, Kanagawa (JP)

(73) Assignees: Japan Science and Technology Corporation, Saitama (JP); Olympus Optical Co., Ltd., Tokyo (JP)

(*) Notice: Subject to any disclaimer, the term of this patent is extended or adjusted under 35 U.S.C. 154(b) by 0 days.

(21) Appl. No.: 09/445,389

(22) PCT Filed: Apr. 9, 1999

(86) PCT No.: PCT/JP99/01904
§ 371 (c)(1),
(2), (4) Date: Mar. 17, 2000

(87) PCT Pub. No.: WO99/53356
PCT Pub. Date: Oct. 21, 1999

(30) Foreign Application Priority Data

Apr. 9, 1998 (JP) .......................................... 10-097924

(51) Int. Cl.⁷ .............................................. G02B 21/00
(52) U.S. Cl. ................... 359/368; 359/385; 250/458.1; 250/459.1
(58) Field of Search ................... 359/368, 370, 359/385, 386; 250/492.2, 458.1, 459.1, 461.1, 461.2; 430/139, 396; 356/318

(56) References Cited

U.S. PATENT DOCUMENTS 5,245,619 A * 9/1993 Kronberg ...................... 372/32
5,583,342 A * 12/1996 Ichie ........................ 250/459.1
5,866,911 A * 2/1999 Baer ........................ 250/458.1

FOREIGN PATENT DOCUMENTS

| JP | 8-184552 | 7/1996 |
| JP | 10-142151 | 5/1998 |
| JP | 11-95120 | 4/1999 |

OTHER PUBLICATIONS

Yasuo Okuzawa et al., Chemical Physics Letters, "Direct Observation of Second Excited $^{1,3}$ (n,π*) States of Pyrazine by UC–IR Double Resonance Dip Spectroscopy", Aug. 10, 1990, vol. 171, No. 4, pp. 341–346.

Elhahan Sahar et al., IEEE Journal of Quantum Electronics, "Excited Singlet–State Absorption in Dyes and Their Effect on Dye Lasers", DEc. 1977, vol. QE–13, No. 12, pp. 962–967.

* cited by examiner

Primary Examiner—Mark A. Robinson
Assistant Examiner—Lee Fineman
(74) Attorney, Agent, or Firm—Wenderoth, Lind & Ponack, L.L.P.

(57) ABSTRACT

A microscope system comprising an adjusted specimen and a microscope body, wherein the adjusted specimen is dyed with molecule which has three electronic states including at least a ground state and in which an excited wavelength band from the first electron excited state to the second electron excited state overlaps a fluorescent wavelength band upon deexcitation through a fluorescence process from the first electron excited state to a vibrational level in the ground state. There is provided a novel microscope system which is enabled to condense an erase light for exciting a molecule in the first electron excited state to the second electron excited state in an excellent beam profile by using a simple, compact optical system and which has high stability and operability and an excellent super-resolution.

63 Claims, 40 Drawing Sheets

$$I(x,y) = \left| \int_{x'^2+y'^2 \leq a^2} PSF(x-x',y-y')\exp[-i\phi(x',y')]dx'dy' \right|^2$$

$$PSF(x,y) = \frac{2J_1(2\pi\xi)}{2\pi\xi}, \quad \xi = \frac{NA}{\lambda}\sqrt{x^2+y^2}$$

(a)

(b)

Cassegrain (Schwalzschild) Type

Walter Type (a)

(b)

(a) $n=0$ (b) $n=1$

— $\psi(\xi)$
---- $|\psi(\xi)|^2$ (c) $n=2$ (d) $n=3$

US 6,667,830 B1

SUPER-RESOLUTION MICROSCOPE SYSTEM AND METHOD FOR ILLUMINATION

TECHNICAL FIELD

The invention of this application relates to a microscope system. More particularly, the invention of this application relates to a novel microscope system of high performance and function, which is able to achieve a high quality image of a high spatial resolution by illuminating a dyed specimen with lights of plural wavelengths.

BACKGROUND ART

In the prior art, there have been developed various types of optical microscopes, and their performance has been enhanced according to the development in the peripheral technique including the laser technique and the electronic graphic technique. As one of these high performance optical microscopes, there has been proposed (in Japanese Patent Application No. 6-329165) a microscope which is able, by using a double resonance absorption process induced by illuminating a specimen with lights of plural wavelengths, not only to control the contrast of an image to be obtained but also to perform a chemical analysis.

This optical microscope can, by using the double resonance absorption, select a specific molecule and observe absorption and fluorescence caused by a specific optical transition. First, an electron of a valence orbit 2, owned by the molecule in a ground state illustrated in FIG. 1, is excited to a valence orbit 3 that is a vacant orbit by light irradiation, as illustrated in FIG. 2. This is a first excited state. Next, the electron on a valence orbit 1 is excited, as illustrated in FIG. 3, to a hole generated on the valence orbit 2 by irradiating them with a light of another wavelength. This is a second excited state. The molecule then returns to the ground state while emitting fluorescence or phosphorescence, as illustrated in FIG. 4. And, an absorption image or a luminous image is observed by using the absorption process of FIG. 2 or the emission of the fluorescence or phosphorescence of FIG. 4.

At first, when the molecule composing a specimen is to be excited to the first excited state with a light of a resonance wavelength $\lambda1$ by, for example, a laser beam, the number of molecules in the first excited state in a unit volume increases as an intensity of the irradiation light increases. Since a linear absorption coefficient is given as a product of an absorption cross-section per molecule and the number of molecules per unit volume, in the excitation process of FIG. 3, the linear absorption coefficient for the light of a resonance wavelength $\lambda2$ subsequently applied depends upon the intensity of the light of the wavelength $\lambda1$ applied first.

In short, the linear absorption coefficient for the wavelength $\lambda2$ can be controlled with the intensity of the light of the wavelength $\lambda1$. This indicates that, when irradiating a specimen with lights of two wavelengths $\lambda1$ and $\lambda2$ and obtaining a transmission image by the wavelength $\lambda2$, contrast of the transmission image can be completely controlled with a quantity of the light of the wavelength $\lambda1$.

On the other hand, when the deexcitation process from the second excited state of FIG. 3 by fluorescence or phosphorescence is possible, the luminous intensity is proportional to the number of molecules in the first excited state. This makes it possible to control an image contrast, even when used as a fluorescent microscope.

Further, this optical microscope of the prior art is able not only to control the contrast but also to perform the chemical analysis. Since the outermost valence orbit in FIG. 1 has an energy level intrinsic to a molecule, the wavelength $\lambda1$ is different for the molecule. At the same time, the wavelength $\lambda2$ is also intrinsic to the molecule. As a result, the molecule to absorb or emit a light can be restricted from the two wavelengths $\lambda1$ and $\lambda2$, so that an accurate chemical composition of a specimen can be identified.

Moreover, when the valence electron is to be excited, only a light having a specific electric-field vector with respect to a molecular axis is intensively absorbed. Thus, if an absorption image or fluorescence image is obtained while determining the directions of polarization of the wavelengths $\lambda1$ and $\lambda2$, the direction of orientation can also be identified for the same molecule.

In recent years, there has also been proposed (in Japanese Patent Application No. 8-302232) a fluorescent microscope which has a high spatial resolution exceeding a diffraction limit by using the double resonance absorption process.

FIG. 5 is a conceptional diagram illustrating the double resonance absorption process in molecule. It is illustrated in FIG. 5 that a molecule in the ground state is excited to the first excited state with the light of the wavelength $\lambda1$ and further to the second excited state with the light of the wavelength $\lambda2$ and that fluorescence from this second excited state is extremely weak for some kinds of a molecule.

The molecule having such optical properties experiences a remarkably interesting phenomenon. FIG. 6 illustrates an extension of a spatial distance in the double resonance absorption process, with an abscissa being an X axis. In FIG. 6, there are illustrated a spatial area A1 which is irradiated with the light of the wavelength $\lambda2$ and a spatial area A0 which is not irradiated with the light of the wavelength $\lambda2$. In this spatial area A0, a great number of the molecules being in the first excited state are generated by the $\lambda1$ light excitation. At this time, fluorescence emitted with a wavelength $\lambda3$ from the spatial area A0 can be observed. In the spatial area A1, however, the irradiation of the light of the wavelength $\lambda2$ excites most of the molecules in the first excited state instantly to the second excited state at a higher level, so that the molecules in the first excited state disappears. As a result, the fluorescence of the wavelength $\lambda3$ completely disappears, and further, the fluorescence from the second excited state does not exist intrinsically, so that the fluorescence itself is completely inhibited in the spatial area A1. It is therefore understood that the fluorescence exists only in the spatial area A0.

This result has a remarkably important meaning if considered from the field of application of the microscope. In the scannigng type laser microscope of the prior art, a laser beam is condensed to produce a micro beam thereby to scan a specimen to be observed. At this time, the size of the micro beam is determined by the diffraction limit which in turn is determined by a numerical aperture of a condenser lens and a wavelength, so that a higher spatial resolution cannot be expected on principle. However, according to FIG. 6, since the fluorescent area is inhibited with the irradiation of $\lambda2$, by overlaping the wavelengths of two kinds of $\lambda1$ and $\lambda2$ skillfully, the fluorescent area is made narrower than the size determined by the numerical aperture of the condenser lens and the wavelength, while noticing the irradiation area of $\lambda1$ for example. Thus, the spatial resolution is substantially improved. Therefore, by adopting this principle, it is possible to provide a fluorescent microscope exceeding the diffraction limit. This is a super-resolution microscope using the double resonance absorption process.

In order to enhance the super-resolution of this microscope, another proposal has been made (in Japanese Patent Application No. 9-25444). A molecule of various kinds, which has three quantum states including at least the ground state and in which a thermal relaxation process is more dominant than a relaxation process by fluorescence in transition upon deexcitation from a higher excited state excepting the first excited state to the ground state, is employed as a fluorescence labeler molecule. The specimen in which the fluorescence labeler molecule and a biomolecule dyed biochemically are chemically bonded, is irradiated with the light of the wavelength $\lambda 1$ to excite the fluorescence labeler molecule to the first excited state and is then instantly excited with the light of the wavelength $\lambda 2$ to a higher quantum level, so that fluorescence from the second excited state is inhibited, thereby to inhibit the spatial fluorescent area artificially, thus the spatial resolution can be improved.

The optical properties of such molecule can be described in the following manner from the standpoint of quantum chemistry.

Generally, each atom composing a molecule is bonded by a $\sigma$ or $\pi$ bonds. In other word, according to the quantum chemistry, molecular orbits of the molecule has an a molecular orbit or a $\pi$ molecular orbit, and an electron existing on these molecular orbits plays an important role to bond each atom. Of these, the electron on the a molecular orbit intensely bonds each atom to determine an inter-atomic distance in the molecule, which is the frame of the molecule. On the contrary, the electron on the $\pi$ molecular orbit makes little contribution to the bond of each atom, but is rather bound throughout the molecule by an extremely weak force.

In most cases, if the electron on the $\sigma$ molecular orbit is excited with a light, the inter-atomic distance of the molecule is highly changed to cause a drastic structure change including dissociation of the molecule. As a result, a kinetic energy of the atom and an energy given for the structural change by the light to the molecule are mostly transformed into a thermal energy. Because of this, an excitation energy is not consumed in fluorescence. Further, the structural change of the molecule occurs at an extremely high rate, for example in time period smaller than pico seconds, so that the fluorescence lifetime is short even if fluorescence occurs in that process. On the contrary, however, even if the electron on the $\sigma$ molecular orbit is excited, the structure itself of the molecule makes little change, but remains at a high quantum discrete level for a long time so that it is deexcited while releasing fluorescence in the order of nano seconds.

According to the quantum chemistry, the fact that a molecule has a $\pi$ molecular orbit and the fact that a molecule has a double bond are equivalent, and selection of a molecule having sufficient double bonds as a fluorescence labeler molecule is a necessary condition. Moreover, it has been confirmed (e.g., M. Fujii et. al., Chem. Phys. Lett. 171 (1990) 341).that, for a six-membered ring molecule such as a benzene or pyrazine among molecules having double bonds, fluorescence from the second electron excited state is extremely weak. Hence, if a molecule containing the six-membered ring such as the benzene or pyrazine is selected as a fluorescence labeler molecule, the super-resolution of the microscope can be effectively utilized because a fluorescence lifetime from the first excited state is long and because the fluorescence can be easily inhibited by an optical excitation from the first excited state to the second excited state.

Accordingly, if the specimen is dyed with such a fluorescence labeler molecule and is observed, not only its fluorescent image can be observed in a high spatial resolution, but also only the specific chemical group of a bio-specimen can be selectively dyed by adjusting the chemical group of the side chain of the fluorescence labeler molecule. Thus, even the detailed chemical composition of the specimen can be analyzed.

Generally, the double resonance absorption process occurs only when two optical wavelengths, a polarization state and the like satisfy specific conditions, so that the molecular structure can be known in a remarkable detail by using this fact. A polarization plane of a light and an orientation direction of a molecule have an intense correlation, so that the double resonance absorption process intensely occurs when each polarization plane of the lights of two wavelengths and the orientation direction of the molecule make a predetermined angle. Hence, by irradiating a specimen surface simultaneously with the two wavelength lights and by turning each polarization plane, disappearing level of fluorescence is changed, so that the information on a spatial orientation of a tissue to be observed is achieved from that change. This achievement can also be made by adjusting the lights of two wavelengths.

It is understood from the description thus far made that the optical microscope of the prior art using the double resonance absorption process has the super-resolution and the high analyzing ability.

In the super-resolution microscope using this double resonance absorption process, there have also been proposed a fluorescence labeler molecule which is capable of achieving more effective fluorescence inhibitation and a suitable timing of light-irradiation.

FIG. 7 illustrates one example of a timing at which a specimen is irradiated with two kinds of lights of wavelengths $\lambda 1$ and $\lambda 2$. As illustrated in FIG. 7, a pulse light shorter than a lifetime of the first excited state is employed. The life time of the first excited state is a time period for the fluorescence labeler molecule to emit fluorescence. And, the specimen is irradiated at first for a time period t with the light of the wavelength $\lambda 1$ and then with the light of the wavelength $\lambda 2$.

Qualitatively, the irradiation is performed at first for the time period t with the pulse light of the wavelength $\lambda 1$ sufficiently shorter than the lifetime of the fluorescence labeler molecule in the first excited state, thereby to produce a molecule in the first excited state in the observation area. Immediately after this, an area unnecessary for the observation is irradiated with the pulse light of the wavelength $\lambda 2$ sufficiently shorter than the lifetime of the first excited state, thereby to excite the molecule in the first excited state to the second excited state, thus inhibiting fluorescence.

This process can be further quantitatively explained.

Generally, when the molecule in the ground state is to be excited with the light of the wavelength $\lambda 1$ to the first excited state, the excitation process can be described by the following rate equation. Specifically: the number of molecules per unit area of the molecule dyed to a specimen is designated by $N_0$; a photon flux of the light of the wavelength $\lambda 1$ is designated by $I_0$; and the number of molecules in the ground state at a time t after irradiation of the light of the wavelength $\lambda 1$ is designated by N. Moreover, the lifetime of the first excited state is designated by $\tau$, and an absorption cross-section upon transition from the ground state to the first excited state by the light of the wavelength $\lambda 1$ is designated by a $\sigma_{01}$. Then, the rate equation is expressed in the following form:

$$\frac{dN}{dt} = N_0 I_0 \sigma_{01} \frac{(N_0 - N)}{\tau} \quad \text{Equation 1}$$

If this equation is concretely solved, it is possible to determine the number of molecules n in the first excited state per unit volume at the time t after the light irradiation. That is.

$$n = \frac{N_0 I_0 \sigma_{01} \tau}{(1 + I_0 \sigma_{01} \tau)} \cdot \left[1 - e^{[-(I_0 \sigma_{01} + \frac{1}{\tau})t]}\right] \quad \text{Equation 2}$$

wherein $n = N_0 - N$ This Eq. 2 can be transformed into Eq. 4 by irradiation with the light of the wavelength $\lambda 1$ in such a small quantity as to satisfy the following Eq. 3:

According to Eq. 3, the value n is substantially proportional to the irradiation time t if the irradiation time of the light of the wavelength $\lambda 1$ is shorter than the lifetime of the molecule in the first excited state and if the photon flux of the light of the wavelength $\lambda 1$ is small.

Next, will be considered the case in which the molecule in the first excited state upon irradiation with the light of the wavelength $\lambda 2$ for a time period T immediately after irradiation of the light of the wavelength $\lambda 1$ is to be excited to the second excited state.

The photon flux of the light of the wavelength $\lambda 2$ is designated by $I_1$; the number of molecules in the first excited state at the time (T+t) after irradiation with the light of the wavelength $\lambda 1$ is designated by n; and an absorption cross-section upon transition from the first excited state to the second excited state by the light of the wavelength $\lambda 2$ is designated by $\sigma_{12}$. Then, the rate equation on n is expressed in the following form:

$$\frac{dN}{dt} = -\sigma_{12} I_1 n - \frac{n}{\tau} \quad \text{Equation 5}$$

By solving this equation, the value n can be concretely determined as in the following equation when the irradiation with the light of the wavelength $\lambda 1$ is made for the time period t and is interrupted and when the irradiation with the light of the wavelength $\lambda 2$ is made immediately after the former irradiation:

$$n = (I_0 \sigma_{01} N_0 t) \cdot e^{-(\sigma_{12} I_1 + 1/\tau)T} \quad \text{Equation 6}$$

According to this Eq. 6, on the other hand, the value n is expressed for $I_1 = 0$ with no irradiation of the light of the wavelength $\lambda 2$:

$$n = (I_0 \sigma_{01} N_0 t) \cdot e^{T/\tau} \quad \text{Equation 7}$$

As a matter of fact, Eq. 6 indicates the number of molecules in the first excited state per unit volume in the area where the fluorescence is inhibited, and Eq. 7 indicates the number of molecules in the first excited state per unit volume in the area where the fluorescence is not inhibited. For a fluorescence yield $\Phi$ of the molecule, the fluorescent intensity F1 from the fluorescence inhibited area and the fluorescent intensity F2 from the fluorescence not-inhibited area are given by the following Equations 8 and 9, respectively:

$$F_1 = \Phi(I_0 \sigma_{01} N_0 t) \cdot e^{-(\sigma_{12} I_1 + 1/\tau)T} \quad \text{Equation 8}$$

$$F_2 = \Phi(I_0 \sigma_{01} N_0 t) \cdot e^{T\tau/} \quad \text{Equation 9}$$

A fluorescence inhibition ratio (=F1/F2) is determined to Eq. 10 from Eqs. 8 and 9:

$$F_1/F_2 = e^{-\sigma_{12} I_1 T} \quad \text{Equation 10}$$

Consequently, if the irradiation with the two kinds of lights of $\lambda 1$ and $\lambda 2$ is made at the timings illustrated in FIG. 7, it is possible to inhibit, at the ratio of Eq. 10, the fluorescence from the area not needed to be observed. According to Eq. 10, the fluorescence can be inhibited at an arbitrary ratio by adjusting the values $I_1$ and T under the condition of $T < \tau$.

FIG. 8 illustrates the timing for measuring a fluorescence intensity to be emitted from the observation area. Basically, the measuring timing of the fluorescent intensity is that the fluorescence intensity emitted from the observation area is measured for an ample time after the end of the irradiation with the light of the wavelength $\lambda 2$. At this measuring timing, the fluorescence from the observation area can be measured at an excellent S/N ratio with little fluorescence from the inhibited area.

FIGS. 9 and 10 exemplify the irradiation timing of the specimen with the two kinds of lights of the wavelengths $\lambda 1$ and $\lambda 2$ and the measuring timing of the fluorescent intensity from the observation area, respectively. Also with these timings illustrated in FIGS. 9 and 10, it is possible to realize the super-resolution microscope effectively.

In any of these timings of FIGS. 8 to 10, however, the time periods t and T have to be shorter than the time period $\tau$ (t, $T < \tau$). This is because if t, $T > \tau$ on the contrary, the molecule in the first excited state is deexcited to the ground state during the irradiations with the two kinds of lights $\lambda 1$ and $\lambda 2$, thereby making the fluorescence itself from the observation area disappear. For t, $T \geq \tau$, the irradiations of the two kinds of lights $\lambda 1$ and $\lambda 2$ could be made simultaneously, as illustrated in FIG. 11, and the intensity of the fluorescence emitted from the observation area could be simultaneously measured. In this case, however, the two kinds of excited intense lights $\lambda 1$ and $\lambda 2$ might move into the detector during the fluorescence measurement.

It is, therefore, desired that the specimen is irradiated under the condition of t, $T < \tau$ with the two kinds of lights $\lambda 1$ and $\lambda 2$ at the timings illustrated in FIGS. 8 to 10. Although the S/N ratio is more or less degraded, the irradiations of the light $\lambda 1$ and $\lambda 2$ may also be effected at absolutely the same timing.

When the specimen is irradiated with the two kinds of lights $\lambda 1$ and $\lambda 2$ under the aforementioned conditions and at the aforementioned timings, it is necessary to measure the fluorescence emitted from the observation area immediately after the end of the irradiation by means of a detector. At that time, there are required to prepare gate signals by a commercially available general-purpose logic circuit and fetch the output electric signals of the detector in the memory of a personal computer.

Basically, as illustrated in the time charts of FIGS. 7 to 10, it raises the effect with fact that the fluorescent lifetime of the molecules to be dyed is longer than the pulse width. In the commercially available general-purpose logic circuit, however, since the switching rate is about 1 nsec, the time period $\tau$ itself is desired to exceed 1 nsecs. In other words, unless the fluorescent lifetime exceeds 1 nsec, the fluorescent phenomenon from the observation area ends before the detector and the measurement circuit become active, so that the measurements cannot be made. Thus, the fluorescence labeler molecule to dye the specimen is required to have a fluorescent lifetime exceeding 1 nsec.

On the other hand, noting the effective fluorescent area from which the signals are to be extracted, it is surely desirable that the fluorescent intensity is weaker in the fluorescence inhibition area, but it is desired from the view point of the improvement in the S/N ratio that the emission intensity of the effective fluorescence area is stronger. In short, the fluorescent intensity is measured from the time when the number of molecules in the first excited state just after the excitation with the light $\lambda 1$ is sufficient. According to the foregoing Eq. 9, the number of excited molecules is attenuated in the manner of an exponential function by the time constant which is determined by the excitation lifetime. Here, according to the characteristics of the exponential function, if the pulse widths t and T of the light are sufficiently shorter than the lifetime $\tau$ of the molecule in the first excited state, it is possible to measure fluorescence of a sufficiently strong intensity, i.e., an effective signal intensity from the molecule in the first excited state just after the excitation with the light $\lambda 1$. Especially if the time periods t and T are about one tenth of the lifetime of the molecule in the first excited state, the number of molecules in the first excited state is as many as 90% of the molecule number just after the excitation with the light $\lambda 1$, so that a sufficient signal intensity from the effective fluorescent area is achieved.

The optical microscope of the prior art thus far described has outstanding usefulness and technical priority in its super-resolution and analytical ability.

However, the optical microscope of the prior art needs the light of the wavelength $\lambda 2$ having an intensity sufficient for inhibiting the fluorescence from the first excited state by exciting a molecule from the first excited state to the second excited state (hereinafter, this light will be called the "erase light" and the light of the wavelength $\lambda 1$ to excite a molecule from the ground state to the first excited state will be called the "pump light"). Although the erase light has a slightly lower intensity than a high-intensity laser beam of several TW/cm2 in the laser scanning type fluorescence microscope using an unresonance two-photon absorption process, it still has a considerably strong intensity, so that it has raised a problem of influences on the bio-specimen.

This high-intensity laser is excessively strong against the biological cells of a specimen. Especially in case where a measurement for a long time is required, influence by heat reserve or absorption of multiple photons in the sample is very serious. Thus, such influence has to be minimized.

Moreover, wavelengths of the pump light and the erase light have to fall outside of the absorption band of the biological cells.

Furthermore, in order to realize a resolution as theoretically estimated, a beam of the erase light condensed on a specimen surface is required to have a zero intensity distribution where an intensity at its central portion is zero and to have an axially symmetric shape (hereinafter, this beam will be called the "hollow beam"). This is because disturbance in the intensity distribution leads as it is to deterioration in the resolution of the microscope.

A laser is frequently used as a light source for the erase light, and in order to achieve a theoretical beam as mentioned above, it is a major premise that the laser must have a satisfactory beam profile, meaning that the beam having an intensity distribution symmetric with respect to an optical axis is desirable.

For example, a dye laser, as used as a light source in the prior art, has a beam shape which is close to triangle and an intensity distribution which is not uniform. As a result, the beam shape condensed on the specimen surface is not the expected hollow beam, but a deformed beam pattern, thereby causing deterioration in the resolution or reduction in the image quality of a microscope image. In addition, there has been proposed that the reduced image by a minute zonal aperture is used as the hollow beam. If this zonal aperture is utilized, however, it is difficult to make an optical alignment or to adjust the focal point. It thus takes a seriously long time to obtain a satisfactory image and needs a skillful technique.

Accordingly, in order to achieve the function of the super-resolution microscope sufficiently, an optical technique for solving those problems has been required.

Further, from the practical aspect, an excellent operability is also an important factor.

The microscope technique of the prior art can be applied to a number of fluorescence labeler molecules by synchronizing the light of the light source with the resonance wavelength of the pump light or the erase light of the fluorescence labeler molecule by means of a dye laser or an optical parametric oscillator (OPO).

However, in the dye laser there are problems such as a reduction in the quantity of light due to a deterioration in the dye and a frequent, troublesome dye exchange. The OPO is convenient but remarkably expensive. Moreover, the OPO is an extremely precise optical system requiring strict managements of humidity and temperature, and a nonlinear optical crystal used has a short lifetime and a high price, thereby making it a light source requiring a serious burden of maintenance and management on the user.

It is, therefore, preferable that a light source to be used has a fixed wavelength, a simple construction and a reasonable price.

In recent years, there has been developed a micro manipulation technique which can capture and move minute particles under observation of the microscope by using a laser beam. It has been earnestly desired to realize the microscope system which is enabled to have high operability and function by adding the function of the micro manipulation technique to the super-resolution microscope.

According to this micro manipulation technique, polarization is produced by condensing a high-intensity laser light to a dielectric particle such as a polyethylene particle, and then the particle can be captured and moved by attracting the particle to an area having the strongest electric field. In this technique, it is preferable to irradiate a particle with a laser beam in directions as various as possible in order to stably capture a specific particle.

However, for these laser beam irradiations in the various directions, many laser light sources and complex mirror optical systems are required, thereby making the move operation extremely difficult although the capture in one space is possible.

On the other hand, by the irradiation with the laser condensed beam of 100 MW/cm$^2$ or more in one direction, the specific particle can be captured in one space and can be spatially moved with scanning of the beam. Nevertheless, the specimen is continuously exposed to the laser beam of a high intensity so that it is seriously damaged. This raises problems that biological cells are photosensitively killed and that a chemical change occurs due to a dissociation or photo-chemical reaction of the molecule themselves.

The invention of this application has been provided in view of the background thus far described and has an object to provide a novel microscope system which has a capability to condense an erase light for exciting a molecule in the first excited state to the second excited state with an excellent beam profile by using a simple, compact optical system and also has a high stability and operability and an excellent super-resolution. Also provided is a novel microscope system which has a micro manipulator function to capture and move specimen particles by using the erase light of a hollow beam without damaging the specimen.

OBJECTS OF THE INVENTION

In order to solve the above-especified problems, the invention of this application provides a microscope system.

According to an aspect of the present invention, a microscope system is provided which comprises an adjusted specimen and a microscope body, wherein the adjusted specimen is dyed with a molecule which has three electron states including at least a ground state and in which an excited wavelength band from the first electron excited state to the second electron excited state overlaps a fluorescent wavelength band upon deexcitation through a fluorescence process from the first electron excited state to a vibrational level in the ground state, wherein the microscope body includes: a light source for a light of a wavelength $\lambda 1$ for exciting the molecule from the ground state to the first electron excited state; a light source for a light of a wavelength $\lambda 2$ for exciting the molecule in the first electron excited state to the second or higher electron excited state; a condensing optical system for condensing the light of the wavelength $\lambda 1$ and the light of the wavelength $\lambda 2$ on the adjusted specimen; overlap means for partially overlapping the irradiation region of the light of the wavelength $\lambda 1$ and the irradiation region of the light of the wavelength $\lambda 2$ on the adjusted specimen; and an emission detector for detecting an emission upon deexcitation of the excited molecule to the ground state, and wherein a region of the emission upon deexcitation of the molecule from the first electron excited state to the ground state is inhibited by irradiating the light of the wavelength $\lambda 1$ and the light of the wavelength $\lambda 2$ through the overlap means.

According to another aspect of the present invention, a microscope system is provided which comprises an adjusted specimen and a microscope body, wherein the adjusted specimen is dyed with a molecule which has three electronic states including at least a ground state, wherein the microscope body includes: a light source for a light of a wavelength $\lambda 1$ for exciting the molecule from the ground state to the first electron excited state; a light source for a light of a wavelength $\lambda 2$ for exciting the molecule in the first electron excited state to the second or higher electron excited state; a condensing optical system for condensing the light of the wavelength $\lambda 1$ and the light of the wavelength $\lambda 2$ on the adjusted specimen; overlap means for partially overlapping the irradiation region of the light of the wavelength $\lambda 1$ and the irradiation region of the light of the wavelength $\lambda 2$ on the adjusted specimen; and an emission detector for detecting an emission upon deexcitation of the excited molecule to the ground state, wherein a region of the emission upon deexcitation of the molecule from the first electron excited state to the ground state is inhibited by irradiating the light: of the wavelength $\lambda 1$ and the light of the wavelength $\lambda 2$ through the overlap means, and wherein a beam obtained by condensing the light of the wavelength $\lambda 2$ has a phase distribution in which the phase is shifted by $\pi$ at a symmetric position with respect to an optical axis of the beam in a plane normal to the optical axis.

According to yet another aspect of the present invention, a microscope system is provided which comprises an adjusted specimen and a microscope body, wherein the adjusted specimen is dyed with a molecule which has three electron states including at least a ground state and in which an excited wavelength band from the first electron excited state to the second electron excited state overlaps a fluorescent wavelength band upon deexcitation through a fluorescence process from the first electron excited state to a vibrational level in the ground state, wherein the microscope body includes: a light source for a light of a wavelength $\lambda 1$ for exciting the molecule from the ground state to the first electron excited state; a light source for a light of a wavelength $\lambda 2$ for exciting the molecule in the first electron excited state to the second or higher electron excited state; a condensing optical system for condensing the light of the wavelength $\lambda 1$ and the light of the wavelength $\lambda 2$ on the adjusted specimen; overlap means for partially overlapping the irradiation region of the light of the wavelength $\lambda 1$ and the irradiation region of the light of the wavelength $\lambda 2$ on the adjusted specimen; and an emission detector for detecting an emission upon deexcitation of the excited molecule to the ground state, wherein a region of the emission upon deexcitation of the molecule from the first electron excited state to the ground state is inhibited by irradiating the light of the wavelength $\lambda 1$ and the light of the wavelength $\lambda 2$ through the overlap means, and wherein a beam obtained by condensing the light of the wavelength $\lambda 2$ has a phase distribution in which the phase is shifted by $\pi$ at a symmetric position with respect to an optical axis of the beam in a plane normal to the optical axis.

In the aforementioned microscope systems, according to the invention of this application:
- the excitation wavelength band from the first electron excited state to the second electron excited state and the excitation wavelength band from the ground state to the first electron excited state are different;
- the molecule is a molecule containing one or more of a six-membered ring;
- the six-membered ring is a benzene ring or a purine base;
- the molecule is a molecule containing one or more of a six-membered ring derivative;
- the six-membered ring derivative is a benzene derivative or a purine derivative;
- the molecule is any of a xanthene group molecule, a rhodamine group molecule, a oxazine group molecule, a cyanine group molecule, a coumarin group molecule, a oxazole group molecule, a oxadiazole group molecule and a stilbene group molecule;
- the molecule is any of the following molecules: 2,2"-dimethyl-p-terphenyl; p-terphenyl (PTP); 3,3',2", 3'''-tetramethyl-p-quaterphenyl; 2,2'"-demethyl-p-quaterphenyl; 2-methyl-5-t-butyl-p-quaterphenyl; 2-(4-biphenylyl)-5-(4-t-butylphenyl)-1,3,4-oxiazole (BPBD-365); 2-(4-biphenylyl)-phenyl- 1,3,4-oxadiazole; 2,5,2"",5""-tetrametyl-p-quinquephenyl3,5,3"",5""-tetra-t-butyl-p-quinquephenyl; 2,5-diphenyloxazole; 2.5-diphenylfuran; PQP (p-quanterphenyl); 2,5-bis-(4-biphenylyl)-1,3,4-oxadiazole; p-quaterphenyl-4,4'''-disulfonic acid disodium salt; p-quaterphenyl-4,4'''-disulfonic acid dipotassium salt; 4,4'''-bis-(2-butyloctyloxy)-p-quaterphenyl; 3,5,3"",5""-tetra-butyl-p-sexiphenyl; 2-(1-naphthyl)-5-phenyloxazole; 2-(4-biphenylyl)-6-phenylbenzoxazotetrasulfonic acid potassium salt; 2-(4-biphenylyl)-6-phenylbenzoxazole-1,3; 4,4'-diphenylstilbene; [1,1'-biphenyl]-4-sulfonic acid, 4,4",-1,2-ethene-diylbis-,dipotassium salt; 2,5-bis-(4-biphenylyl)-oxazole; 2,2'-([1,1'-biphenyl]-4,4'-diyldi-2,1-ethenediyl)-bis-benzenesulfonic acid disodium salt; 7-amino-4-methylcarbostyryl; 1,4-di[2-(5-phenyloxazole)]benzene; 7-hydroxy-4-methylcoumarin; p-bis(o-methylstylryl)-benzene; benzofuran, 2,2'-[1,1'-biphenyl]-4,4'-diyl-bistetrasulfonic-acid; 7-dimethylamino-4-methylquinolom-2; 7-amino-4-methylcoumarin; 2-(p- dimethylaminostyryl)-pyridylmethyl iodide; 7-diethylamonocoumarin; 7-diethylamino-4-methylcoumarin; 2,3,5,6-1H,4H-tetrahydro-8-methylquinolizino-[9,9a,1-gh]-coumarin; 7-diethylamino-4-trifluoromethylcoumarin; 7-dimethylamino-4trifluoromethylcoumarin; 7-amino-4-trifluoromethylcoumarin; 2,3,5,6-1H,4H-tetrahydroquinolizino-[9,9a,1-gh]-coumarin; 7-ethylamino-6-methyl-4-trifluoromethylcoumarin; 7-ethylamino-4-trifluoromethylcoumarin; 2,3,5,6-1H,4H-tetrahydro-9-carboethoxyquinolizino-[9,9a,1-gh]coumarin; 2,3,5,6-1H,4H-tetrahydro-9-(3-pyridyl)-quinolizino-[9,9a,1-gh]coumarin; 3-(2'-N-methylbenzimidazolyl)-7-N,N-diethylaminocoumarin; 2,3,5,6-1H,4H-tetrahydro-9-acetylquinolizino-[9,9a,1-gh]coumarin; N-methyl-4-frifluoromethylpiperidino-[3,2-g]-coumarin; 2-(p-dimethylaminostyryl)-benzothiazolylethyliodide; 3-(2'-benzimidazolyl)-7-N,N-diethylaminocoumarin; brillantsulfaflavin; 3-(2'-benzothiazolyl)-7diethyllaminocoumarin; 2,3,5,6-1H, 4H-tetrahydro-8trifluoromethylquinolizino-[9,9a,1-gh]coumarin; 3,3'-diethyloxacarbocyanine iodide; 3,3'-dimethyl-9-ethylthiacarbocyanine iodide; disodium fluorescein (Uranin); 9-(o-carboxyphenyl)-2,7-dichloro-6-hydroxy-3H-xanthen-3-on2,7-dichlorofluorescien (Fluorescein 548); Fluorol 555 (Fluorol 7GA); o-(6-amino-3-imino-3H-xanthen-9-yl)-benzonic acid (Rhodamine 560); benzoic acid, 2-[ethylamino)-3-(ethylimino)-2,7-dimethyl-3H-xanthen-9-yl],perchlorate (Rhodamine 575); benzoic acid, 2-[ethylamino)-3-(ethylimino)-2,7-dimethyl-3X-xanthen-9-yl],ethyl ester, monohydrochloride (Rhodamine 590); 1,3'-diethyl-4,2'-quinolyloxacarbocyanine iodide; 1,1'-diethyl-2,2'-carbocyanine iodide; 2-[6-(diethylamino)-3-(ethylamino)-3H-xanthen-9-yl] benzonic acid (Rhodamine 610); ethanaminium,N-[(6-diethylamino)-9-(2,4-disulfophenyl)-3H-xanthen-3ylidene]-N-ethylhydroxide, inner salt, sodium salt; Malachit Green; 3,3'-diethylthiacarbocyanine iodide; 1,3'-diethyl-4,2'-quinolyloxacarbocyanine iodide; 8-(2-carboxyphenyl)2,3,5,6,11,12,14,15-octahydro-1H,4H, 10H,13H-diquinolizino[9,9a,1-bc:9',9a,1-hi]xantylium perchlorate (Rhodamine 640); 4-dicyanmethylene-2-methyl-6-(p-dimethylaminostyryl)-4H-pyran; 3,3'diethyloxadicarbocyanine iodide; 8-(2,4-disulfophenyl)-2,3,5,6,11,12,14,15-octahydro-1H,4H, 10H,13H-diquinolizino[9,9a, 1-bc:9', 1-hi]xanthene (Sulforhodamine 640); 5,9-diaminobenzo[a] phenoxazonium percrorate; 9-diethylamino-5H-benzo [a]phenoxazine-5-one; 5-amino-9diethylimino[a] phenoxanium perchlorate; 3-ethylamino-7-ethylimino-2,8-dimethylphenoxazine-5-ium perchlorate; 8-(trifluoromethyl)-2,3,5,6,11,12,14,15-octahydro-1H, 4H,10H,13H-diquinolizino[9,9a,1-bc:9',9a,1-hi] perchlorate; 1-ethyl-2-(4-(p-dimethylaminophenyl)-1, 3-butadienyl)-pyridinium percholorate; Carbazine 122; 9-ethylamino-5-ethylimino-10-methyl-5H-benzo(a) phenoxazonium perchlorate; 3-diethylamino-7-diethyliminophenoxazonium perchlorate; 3-diethylthiatricarbocyanine iodide; Oxazine 750; 1-ethyl-4-(4-(p-dimethylaminophenyl)-1,3-butadienyl)-pyridinium perchlorate; 1,1',3,3,3',3'-hexamethylindodicarcyanine iodide; 1,1'-diethyl-4,4'-carbocyanine iodide; 2-(4-(p-dimethylaminophenyl)-1, 3-butadienyl)-1,3,3-trimethyl-3H-indolium perchlorate; 2-(4-(p-dimethylaminophenyl)-1,3-butadienyl)-3-ethylbenzothoazolium perchlorate; 1,1'-diethyl-2,2'-dicarbocyanine iodide; 1-ethyl-4-(4-(9-(2, 3,6,7-tetrahydro 1H,5H-benzo(ij)-chinolinozinium))-1, 3-butadienyl)-pyridinium perchlorate; 3,3'-dimethyloxatricarbocyanine iodide; 1-ethyl-4-(4-(p-dimethylaminophenyl)-1,3-butadienyl)-quinolinium perchlorate; 8-cyano2,3,5,6,11,12,14,15-octahydro-1H,4H,10H,13H-diquinolizino[9,9a1-bc:9a', 1-hi] xanthylium perchlorate (Rhodamine 800); 2-(6-(4direthylaminophenyl)-2,4-neopentylene-1,3,5)-3-methylbenzothiazolium perchlorate; 1,1',3,3,3',3'-hexamethylindotricarbocyanine iodide; IR125; 3,3'-diethylthiatricarbocyanine iodide; IR144; 2-(6-(9-(2,3, 6,7-tetrahydro-1H,5H-benzo(i,j)-chinolinozinium))-2, 4-neopentylene-1,3,5-hexatrienyl)-3-methylbenzothiazolium perchlorate; 3,3'-diethyl-9,11-neopentylenethiatricarbocyanine iodide; 1,1',3,3,3'-hexamethyl-4,4',5,5'-dibenzo-2,2'-indotricarbocyanine iodide; 3,3'-diethyl-4,4',5,5'-dibenzothiatricarbocyanine iodide; 1,2'-diethyl-4,4'-dicarbocyanine iodide; IR140; 2-(8-(4-p-dimethylaminophenyl)-2,4-neopentylene-1,3,5, 7octatetraenyl)-3-methylbenzothiazolium perchlorate; IR 132; 2-(8-(9-(2,3,6,7-tetrahydro-1H,5H,benzo(ij) chinolinozinium))-2,4-neopentylene-1,3,5,7-octatetraenyl)-3-methylbenzothiazolium perchlorate; IR26; and IR5;

an optical axis of a beam obtained by condensing the light of the wavelength λ1 and the optical axis of the beam obtained by condensing the light of the wavelength λ2 are coaxial;

the beam obtained by condensing the light of the wavelength λ2 has a phase distribution in which the phase changes continuously from 0 to 2π when turned once around the optical axis in a plane normal to the optical axis;

the beam obtained by condensing the light of the wavelength λ2 has a phase distribution in which the phase changes discontinuously from 0 to 2π when turned once around the optical axis in a plane normal to the optical axis;

the beam obtained by condensing the light of the wavelength λ2 is a Bessel beam;

the Bessel beam is a 1-st-order-Bessel-beam;

the beam obtained by condensing the light of the wavelength λ2 is a laser beam having a vibrational mode of any of the Gauss's type, Laguerre's type and Hermitian's type;

any of a gas laser, a solid laser and a semiconductor laser is provided as the light source for the light of the wavelength λ1;

an oscillation wavelength of any of the gas laser, the solid laser and the semiconductor laser is the wavelength λ1;

a harmonic-wave of an oscillation wavelength of any of the gas laser, the solid laser and the semiconductor laser has the wavelength λ1;

a sum frequency of or a difference frequency between an oscillation wavelength of any of the gas laser, the solid laser and the semiconductor laser and a harmonic-wave of the oscillation wavelength has the wavelength λ1;

any of a gas laser, a solid laser and a semiconductor laser is provided as the light source for the light of the wavelength λ2;

an oscillation wavelength of any of the gas laser, the solid laser and the semiconductor laser is the wavelength λ2;

a harmonic-wave of an oscillation wavelength of any of the gas laser, the solid laser and the semiconductor laser has the wavelength λ2;

a sum frequency of or a difference frequency between an oscillation wavelength of any of the gas laser, the solid laser and the semiconductor laser and a harmonic-wave of the oscillation wavelength has the wavelength λ2;

the gas laser is any of an excimer laser, a copper vapor laser, an argon laser, a He—Ne laser, a $CO_2$ laser, a He—Cd laser and a-nitrogen laser;

the gas laser is of a mode-locked type;

the solid laser is any of a Nd:YAG laser, a Ti sapphire laser, a YLF laser and a ruby laser;

the solid laser is of a semiconductor-laser-excited type;

the solid laser is of a mode-locked type;

the microscope body has one or more of nonlinear media or wavelength modulating element for converting the wavelength of a laser beam from the gas laser, the solid laser or the semiconductor laser;

the nonlinear media or the wavelength modulating element is a nonlinear crystal;

the nonlinear media or the wavelength modulating element is a Raman shifter;

the light of the wavelength λ1 is prepared by modulating a wavelength of a fundamental-wave of the gas laser or the solid laser with the nonlinear media or the wavelength modulating element;

the light of the wavelength λ1 is prepared by modulating a wavelength of a harmonic-wave of the gas laser or the solid laser with the nonlinear media or the wavelength modulating element;

the light of the wavelengthλ2 is prepared by modulating a wavelength of a fundamental-wave of the gas laser or the solid laser with the nonlinear media or the wavelength modulating element;

the light of the wavelength λ2 is prepared by modulating a wavelength of a harmonic-wave of the gas laser or the solid laser with the nonlinear media or the wavelength modulating element;

the condensing optical system for the light of the wavelength λ2 has a phase plate having a refractive-index distribution or an optical-path-difference distribution which gives, to a beam obtained by condensing the light of the wavelength of the λ2, a phase difference distribution in a plane normal to an optical axis of the beam;

the condensing optical system for the light of the wavelength λ2 has a zonal optical system;

the condensing optical system for the light of the wavelength λ2 has a diffractive optical system;

the condensing optical system for the light of the wavelength λ2 has an axicon;

in a resonator of the gas laser, the solid laser or the semiconductor laser, there is provided at least one of a ring-shaped zonal mirror, a zonal diffraction grating, a Fresnel zone plate, a zonal aperture, and a phase plate which gives a phase difference in which electric fields axially symmetric in a plane normal to the optical axis are shifted by x from each other;

the microscope body has an emission condensing optical system for condensing an emission from the molecule to the emission detector;

the emission condensing optical system has a sharp cut filter;

the emission condensing optical system has a notch filter;

the emission condensing optical system has a band-pass filter;

the band-pass filter transmits the emission from the molecule while not transmitting the light of the wavelength λ1 and the light of the wavelength λ2;

the adjusted specimen is sealed by seal means made of a substance transmitting the light of the wavelength λ1 and the light of the wavelength λ2;

the adjusted specimen is covered with cover means made of a substance transmitting the light of the wavelength λ1 and the light of the wavelength λ2;

said substance is synthetic quartz $SiO_2$, $CaF_2$, NaF, $Na_3AlF_6$, LiF, $MgF_2$, $SiO_2$, $LaF_3$, $NdF_3$, $Al_2O_3$, $CeF_3$, $PbF_2$, MgO, $ThO_2$, $SnO_2$, $La_2O_3$ or SiO;

the microscope body has a continuous-wave laser separately of the light sources for the light of the wavelength λ1 and the light of the wavelength λ2, and wherein a beam obtained by condensing the continuous-wave laser on the adjusted specimen has a phase distribution in which the phase is shifted by π at a position symmetric with respect to an optical axis of the beam in a plane normal to the optical axis; and the microscope body has means for relatively scanning, on the adjusted specimen, with a beam obtained by condensing the continuous-wave laser on the adjusted specimen, independently of the beam obtained by condensing the light of the wavelength λ1 and the beam obtained by condensing the light of the wavelength λ2.

Figure 1:
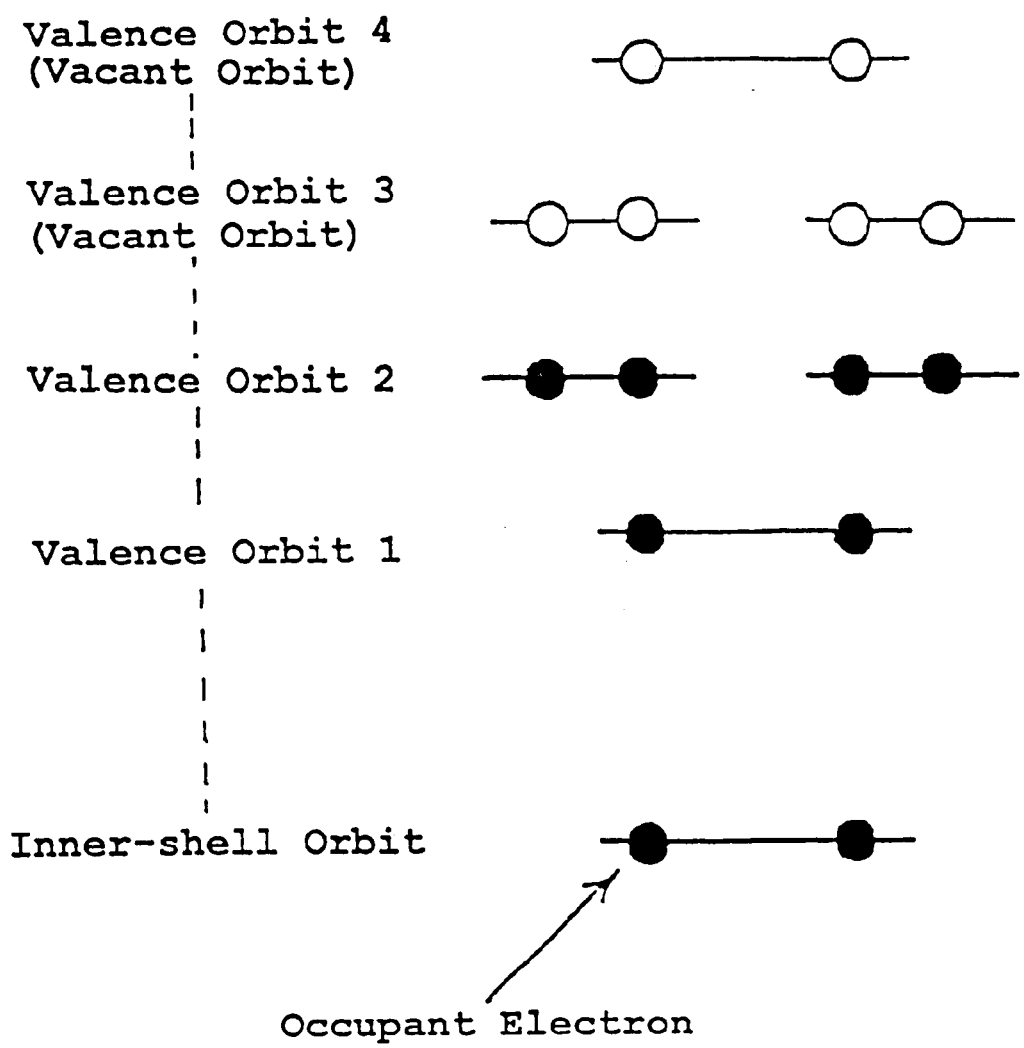
FIG. 1 is a conceptional diagram illustrating an electron structure of a molecule.
Figure 2:
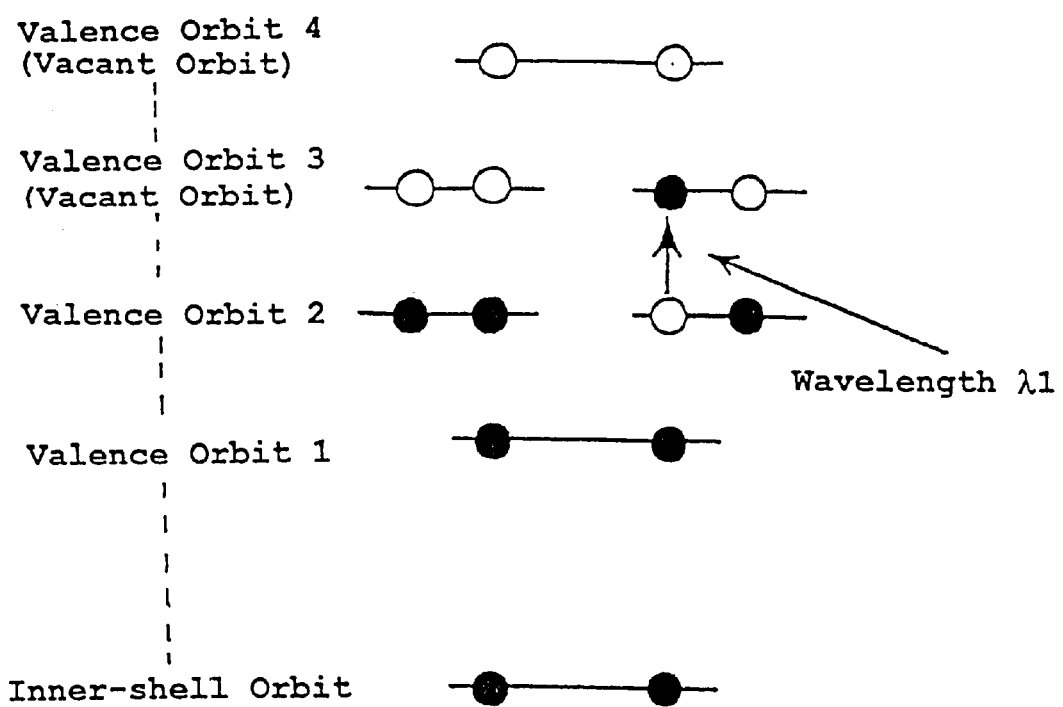
FIG. 2 is a conceptional diagram illustrating an excitation of the molecule of FIG. 1 to a first excited state by a wavelength λ1.
Figure 3:
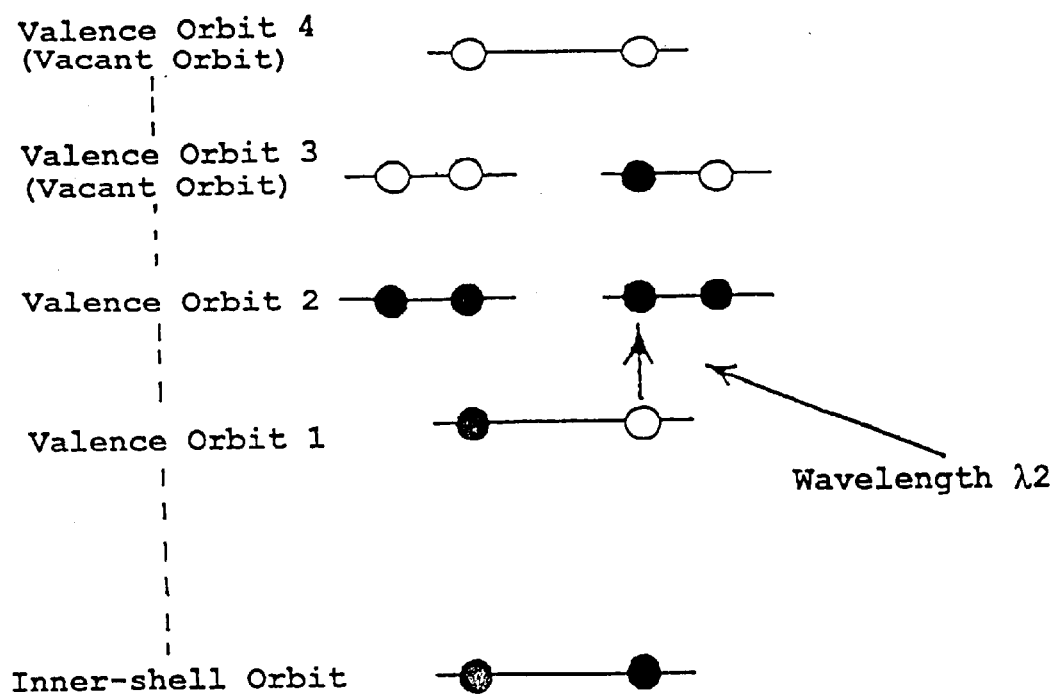
FIG. 3 is a conceptional diagram illustrating an excitation of the molecule of FIG. 1 to a second excited state by a wavelength λ2.
Figure 4:
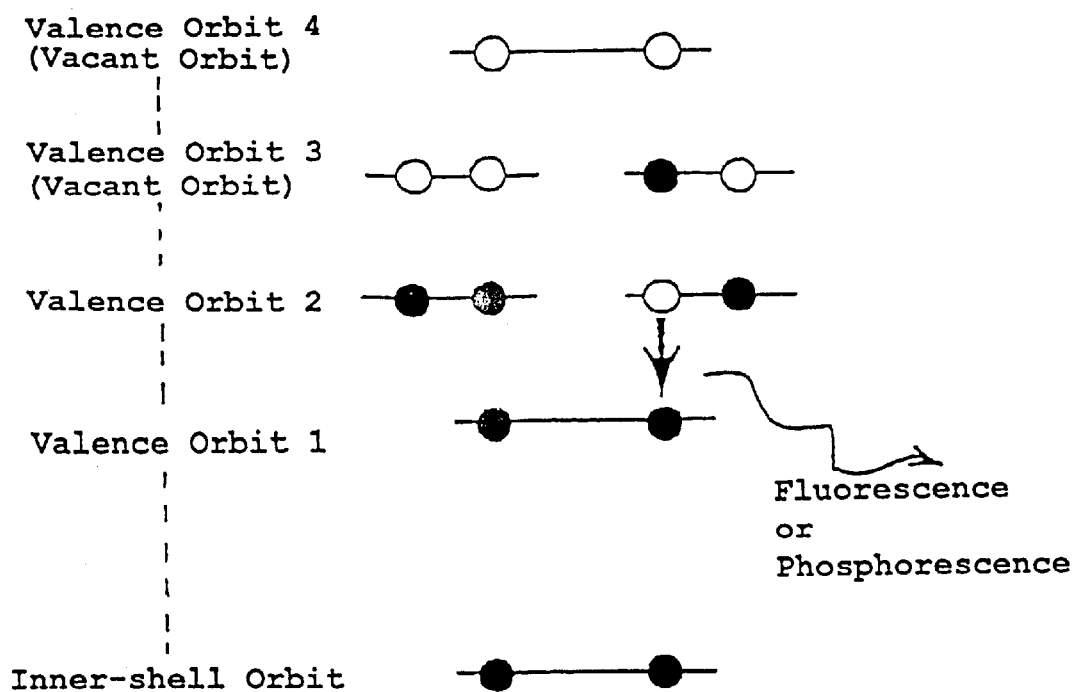
FIG. 4 is a conceptional diagram illustrating a deexcitation process, as accompanied by an emission, from the second electron excited state of FIG. 3 to a ground state.

Here, reference numerals in the Drawings designate the following components:

1 Nd:YAG Laser
2 BBO Crystal
3 Half Mirror
4 Raman Shifter
5 Mirror
6 Phase Plate
7 Dichroic Mirror
8 Dichroic Mirror
9 Condensing Objective Lens
10 Two-Dimensional Carriage Stage
100 Adjusted Specimen
11 Fluorescence Condenser Lens
12 Sharp Cut Filter
13 Pin Hole
14 15 Photomultiplier
16 Zonal Slit
17 Glass Lens
18 3-rd harmonics Generator
19 2-nd harmonics Generator
20, 24 Dichroic Mirror
21 Polarizer
22 Condenser Lens
23 Pin Hole
25 Objective Lens
26 Pin Hole
27 Sharp Cut Filter
28 Half Mirror
29 30 Mirror
31 Mercury Lamp
32, 33 Nd:YAG Laser
35, 36 KTP Crystal
37, 38 Half Mirror
39 Raman Shifter
40, 41 Dichroic Mirror
42 Relay Lens
43, 44, 45 Half Mirror
46, 48 Lens
47 Pin Hole
49 Spectrometer
50 CCD Camera Focusing Lens
51 CCD Camera
52 Zonal Mirror
53 Lens
54 Phase Plate 55 Output Mirror
56 Nd:YAG Laser
57 KTP Crystal
58 Notch Filter
59 Band-pass Filter
60 Sharp Cut Filter
61 Pin Hole
62 Shade Box
63 Cover Glass
64 Objective Lens
65 Condenser Lens
66 Personal Computer
67 Frequency Divider
68 Gate & Delay Generator
69 CCD Array
70 Diffraction Grating
71 CCD Camera
72 Frame Memory
73 CRT
74 Video Printer

BEST MODE FOR CARRYING OUT THE INVENTION

In the microscope system of the invention of this application; the adjusted specimen is dye with the molecule which has such three electronic states including at least the ground state that the excitation wavelength band from the first electron excited state to the second electron excited state overlaps a fluorescent wavelength band upon deexcitation by a fluorescent process from the first electron excited state to a vibrational level of the ground state.

Here will be described in detail this molecule, i.e., the so called "fluorescence labeler molecule" by considering the deexcitation process from the high electron excited state.

Figure 12:
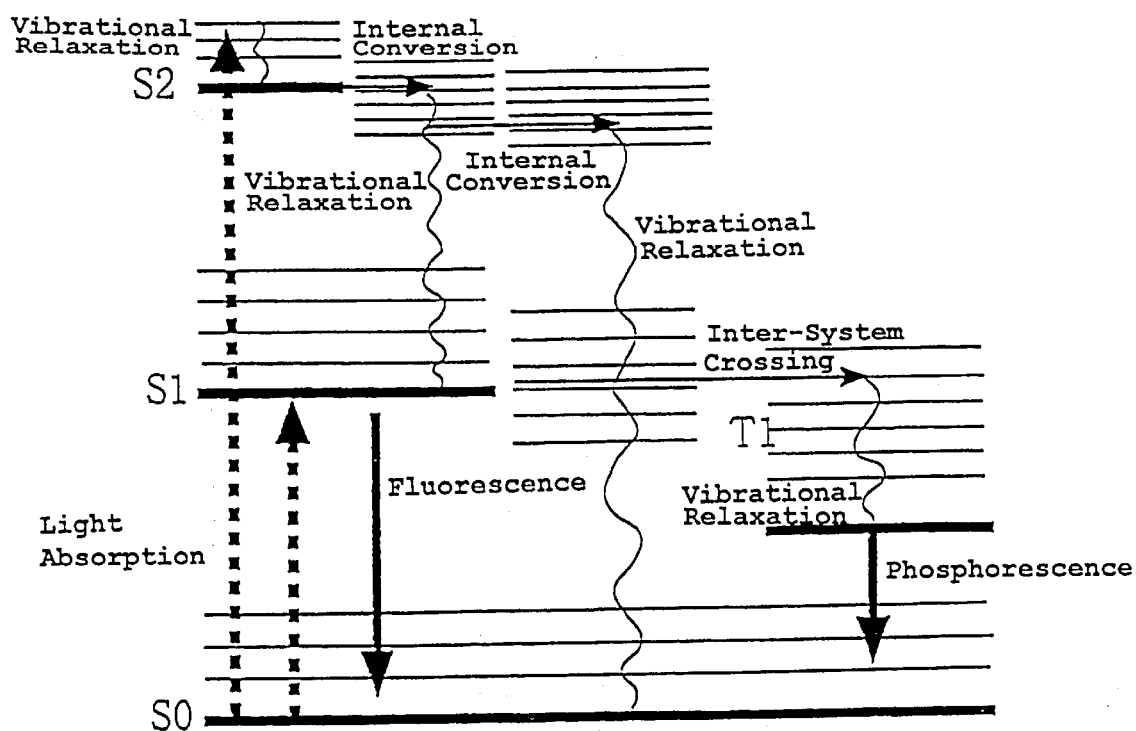
FIG. 12 is a diagram illustrating a deexcitation process of a molecule from a high excited state.

FIG. 12 conceptionally illustrates a deexcitation process of a molecule. Generally, when the molecule is excited from a ground state S0 to a lowermost (=first) excited state S1, the molecules having π electrons are deexcited to S0, emitting a fluorescence at a yield of several tens % at the most. This is fluorescence process. The remainder is deactivated directly to S0 without any radiation by vibrational relaxation, i.e., by internal conversion, but a portion thereof reaches a state T1 of which a spin multiplicity is different and a lifetime is extremely long, that is, performs a inter-system crossing, and then returns to S0 from the state T1, emitting a phosphorescence. In the ordinary fluorescent microscope, a specimen is dyed with a molecule having a high fluorescent yield and this molecule is excited to S1 by an light irradiation, so that fluorescence from S1 is observed and visualized.

On the other hand, when the molecule is excited to a second excited state S2 higher than S1, it deexcites to the ground state S0 by a remarkably complicated relaxation process, as illustrated in FIG. 12. For example, some of the excited molecules in S2 is deexcited to S0 or T1 by internal conversion or inter-system crossing. The remaining excited molecules are internally converted to the high vibrational level in S1, then they reach the lowermost vibrational level in S1. After this, the molecules return to S0 through the aforementioned relaxation process from S1.

What should be noted here is that the fluorescent emission yield from an excited state higher than S2 is extremely low. This is because many of the molecules in S2 are either deactivated without any radiation directly to S0 or deactivated without any radiation to S0 at a considerable ratio after having been internally converted to S1. And, since the molecules having reached the state T1 make no contribution to the fluorescent process, only a portion of the molecules having reached S1 emits a fluorescence. This is called the "Krash's law". Especially for a benzene derivative molecule in a gas phase, little fluorescence from S2 is observed.

Generally, the super-resolution microscope using the double resonance absorption process makes use of the fact that the fluorescent yield of a molecule from an electron excited state of S2 or higher level than S2 is extremely low, as described hereinbefore.

Figure 13:
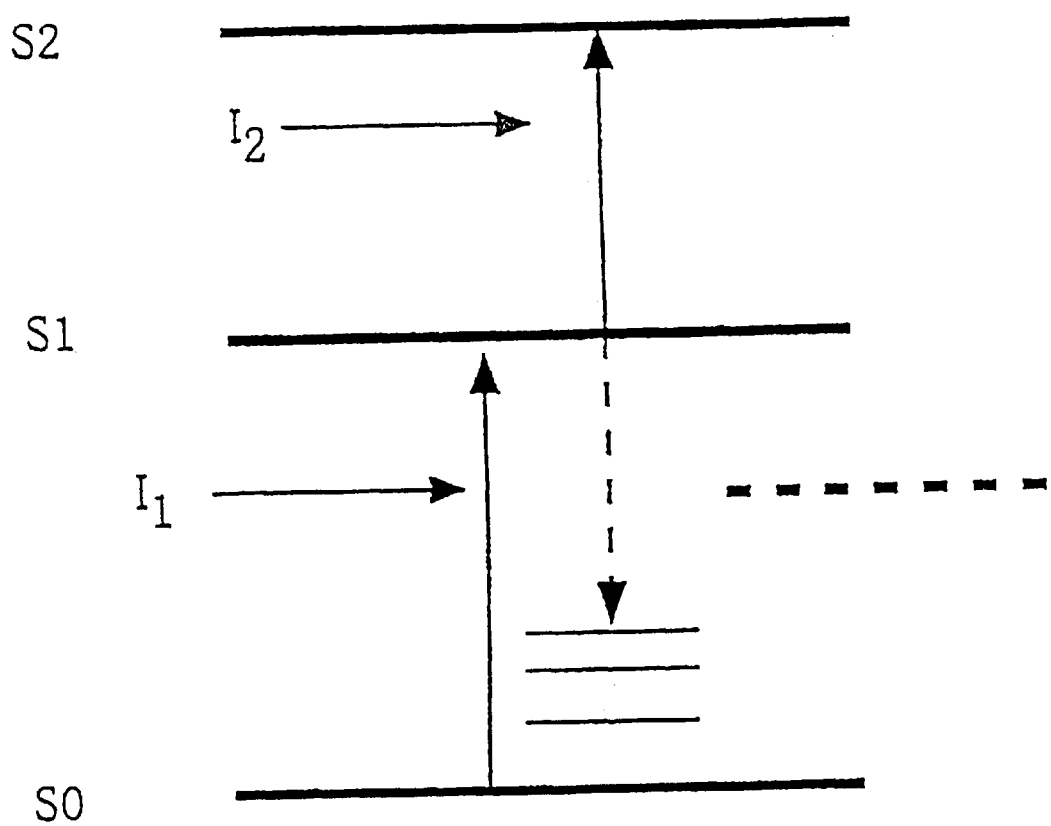
FIG. 13 is a diagram illustrating an energy diagram of a molecule whose wavelength range for exciting from a first electron excited state to a second excited state overlaps a florescent wavelength range upon deexcitation by a florescence process from the first electron excited state to a vibrational level of the ground state.

Here, some molecules have a structure, in which the wavelength band for transition from S1 to Sn (n=2 or more) overlaps a fluorescent emission wavelength band upon deexcitation from S1 to the vibrational level S0 by the fluorescent process, as illustrated in the energy diagram of FIG. 13. In the molecule having this electronic structure, there occurs a phenomenon that the fluorescent inhibition effect caused substantially by an erase light is intensified.

When exciting the molecule in S0 to S1 by a pump light of a wavelength λ1 and irradiating an erase light of a resonance wavelength λ2, the molecule in S1 transit to the state Sn, and, at the same time, most molecules are deexcited to the higher vibrational level of S0 by induced emission. At this time, the molecule excited to the state Sn is inhibited from fluorescence. On the other hand, for the molecule of the induced emission, a light of the same wavelength as that of the erase light is emitted, so that the intensity of the light of the same wavelength as that of the erase light slightly increases whereas the intensity of the fluorescence of a wavelength other than that of the erase light decreases. It follows that a substantially excellent fluorescent inhibition can be effected so long as the fluorescent emission of a wavelength other than that of the erase light is being monitored.

A molecule, of which the wavelength band upon transition from S1 to the state Sn overlaps the fluorescent emission wavelength band from S1 as described, is employed as a molecule for dyeing a specimen in the microscope system of the invention of this application. As a result, the fluorescent inhibition effect to which the aforementioned induced emission make contributions is added, thereby improving further the super-resolution of the microscope body. At the same time, the fluorescent inhibition can be easily caused even for a low intensity of the erase light, thus damage on the specimen to be observed can be reduced.

As an example of the molecule having the aforementioned optical characteristics, there is a molecule of a Rhodamine group belonging to a xanthene group.

Figure 14:
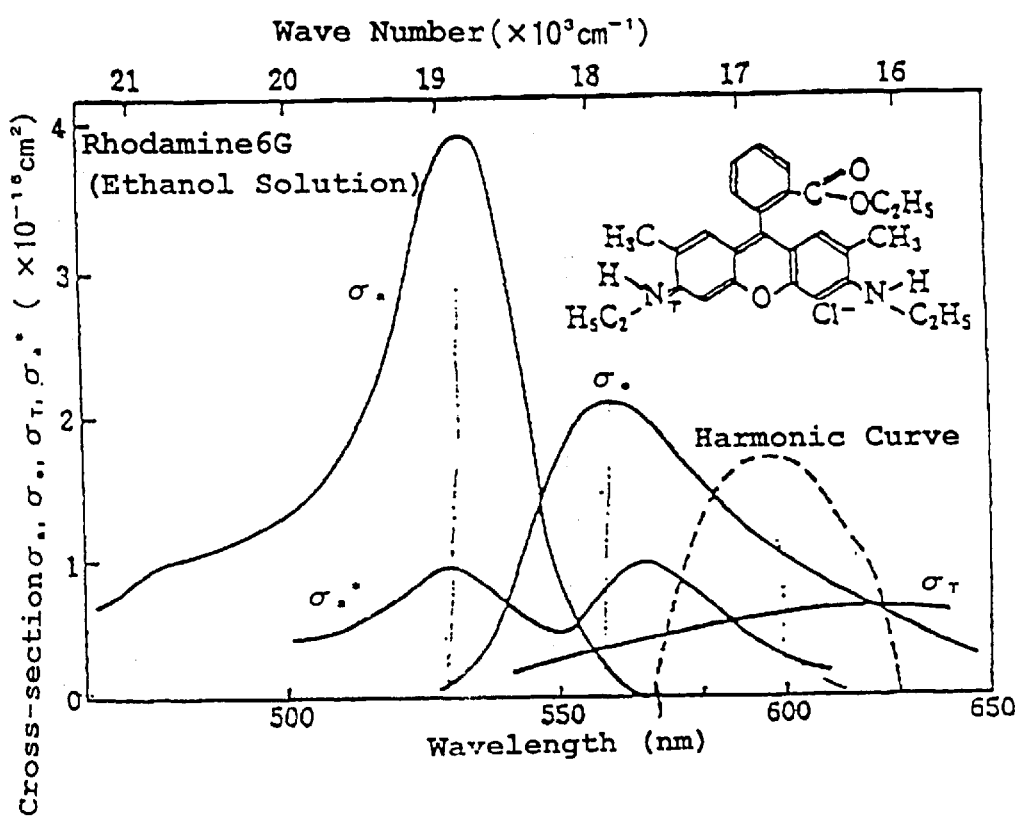
FIG. 14 is a diagram illustrating a molecular structural formula of Rhodamine 6G and relations between individual cross-sections as optical properties and wavelengths.

FIG. 14 illustrates a molecular structural formula of Rhodamine 6G that is a molecule of Rhodamine group and a relation between each cross-section and a wavelength as optical properties (E. Sahar & D. Treves: IEEE J. Quantum Electron., QE-13,962 (1977)). In FIG. 14, $\sigma_a$ indicates an absorption cross-section from S0 to S1; $\sigma_e$ indicates an induced emission cross-section from S1 to S0; $\sigma_a$*indicates an absorption cross-section from S1 to Sn; and $\sigma_T$ indicates an absorption cross-section from T1 to Tn.

As illustrated in FIG. 14, the resonance wavelength from S0 to S1 extends around about 530 nm (as should be referred to $\sigma_a$)., but the resonance wavelength from S1 to Sn extends around about 500 to 600 nm (as should be referred to σa*). And, the fluorescent emission band extends to the region of about 530 to 650 nm (as should be referred to $\sigma_e$), overlapping the resonance wavelength region from S1 to Sn. Moreover, it is found that a special wavelength band exists at about 530 to 600 nm. Specifically, the light of this wavelength band cannot excite the molecule from S0 to S1 but can effect the double resonance absorption process and the induced emission from S1 to Sn.

Generally, for not only this Rhodamine 6G but also a molecule of Rhodamine group, generally, the wavelength upon transition from S1 to Sn overlaps the fluorescent wavelength band upon deexcitation from S1 to the vibrational level of S0 through fluorescent process.

Also, for a molecule of coumarin group, the wave length band upon transition from S1 to Sn overlaps the fluorescent emission wavelength band from S1. For example, Coumarin 500 that is a coumarin group molecule, has a resonance wavelength from S0 to S1 extending around 260 nm, a resonance wavelength from S1 to Sn extending around 355 nm, and a fluorescent emission region extending to the region of 320 to 460 nm.

Basically, like the aforementioned Rhodamine group molecule or coumarin group molecule, a molecule having such optical properties contains one or more of a six-membered ring such as a benzene ring and a nitrogen base (i.e., purine base), or a six-membered ring derivative such as a benzene derivative and a purine derivative, and is exemplified by not only the Rhodamine group molecule or coumarin group molecule but also a xanthene group molecule, oxazine group molecule, cyanine group molecule, oxazole group molecule, oxadiazole group molecule or stilbene group molecule.

The following molecules are examples of such molecule: 2,2"-dimethyl-p-terphenyl; p-terphenyl (PTP); 3,3',2",3'"-tetramethyl-p-quaterphenyl; 2,2'"-demethyl-p-quaterphenyl; 2-methyl-5-t-butyl-p-quaterphenyl; 2-(4-biphenylyl)-5-(4-t-butylphenyl)-1,3,4-oxiazole (BPBD-365); 2-(4-biphenylyl)-phenyl-1,3,4-oxadiazole; 2,5,2"",5""-tetramethyl-p-quinquephenyl; 3,5,3"",5""-tetra-t-butyl-p-quinquephenyl; 2,5-diphenyloxazole; 2,5-diphenylfuran; PQP (p-quanterphenyl); 2,5-bis-(4-biphenylyl)-1,3,4-oxadiazole; p-quaterphenyl-4,4'"-disulfonic acid disodium salt; p-quaterphenyl-4,4'"-disulfonic acid dipotassium salt; 4,4'"-bis-(2-butyloctyloxy)-p-quaterphenyl; 3,5,3"",5""-tetra-butyl-p-sexiphenyl; 2-(1-naphthyl)-5-phenyloxazole; 2-(4-biphenylyl)-6-phenylbenzoxazotetrasulfonic acid potassium salt; 2-(4-biphenylyl)-6-phenylbenzoxazole-1,3; 4,4'-diphenylstilbene; [1,1'-biphenyl]-4-sulfonic acid, 4,4",-1,2-ethenediylbis-,dipotassium salt; 2,5-bis-(4-biphenylyl)-oxazole; 2,2'-([1,1'-biphenyl]-4,4'-diyldi-2,1-ethenediyl)-bis-benzenesulfonic acid disodium salt; 7-amino-4-methylcarbostyryl; 1,4-di[2-(5-phenyloxazole)]benzene; 7-hydroxy-4-methylcoumarin; p-bis(o-methylstylryl)-benzene; benzofuran,2,2'-[1,1'-biphenyl]-4,4'-diyl-bis-tetrasulfonic-acid; 7-dimethylamino-4-methylquinolom-2; 7-amino-4-methylcoumarin; 2-(p-dimethylaminostyryl)-pyridylmethyl iodide; 7-diethylamonocoumarin; 7-diethylamino-4-methylcoumarin; 2,3,5,6-1H,4H-tetrahydro-8-methylquinolizino-[9,9a,1-gh]-coumarin; 7-diethylamino-4-trifluoromethylcoumarin; 7-dimethylamino-4-trifluoromethylcoumarin; 7-amino-4-trifluoromethylcoumarin; 2,3,5,6-1H,4H-tetrahydroquinolizino-[9,9a,1-gh]-coumarin; 7-ethylamino-6-methyl-4-trifluoromethylcoumarin; 7-ethylamino-4-trifluoromethylcoumarin; 2,3,5,6-1H,4H-tetrahydro-9-carboethoxyquinolizino-[9,9a,1-gh]coumarin; 2,3,5,6-1H,4H-tetrahydro-9-(3-pyridyl)-quinolizino-[9,9a,1-gh] coumarin; 3-(2'-N-methylbenzimidazolyl)-7-N,N-diethylaminocoumarin; 2,3,5,6-1H,4H-tetrahydro-9-acetylquinolizino-[9,9a,1-gh]coumarin; N-methyl-4-frifluoromethylpiperidino-[3,2-g]-coumarin; 2-(p-dimethylaminostyryl)-benzothiazolylethyl iodide; 3-(2'-benzimidazolyl)-7-N,N-diethylaminocoumarin; brillantsulfaflavin; 3-(2'-benzothiazolyl)-7-diethytaminocoumarin; 2,3,5,6-1H,4H-tetrahydro-8-trifluoromethylquinolizino-[9,9a,1-gh]coumarin; 3,3'-diethyloxacarbocyanine iodide; 3,3'-dimethyl-9-ethylthiacarbocyanine iodide; disodium fluorescein (Uranin); 9-(o-carboxyphenyl)-2,7-dichloro-6-hydroxy-3H-xanthen-3-on2,7-dichlorofluorescien (Fluorescein 548); Fluorol 555 (Fluorol 7GA); o-(6-amino-3-imino-3H-xanthen-9-yl)-benzonic acid (Rhodamine 560); benzoic acid, 2-[6-(ethylamino)-3-(ethylimino)-2,7-dimethyl-3H-xanthen-9-yl],perchlorate (Rhodamine 575); benzoic acid, 2-[6-(ethylamino)-3-(ethylimino)-2,7-dimethyl-3X-xanthen-9-yl],ethyl ester, monohydrochloride (Rhodamine 590); 1,3'-diethyl-4,2"-quinolyloxacarbocyanine iodide; 1,1'-diethyl-2,2'-carbocyanine iodide; 2-[6-(diethylamino)-3-(ethylamino)-3H-xanthen-9-yl]benzonic acid (Rhodamine 610); ethanaminium,N-[(6-diethylamino)-9-(2,4-disulfophenyl)-3H-xanthen-3-ylidene]-N-ethylhydroxide, inner salt, sodium salt; Malachit Green; 3,3'-diethylthiacarbocyanine iodide; 1,3'-diethyl-4,2'-quinolythiacarbocyanine iodide; 8-(2-carboxyphenyl)-2,3,5,6,11,12,14,15-octahydro-1H,4H,10H,13H-diquinolizino[9,9a,1-bc:9',9a',1-hi]xantylium perchlorate (Rhodamine 640); 4-dicyanmethylene-2-methyl-6-(p-dimethylaminostyryl)-4H-pyran; 3,3'-diethyloxadicarbocyanine iodide; 8-(2,4-disulfophenyl)-2,3,5,6,11,12,14,15-octahydro-1H,4H,10H,13H-diquinolizino[9,9a,1-bc:9',1-hi]xanthene (Sulforhodamine640); 5,9-diaminobenzo[a]phenoxazonium percrorate; 9-diethylamino-5H-benzo(a)phenoxazine-5-one; 5-amino-9-diethylimino[a]phenoxazonium perchlorate; 3-ethylamino-7-ethylimino-2,8-dimethylphenoxazine-5-ium perchlorate; 8-(trifluoromethyl)-2,3,5,6,11,12,14,15-octahydro-1H,4H,10H,13H-diquinolizino[9,9a,1-bc:9',9a,1-hi]xantbylium perchlorate; 1-ethyl-2-(4-(p-dirmethylaminophenyl)-1,3-butadienyl)-pyridinium perchlorate; Carbazine 122; 9-ethylamino-5-ethylimino-10-methyl-5H-benzo(a)phenoxazonium perchlorate; 3-diethylamino-7-diethyliminophenoxazonium perchlorate; 3-diethylthiatricarbocyanine iodide; Oxazine 750; 1-ethyl-4-(4-(p-dimethylaminophenyl)-1,3-butadienyl)-pyridinium perchlorate; 1,1',3,3,3',3'-hexamethylindodicarcyanine iodide; 1,1'-diethyl-4,4'-carbocyanine iodide; 2-(4-(p-dirmethylaminophenyl)-1,3-butadienyl)-1,3,3-trimethyl-3H-indolium perchlorate; 2-(4-(p-dimethylaminophenyl)-1,3-butadienyl)-3-ethylbenzothoazolium perchlorate; 1,1'-diethyl-2,2'-dicarbocyanine iodide; 1-ethyl-4-(4-(9-(2,3,6,7-tetrahydro-1H,5H-benzo(i,j)-chinolinozinium))-1,3-butadienyl)-pyridinium perchlorate; 3,3'-dimethyloxatricarbocyanine iodide; 1-ethyl-4-(4-(p-dimethylaminophenyl)-1,3-butadienyl)-quinolinium perchlorate; 8-cyano-2,3,5,6,11,12,14,15-octahydro-1H,4H,10H,13H-diquinolizino[9,9al-bc:9a',1-hi]xanthylium perchlorate (Rhodamine 800); 2-(6-(4-dimethylaminophenyl)-2,4-neopentylene-1,3,5)-3-methylbenzothiazolium perchlorate; 1,1',3,3,3',3'-hexamethylindotricarbocyanine iodide; IR125; 3,3'-diethylthiatricarbocyanine iodide; IR144; 2-(6-(9-(2,3,6,7-tetrahydro-1H,5H-benzo(i,j)-chinolinozinium))-2,4-neopentylene-1,3,5-hexatrienyl)-3-methylbenzothiazolium perchlorate; 3,3'-diethyl-9,11-neopentylenethiatricarbocyanine iodide; 1,1',3,3,3'-hexamethyl-4,4',5,5'-dibenzo-2,2'-indotricarbocyanine iodide; 3,3'-diethyl-4,4',5,5'-dibenzothiatricarbocyamine iodide; 1,2'-diethyl-4,4'-dicarbocyanine iodide; IR140; 2-(8-(4-p-dimethylaminophenyl)-2,4-neopentylene-1,3,5,7-octatetraenyl)-3-methylbenzothiazolium perchlorate; IR132; 2-(8-(9-(2,3,6,7-tetrahydro-1H,5H,benzo(i,j)

chinolinozinium))-2,4-neopentylene-1,3,5,7-octatetraenyl)-3-methylbenzothiazolium perchlorate; IR26; and IR5.

In the above molecules, for example, 7-ethylamino-4-trifluoromethylcoumarin ($C_{12}H_{10}NO_2F_3$: Coumarin 500) that is a coumarin group molecule has an excitation wavelength band from S0 to S1 extending around 266 nm; an excitation wavelength band from S1 to S2 extending around 532 nm, and a fluorescent wavelength band at 532 nm.

These wavelengths 266 nm and 532 nm correspond to the 4-th harmonics and the 2-nd harmonics of the YAG laser, respectively, so that they can be easily produced by modulating their fundamental-wave or harmonic-wave with a nonlinear crystal such as a BBO crystal or KTP crystal as a wavelength convertible nonlinear medium or a wavelength modulating element.

Accordingly, in the microscope system of this invention, if the coumarin group molecule is used as the specimen dyeing molecule and the YAG laser is employed as a light source for the pump light and a light source for the erase light in the microscope body, the microscope system not only can achieve an excellent super-resolution but also can have superior workability and optical performance to those of the microscope of the prior art using a dye laser.

Specifically, the wavelength to be employed can be determined merely by initially setting the angle of the nonlinear crystal basically, so that a desired excitation wavelength can be easily emitted without any troublesome wavelength adjustment. Furthermore, there is neither fluctuation nor reduction of the laser power due to the degradation of the dye and the energy conversion efficiency is excellent, so that there is no need to use a laser of a high power output thus its light source can be small-sized and inexpensive and also damage on the biological specimen can be reduced.

For the beam profile of the YAG laser, there has been established the technique of emitting a satisfactory Gaussian beam having an adjusted phase plane, so that an erase light of an excellent hollow beam type with optical-axis symmetry can be produced.

As such YAG laser, for example, a commercially available mode-locked YAG laser having a pulse width of 20 psecs or less and a repetition frequency of 100 MHz can be used.

Similarly, no matter whether the dyed molecule might be those of the xanthene group or Rhodamine group, on the other hand, the pump light and the erase light can be produced by using the YAG laser and the nonlinear crystal.

For Rhodamine 6G, for example, the resonance wavelength from S0 to S1 extends around 530 nm, and the resonance wavelength from S1 to Sn extends around 500 to 600 nm, as has been described hereinbefore. The pump light around 530 nm can be coped with by the 2-nd harmonics of the YAG laser. The erase light around 500 to 600 nm can be easily produced by using the Raman effect (or the so-called "Raman shifter").of the nonlinear crystal. By filtering the light of 532 nm of the 2-nd harmonics of the YAG laser through the Raman shifter, for example, it is possible to produce a laser beam around 560 nm, as shifted by about 30 nm to a longer wave side, in a conversion efficiency of about 20%.

Further, a laser beam having a sum frequency or a difference frequency between fundamental-wave and harmonic -wave, as produced by using the nonlinear crystal, of the YAG lasers can also be employed as the pump light or the erase light.

It is quite natural that not only the YAG laser but also a gas laser, a solid laser or a semiconductor laser of a fixed wavelength, a variety of nonlinear media or a wavelength modulation element can be used in conformity to the aforementioned individual molecules.

For example, as the gas laser, an excimer laser, a copper vapor laser, an argon laser, a He—Ne laser, a $CO_2$ laser, a He—Cd laser or a nitrogen laser may be used, and as the solid laser, a Nd:YAG laser, a Ti sapphire laser, a YLF laser or a ruby laser may be used.

Of these individual lasers, the mode-locked type laser has a high repetition frequency and a pulse amplitude of several tens psecs or less and is the light source which is more suited for the super-resolution microscope body in the microscope system of this invention.

In recent years, a semiconductor-laser-excited and mode-locked type sold-state laser of small size, high luminance, short pulse and high repetition is realized at a low cost and in a maintenance-free manner, so that this solid-state laser has all the conditions for exploiting the functions of the super-resolution microscope body sufficiently.

Each of the aforementioned gas laser, solid laser and semiconductor laser is used as the light source for the pump light of the wavelength $\lambda 1$ and as the light source for the light of the wavelength $\lambda 2$ to produce the pump light and the erase light with their vibration wavelength or harmonic-wave, or with the sum frequency or differential frequency between the vibration wavelength and the harmonic-wave being set at the wavelength $\lambda 1$ and the wavelength $\lambda 2$. On the other hand, the pump light of the wavelength $\lambda 1$ and the erase light of the wavelength $\lambda 2$ can also be produced by modulating the wavelength of the fundamental-wave or harmonic-wave of those various light sources with the various nonlinear media such as nonlinear crystals or the wavelength modulating elements.

Here, in order that the super-resolution microscope using the fluorescent inhibiting effect may have a theoretical resolution, the beam to be produced by condensing the erase light which is the light of the wavelength $\lambda 2$ on the specimen surface has to be shaped to have a zero optical intensity at a central portion thereby to leave a fluorescent region at the central portion in the irradiation region, as has been described hereinbefore.

In this invention, the beam to be produced by condensing the erase light is given a phase distribution, in which the phase is shifted by $\pi$ at an object position with respect to its optical axis in a plane normal to the optical axis so that the optical intensity at the central portion may be zero.

A Bessel beam is suited for the beam having such phase distribution.

Figure 15:
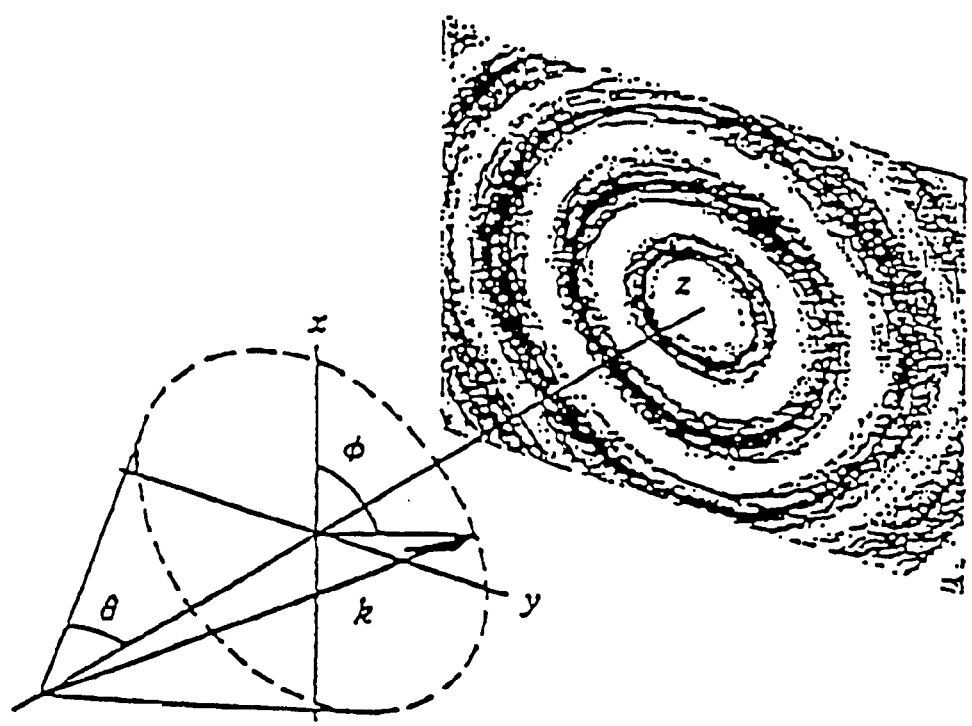
FIG. 15 is a diagram illustrating a coordinate system for expressing a Bessel beam.

If a coordinate system illustrated in FIG. 15 is assumed, for example, the Bessel beam can be expressed in the form of the following Equation:

$$I(x,y)=|E(x,y)|^2|E_0\int_0^{2\pi}\exp[ik \sin\theta(x\cos\phi+y\sin\phi)\cdot\exp(-im\phi)d\phi]d\phi|^2 \qquad \text{Equation 11}$$

In this equation, E (x, y) indicates a field vector, and EO indicates an amplitude of the field vector. If here it is assumed that m=1, the above equation expresses a 1-st-order-Bessel-beam. This 1-st-order-Bessel-beam has a unique point on which the field intensity is zero on the optical axis, and is achieved in fact by solving the following wave equation of electromagnetic waves:

$$\Delta E(x, y) - \mu\varepsilon\frac{\partial E(x, y)}{\partial t} = 0 \qquad \text{Equation 12}$$

If a boundary condition axially symmetric with respect to an axis is given, Eq. 12 can be rewritten with a cylindrical coordinate system (r, φ, z) in the following form:

$$\frac{1}{r}\frac{\partial}{\partial r}\left(\frac{\partial E}{\partial r}\right) + \frac{1}{r^2}\frac{\partial^2 E}{\partial^2 \phi} + \frac{\partial^2 E}{\partial^2 z} + k^2 E = 0 \qquad \text{Equation 13}$$

Here, k indicates a wave number, and a solution of Eq. 11 to be expressed by a overlap of the Bessel function can be obtained if the coordinate system illustrated in FIG. 15 is used again.

Figure 16:
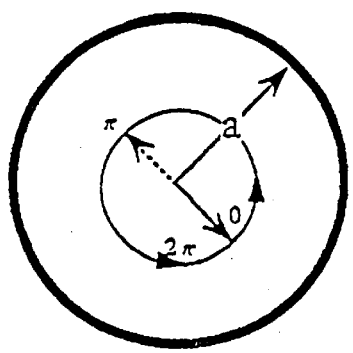
FIG. 16 is a diagram illustrating a phase distribution of a beam plane of the Bessel beam.

FIG. 16 illustrates a phase distribution of a beam plane, i.e., a pupil plane of the 1-st-order-Bessel-beam for m=1. As apparent from FIG. 16, the 1-st-order-Bessel-beam has a phase distribution, in a plane normal to its optical axis, changing continuously from 0 to 2 π when turned once around the optical axis, and the phases of electric fields axially symmetric are shifted by π from each other. As a result, it is found that the electric fields completely cancel each other on the optical axis to zero so that the Bessel beam has a singular point at which the field intensity is zero on the optical axis.

In short, the microscope system of this invention is enabled to leave the fluorescent region at the central portion of the irradiation region thereby to have a theoretical resolution by making the condensed beam of the erase light into the Bessel beam, especially, the 1-st-order-Bessel-beam, for example with the condensing optical system.

Figure 17:
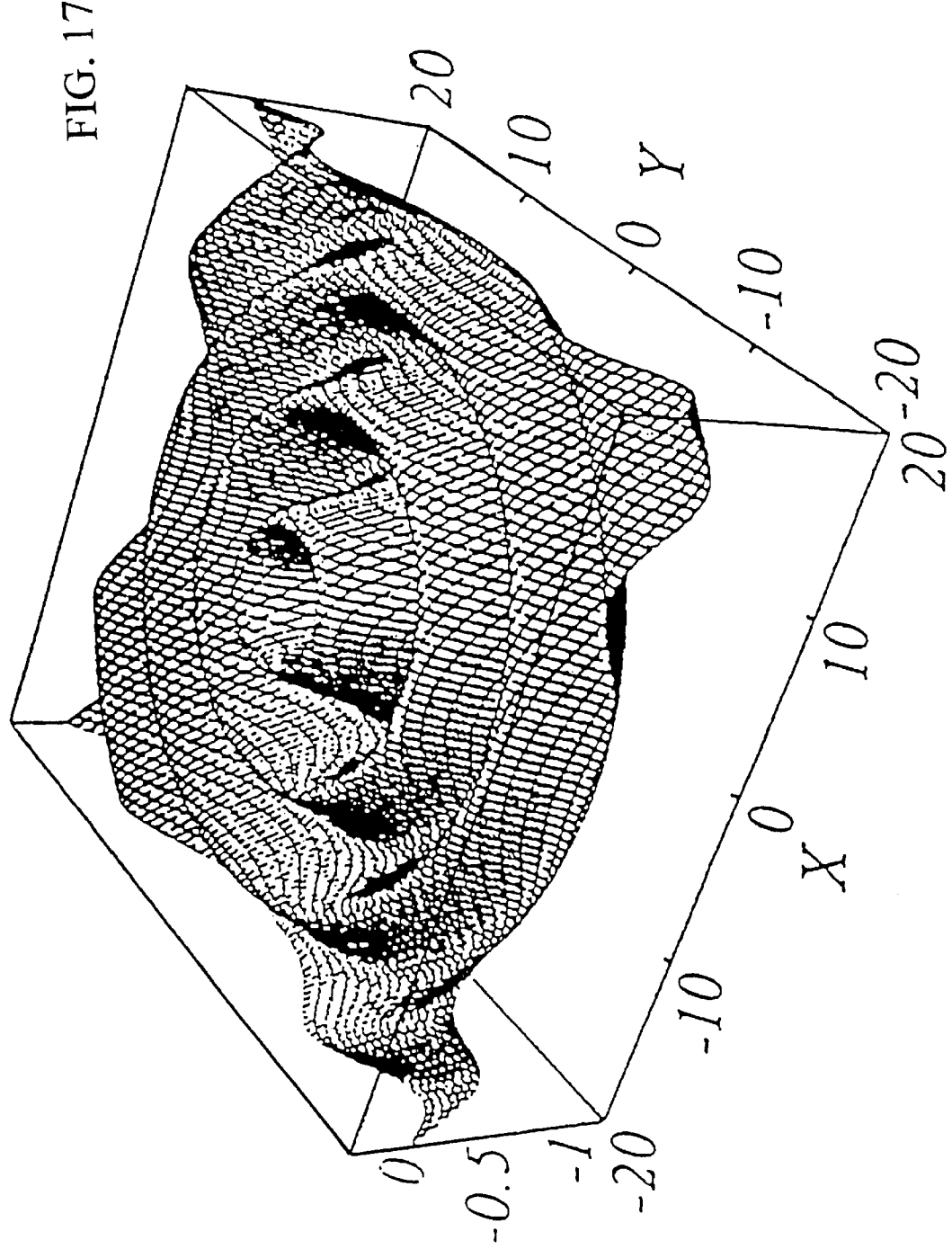
FIG. 17 is a diagram illustrating a two-dimensional intensity distribution of a 1-st-order-Bessel-beam.

Moreover, this Bessel beam is a quasi-nondiffractive beam which will not apparently diffuse, as illustrated in a profile that is a two-dimensional intensity distribution exemplified in FIG. 17.

The microscope of the prior art employs an objective lens having a large numerical aperture so as to enhance the resolution by reducing the diffractive limit, thus its focal depth is extremely reduced, making the focusing operation difficult. In the microscope system of this invention, however, the Bessel beam as the condensing beam of the erase light is a quasi-nondiffractive beam so that its focal depth is substantially enlarged, lightening the focusing burden. In the microscope body, moreover, the resolution is dominated by the erase light so that the operability is enhanced without lowering the resolution.

It is made possible by a condensing optical system using the existing optical element to easily form the condensed beam of the erase light, as exemplified by the Bessel beam having the aforementioned optical characteristics, that is, the condensed beam, having a boundary condition axially symmetric with respect to the optical axis and also having a phase distribution in which a phase is shifted by π at the position symmetric with respect to the optical axis.

In order to give the boundary condition axially symmetric with respect to the optical axis, the condensing optical system is preferably provided with a zonal optical system such as a reflecting objective lens having a zonal pupil, that is an optical system having a zonal aperture, or a diffractive optical system such as a Fresnel zone plate, or an axicon.

Additionally, in order to give the phase distribution in which the phase is shifted by π at a position symmetric with respect to the optical axis, the condensing optical system may also be provided with a phase plate having such a refractive-index distribution or optical-path-difference distribution as will give a phase difference distribution in a plane normal to the optical axis.

Figure 18:
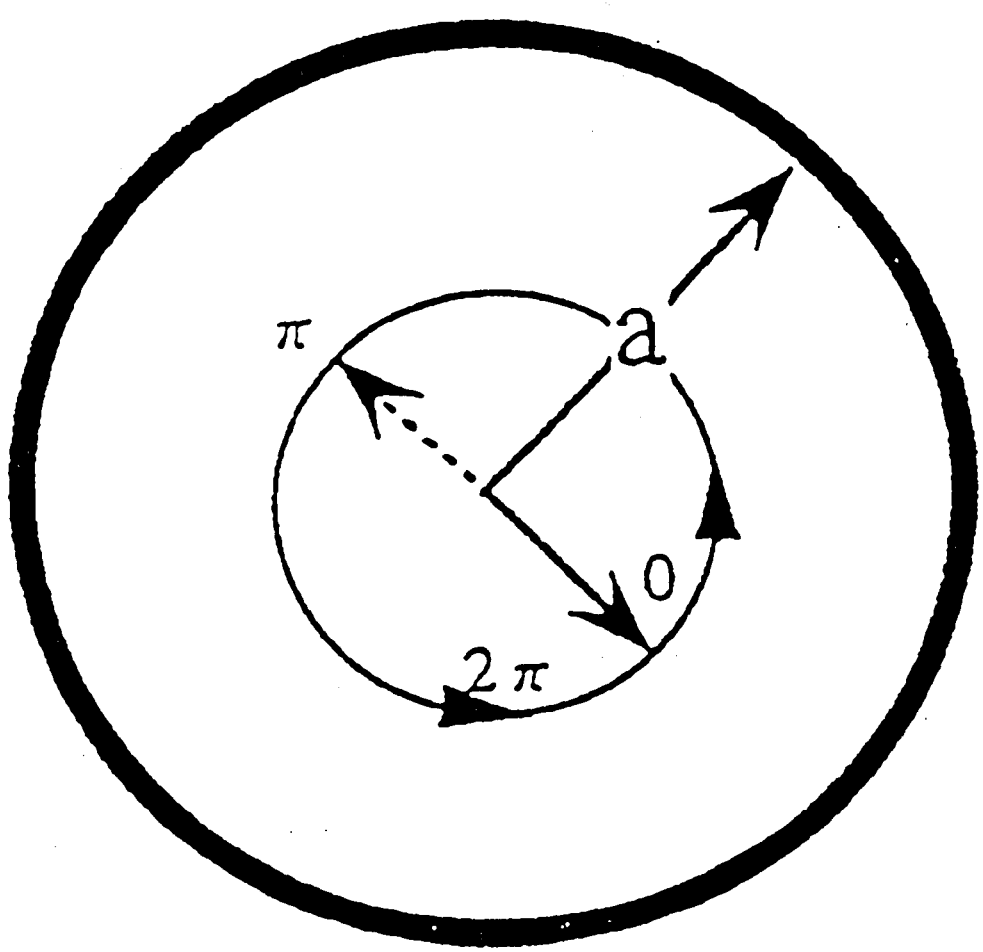
FIG. 18 is a diagram illustrating a phase distribution to be imparted to a condensed beam of an erase light by a phase plate.

For example, the condensed beam having the phase distribution changing continuously from 0 to 2 π when turned once around the optical axis in the plane normal to the optical axis, like a complete 1-st-order-Bessel-beam, is formed by changing its refractive-index distribution or optical-path-difference distribution continuously from 0 to 2 π when the phase plate makes one turn in a direction to turn around the optical axis in the plane normal to the optical axis of the beam, as illustrated in FIG. 18.

On the other hand, the condensed beam which is not the complete 1-st-order-Bessel-beam but the condensed beam can be formed, if it has the phase distribution changing discontinuously from 0 to 2 π when turned once around the optical axis in the plane normal to the optical axis, even if the refractive-index distribution or optical-path-difference distribution changes discontinuously from 0 to 2 π. The light source for the erase light may be given a function to form such condensed beam.

Further, the aforementioned boundary condition can be given to convert the erase light itself directly into the 1-st-order-Bessel-beam by inserting, into a resonater of a laser as the erase light source, a transmission type zonal diffraction grating, a ring-shaped zonal mirror, a Fresnel zone plate, a zonal aperture, or a phase plate giving a phase difference in which electric fields axially symmetric with respect to the electric field in a plane normal to the optical axis are shifted by π from each other.

Furthermore, by adjusting the boundary condition of a resonator of a laser as the erase light source thereby to form an axially symmetric mode pattern, such as TEM11, having a zero intensity on the optical axis and then by condensing this mode pattern with the diffracting optical system having the aforementioned zonal aperture, the laser beam of any vibrational mode such as Gauss's type, Laguerre's type or Hermitian's type having a higher order mode pattern, for example, may be converted into the condensed beam of the erase light.

On the other hand, the microscope body of the microscope system of this invention can also have a micro-manipulator function capable to capture and move a specimen particle with a hollow beam.

When the hollow beam is irradiated, the specimen particle is absorbed into the region of a high laser intensity, and their stable point becomes to the hollow portion of the condensed point position of the hollow beam, so that the particle is completely sealed and captured in the hollow beam. In the microscope body of this invention, the specimen to be captured is hardly irradiated with the laser beam so that its damage can be inhibited. Moreover, the spatial movement can be realized by scanning the beam by the optical system such as the galvano-mirror as in the ordinary laser beam.

In addition, the laser intensity proper for the capture is known to be about several tens $MW/cm^2$; and this intensity is substantially equal to the maximum intensity of the erase light used in the microscope body of the microscope system of this invention, so that the aforementioned erase light source and condensing optical system can be used as they are.

Accordingly, in the microscope system of this invention, the specimen can be captured and moved without any light irradiation damage by using the hollow beam, so that a high-grade micro-manipulator function can be achieved.

Embodiments of this invention will be described with its embodiments with reference to examples along with the accompanying drawings.

EXAMPLES

Example 1

In the microscope system of this invention, the adjusted specimen is dyed with the Rhodamine 6G, and the microscope body is provided with the YAG laser as the light source for the pump light (i.e., the light of the wavelength $\lambda 1$ for exciting the Rhodamine 6G from the ground state S0 to the first excited state S1).and the light source for the erase light (i.e., the light of the wavelength $\lambda 2$ for exciting the Rhodamine 6G in the first excited state S1 to the second excited state S2). The microscope body is further provided with the Raman shifter as the wavelength modulating element of the YAG laser.

The Rhodamine 6G can realize, as described hereinbefore, an excellent fluorescent inhibition by double resonance absorption and induced emission, as described hereinbefore, and its excitation wavelength $\lambda 1$ from S0 to S1 is 532 nm and its excitation wavelength $\lambda 2$ from S1 to S2 is 560 nm. Hence, the 2-nd harmonics light (=532 nm) of the YAG laser is employed as the pump light and the light made by modulating the 2-nd harmonics to 560 nm with the Raman shifter is employed as the erase light.

The following Table 1 shows the optical parameters of the Rhodamine 6G at 532 nm and 560 nm:

TABLE 1

| | |
|---|---|
| Absorption Cross-Section of S0 → S1 | $\sigma_{01}$: 4 × 10$^{-16}$ cm$^2$ (532 nm) |
| Absorption Cross-Section of S1 → S2 | $\sigma_{12}$: 1 × 10$^{-16}$ cm$^2$ (560 nm) |
| Fluorescent Emission Area | $\sigma f$: 2 × 10$^{-16}$ cm$^2$ (560 nm) |
| Fluorescent Lifetime | $\tau$: 3 nsecs or more |

Moreover, the beam to be produced by condensing the erase light with the use of the condensing optical system of the microscope body has a phase distribution in which the phase is shifted by $\pi$ at a position symmetric with respect to the optical axis in a plane normal to the optical axis and in which the phase changes continuously from 0 to 2 $\pi$ when turned onced around the optical axis. And, the condensing optical system is provided with a phase plate having the refractive-index distribution or optical-path-difference distribution, as illustrated in FIG. 18, capable of giving such phase distribution to the condensed beam of the erase light.

The level of the resolution of the microscope body in such microscope system of this invention can be expressed by Eq. 11 that is the general Equation of the 1-st-order-Bessel-beam mentioned hereinbefore.

Figure 19:
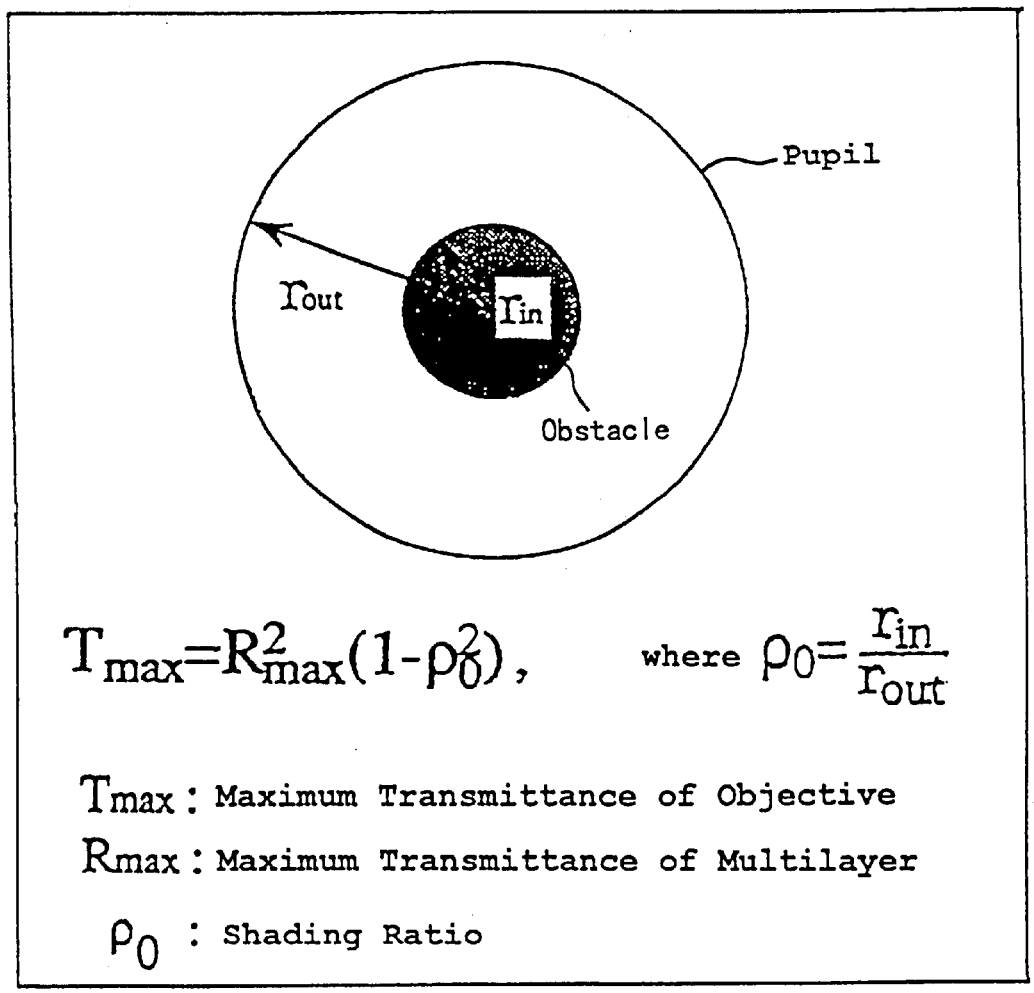
FIG. 19 is a diagram illustrating one example of a numerical aperture of a condensing optical system.

This resolution level can be-rewritten in the form of convolution calculations, as expressed by the following Equation, if the numerical aperture of the condensing optical system of the erase light is specifically given as illustrated in FIG. 19:

$$I(x,y)=|E(x,y)|^2|E_0 \iint_{x^2+y^2 \leq a^2} PSF(x-x',y-y') \exp[-i\phi(x',y')]x'dy'|^2 \qquad \text{Equation 14}$$

In this Equation, PSF(x, y) indicates a two-dimensional point-image distribution function of the optical system, $\phi$ (x, y)indicates the phase distribution; and a indicates the radius of integration area.

When the condensing optical system is a zonal optical system, PSF(x, y) is given by the following Equation:

$$PSF(x, y) = \frac{2J_1(2\pi\xi)}{2\pi\xi} - \frac{2\rho_0 J_1(2\pi\xi)}{2\pi\xi} \qquad \text{Equation 15}$$

Here, $\rho_0$ indicates a shading factor of the pupil of the condensing optical system, and $\xi$ is expressed by the following Equation:

$$\xi = \frac{NA}{\lambda}\sqrt{x^2 + y^2} \qquad \text{Equation 16}$$

Here, NA indicates the numerical aperture of the condensing optical system, and x indicates the wavelength of the erase light.

In Eq. 15, $\rho_0$ takes a value between 0 to 1 and, at 0, indicates PSF(x, y) of the condensing optical system not being the zonal optical system.

Here, if I (x, y) given by Eq. 14 is substituted into Eq. 8, the fluorescent intensity F1(x, y) when the specimen surface having homogeneously distributed molecule in S1 is irradiated with the erase light can be determined by the following Equation:

$$F_1(x,y)=\Phi(I_0\sigma_{01}N_0t)\cdot e^{-(\sigma_{12}I(x,y)+1/\tau)T} \qquad \text{Equation 17}$$

When the induced emission contributes to the fluorescent inhibition, moreover, Eq. 17 turns into Eq. 18 as the induced emission cross-section being $\sigma_f$:

$$F_1(x,y)=\Phi(I_0\sigma_{01}N_0t)\cdot e^{-((\sigma_{12}+\sigma_f)I(x,y)+1/\tau)T} \qquad \text{Equation 1}$$

Consequently, when the fluorescence labeler molecule is the Rhodamine 6G and the condensed beam of the erase light has the aforementioned phase distribution, it is possible to estimate, by using this Eg.18, the level of spatial resolution of detecting the fluorescence to be emitted upon deexcitation of the Rhodamine 6G the first excited state to the ground state Hence, the spatial resolution to be achieved in detection by the microscope body of the microscope system of this invention in the present Example 1 was determined from Eq. 18.

Table 2 shows the environmental parameters used for this determination:

TABLE 2

| | |
|---|---|
| Numerical Aperture of Condenser Lens | 0.75 |
| Shading Factor of Optical System Pupil | 0.95 |
| Pulse Width of Laser Beam | 150 psecs |
| Wavelength of Pump Light | 532 nm |
| Wavelength of Erase Light | 560 nm |
| Photon Flux of Erase Light | 9.6 × 10$^{25}$ photons/sec/cm$^2$ |
| Laser Intensity of Erase Light | 34 MW/cm$^2$ |

The optical parameters of the Rhodamine 6G adopted the values of the aforementioned Table 1.

Here, the photon flux of the pump light is not designated, but the discussions on the yield and homogeneity of the S1 are particularly ignored while assuming that the $\sigma_{12}$ in the wavelength band of the 2-nd harmonics of the YAG laser has such a large absorption cross-section as can produce a sufficient number of S1 in the case of the Rhodamine 6G.

Figure 20:
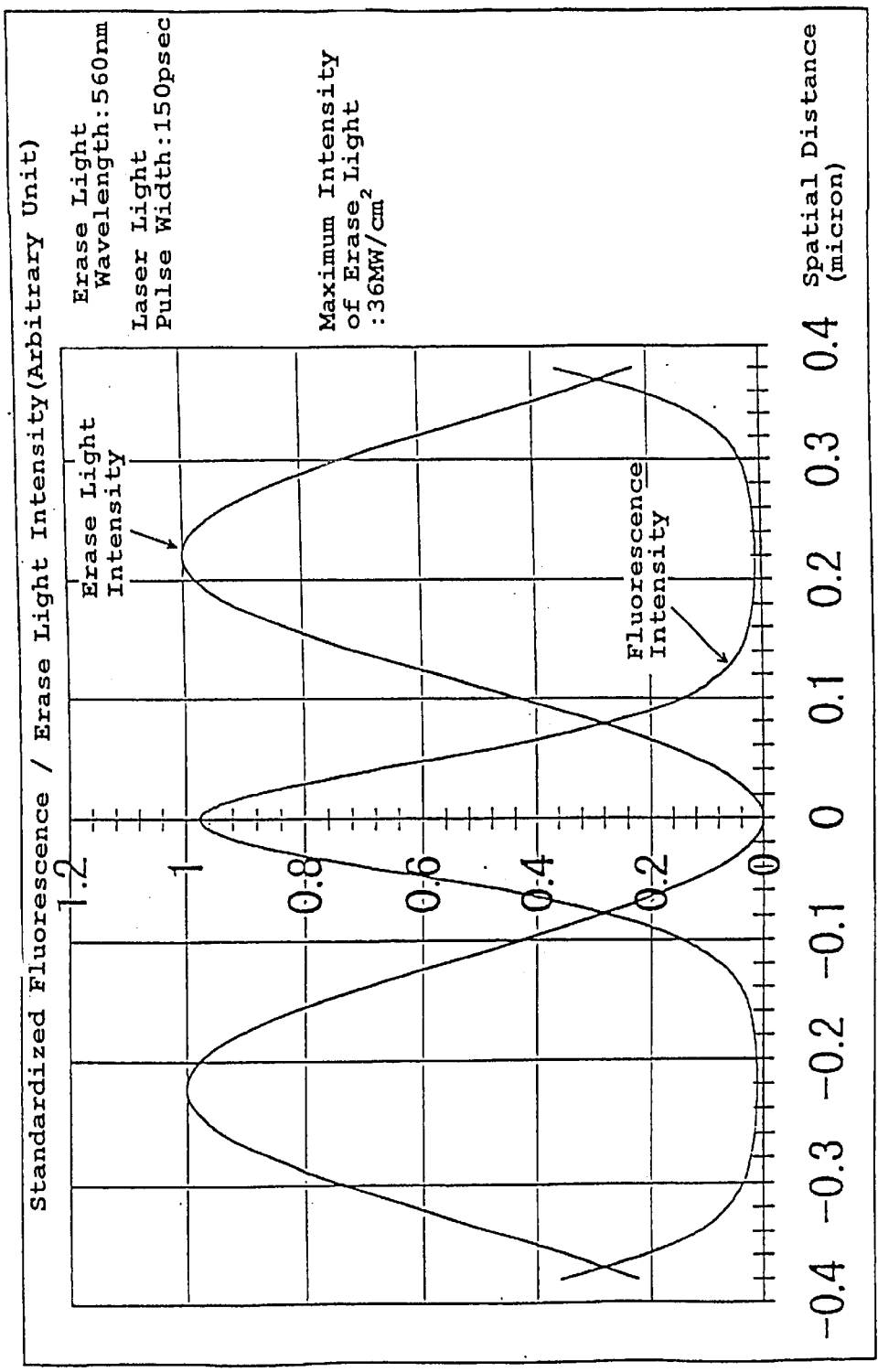
FIG. 20 is a diagram illustrating one example of an erase light condensed beam intensity and a fluorescent intensity in the microscope body of a microscope system of this invention of Example 1.

FIG. 20 illustrates one example of a calculated erase light intensity I(x, y) and a fluorescent intensity $F_1$(x, y). Here, these individual intensities are standardized with their respective peak values.

As apparent from FIG. 20, the erase light intensity is zero at its central portion, and the fluorescent intensity is also high at its central portion so that the fluorescent region is left only at the central portion. Although, the Rayligh-limit of the condensing optical system is 455 nm, it becomes 100 nm if the half value width of the fluorescent intensity $F_1(x, y)$ is defined as a spatial resolution capable of detecting the Rhodamine 6G, thereby exceeding the diffraction limit of the condensing optical system. In short, it is understood that the microscope body of the microscope system of this invention in the present example has an excellent super-resolution.

On the other hand, as the YAG laser employed as the light source for the pump light and erase light, an inexpensive, highly safe mode-locked type can be used. For example, the erase light can be produced by extracting a portion of the light of 2-nd harmonics of 523 nm, which is the pump light, by the beam splitter and then by converting the wavelength of the extracted portion to 560 nm by a nonlinear crystal such as a highly safe BBO crystal, or a wavelength modulating element such as the Raman shifter, or a nonlinear medium. Accordingly, the construction of the light source is remarkably simplified.

When the YAG laser is of the mode-locked type and also the semiconductor-laser-excited type, it is possible to produce a highly repetitive, short pulsed light of 100 MHz and some 10 psecs and to make a small-sized light source of a maintenance-free solid-state.

Moreover, the irradiation light may have a low intensity, and its wavelength is in the vicinity of 500 nm other than the optical absorption band of the biological specimen so that a damage on the biological specimen can be remarkably reduced.

Like the Rhodamine 6G, when 7-ethylamino-4-trifluoromethyl coumarin ($C_{12}H_{10}NO_2F_3$: Coumarin 500).is used, for example, the pump light and the era se light can be coped with the 2-nd harmonics and the 4-th harmonics of the YAG laser, as described hereinbefore, so that a spatial resolution of about 100 nm which is the same as that of the Rhodamine 6G can be achieved with the erase light intensity of 100 MW/cm$^2$.

Unlike the Rhodamine 6G or the 7-ethylamino-4-trifluoromethyl coumarin, when the molecule having the resonance wavelengths $\lambda 1$ and $\lambda 2$ which are not the wavelength formed by modulating the fundamental-wave and their harmonic-wave of the YAG laser with the simple nonlinear crystal, an oscillation frequency of the YAG laser can be operated in the range from the ultraviolet to the infrared waves by modulating with an optical system using a nonlinear crystal such as an optical parametric oscillator (OPO).

Because of the YAG laser, it is quite natural that dye need not be exchanged unlike the existing dye laser so that the operability of the microscope body is improved.

Example 2

In the foregoing Example 1 the condensed beam of the erase light has the phase distribution in which the phase changes continuously from 0 to $2\sigma$ when turned once around the optical axis. On the contrary, in the present Example 2, the condensed beam of the erase light has a discontinuously changing phase distribution.

Figure 21:
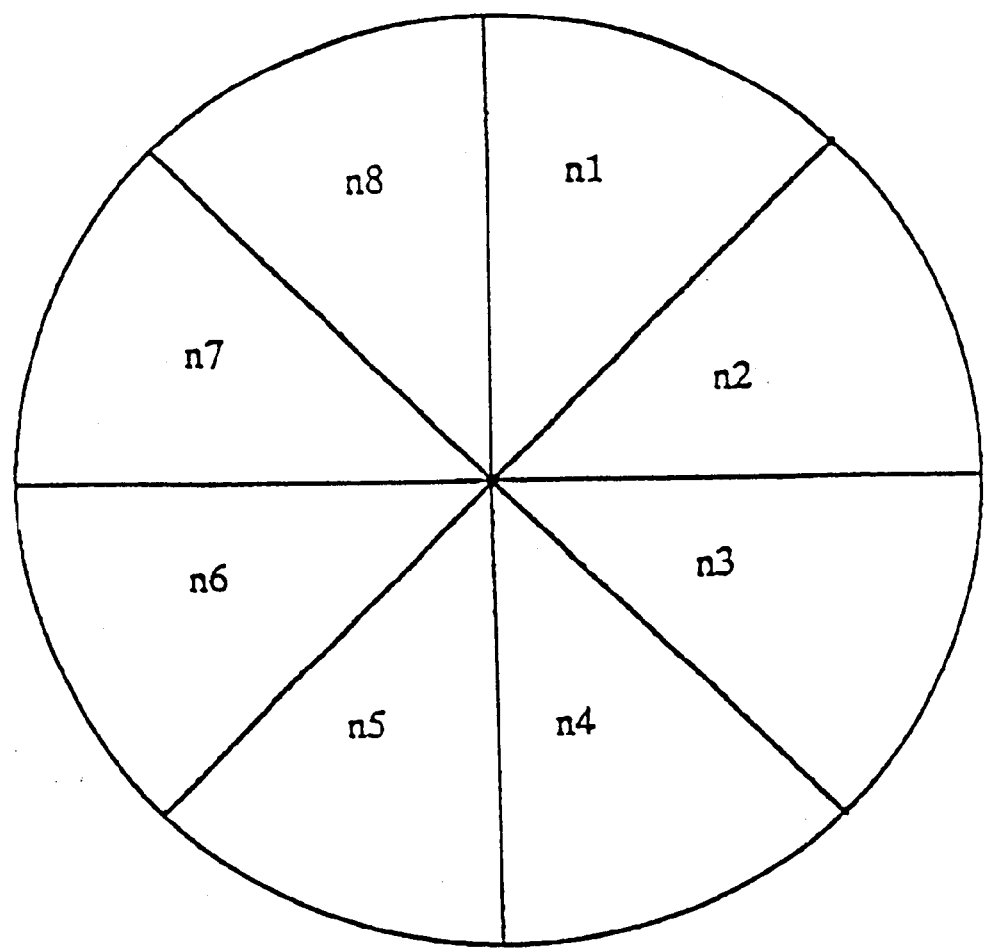
FIG. 21 is a conceptional diagram illustrating a phase plate having a refractive-index distribution changing discontinuously around an optical axis.

In order to give the discontinuously changing phase distribution to the condensed beam of the erase light, for example, there may be used a phase plate which has a refractive-index distribution (n1~n8).changing discontinuously around the optical axis, as illustrated in FIG. 21.

Figure 22:
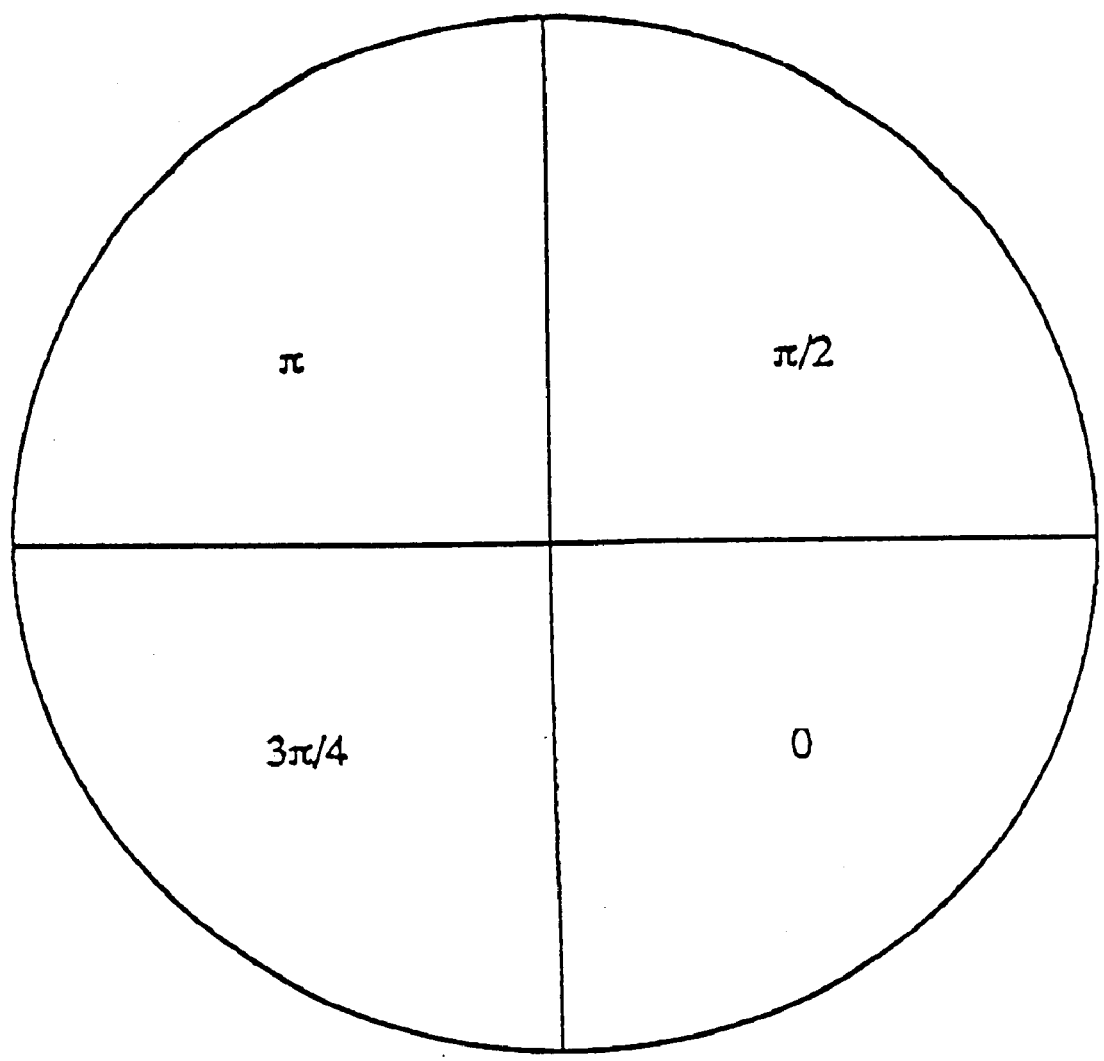
FIG. 22 is a conceptional diagram illustrating a phase distribution to be given to the erase light by a phase plate which has a refractive-index distribution being discontinuous by quartering the distribution around its optical axis.

Here, the intensity distribution of the condensed beam of the erase light and the intensity distribution of the fluorescence to be emitted are determined in the case where the fluorescence labeler molecule is the Rhodamine 6G and have the optical parameters and the environmental parameters as shown in the Table 1 and the Table 2, respectively, and the condensing optical system of the microscope body is provided with a phase plate having a refractive-index distribution which gives the condensed beam of the erase light a discontinuous phase distribution of discrete 0, $\pi/2$, $\pi$ and $3\pi/4$ quartered around the optical axis, as illustrated in FIG. 22.

FIGS. 23(a) and (b) show a top plan view and a side elevation illustrating a structure and an optical parameter of the phase plate, respectively.

This phase plate illustrated in FIGS. 23(a) and (b) is formed by coating a glass substrate (BK-7) with a magnesium fluoride film. This magnesium fluoride film has a refractive index of 1.38 at a wavelength of 560 nm so that it gives a phase difference of $\lambda/4$ for a film thickness of 350 nm. Therefore, the individual film thicknesses capable of a phase distribution of 0, $\pi/2$, $\pi$ and $(3\pi)/2$ in the individual quartered regions around the optical axis are 350 nm, 700 nm, 1,050 nm and 0 nm, respectively, as illustrated in FIG. 23(a).

The phase plate may be formed not only by making the coating of the optical thin film such as the magnesium fluoride film having such refractive-index distribution but also by etching the glass substrate directly to make an optical path difference giving the phases of the individual regions.

Here in the phase plate which is thus formed by coating the glass substrate with the optical thin film or by etching the glass substrate, the parallelism or roughness of the glass substrate has to be smaller than the optical path difference giving the phase difference of $\pi/4$, so as to prevent disturbance of the phase plane of the erase light.

In the phase plate using the magnesium fluoride film, more specifically, the disturbance in the optical path difference due to the parallelism or roughness of the glass substrate itself is set to 350 nm or less.

Figure 23:
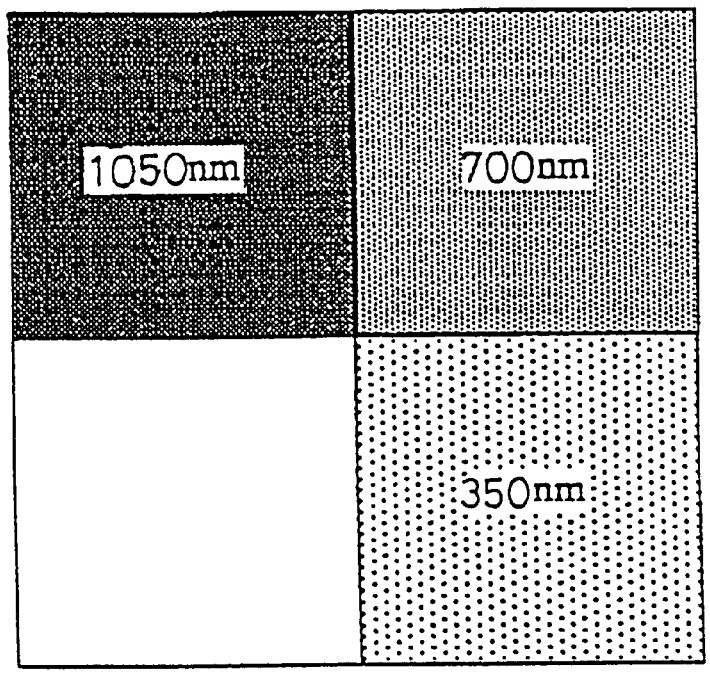
FIG. 23 presents, at (a) and (b), a top plan view and a side elevation illustrating a structure and an optical parameter of the phase plate, respectively.
Figure 23:
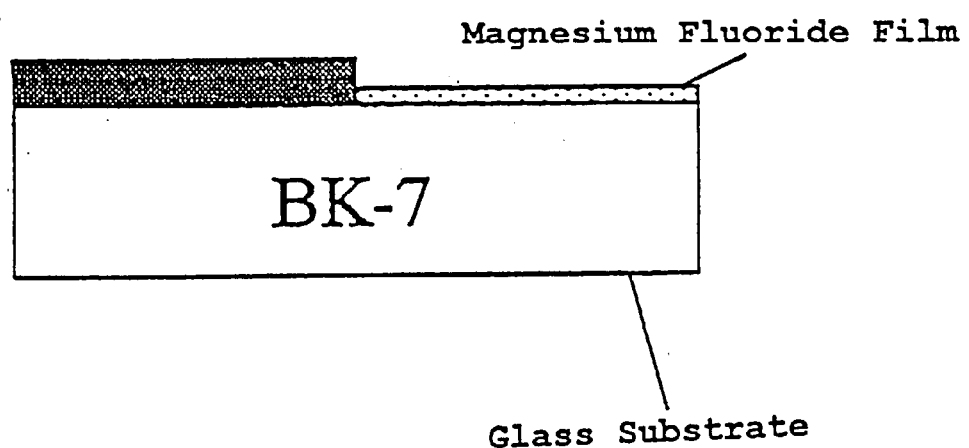
Figure 24:
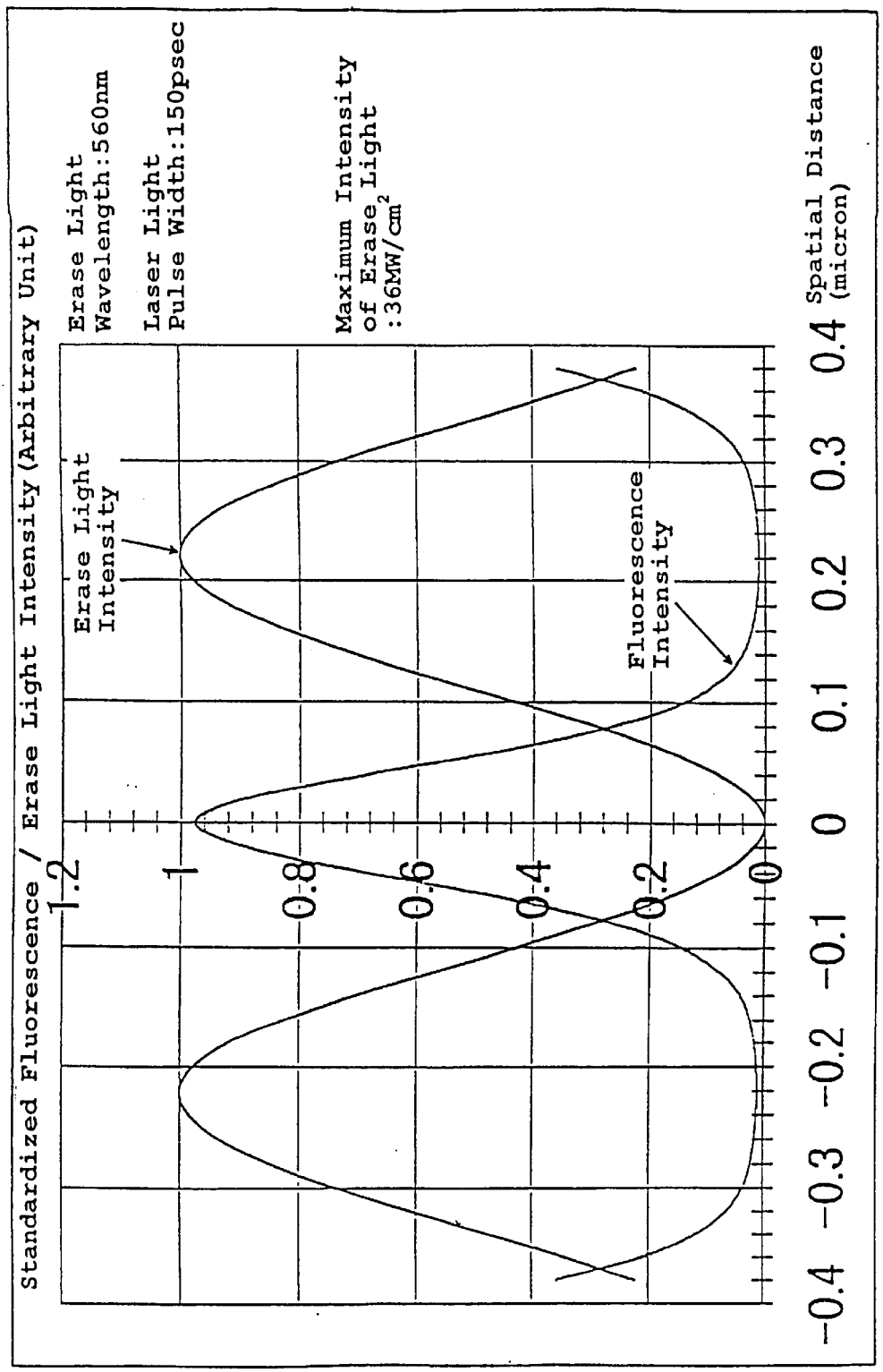
FIG. 24 is a diagram illustrating one example of an erase light condensed beam intensity and a fluorescent intensity in the microscope body of a microscope system of this invention of Example 2.

FIG. 24 illustrates the condensed beam intensity of the erase light, as condensed by the condensing optical system provided with the phase plate of FIG. 23, and the fluorescent intensity.

It is apparent from FIG. 24 that the condensed beam intensity of the erase light takes a shape similar to that of the condensed beam intensity of the erase light illustrated in FIG. 20 of the Example 1, the optical intensity being zero at the central portion.

In other words, an excellent super-resolution is realized even when the condensed beam of the erase light has the phase distribution changing discontinuously around the optical axis.

In addition, it is far simpler to make a phase plate such as a magnesium fluoride film, for example to have a refractive-index distribution or an optical-path-difference distribution changing discontinuously around the optical axis than to make a phase plate to have that changing continuously.

Example 3

For the microscope system of this invention, it is the most desirable that the beam obtained by condensing the erase light that is the light of the wavelength $\lambda 2$ be the 1-st-order-Bessel-beam that is a nondiffractive beam. However, in order to give the microscope body a theoretical super-resolution, the beam may have the aforementioned shape in which the intensity at the central portion is zero.

Therefore, the beam having a phase modulated by the phase plate, as exemplified in FIG. 18 or 22, may be focused in a reduced scale by the ordinary condensing optical system, i.e., the condensing optical system not having the zonal optical system as in the Example 1. Then, although nondiffraction disappears, an excellent super-resolution can be realized.

Figure 25:
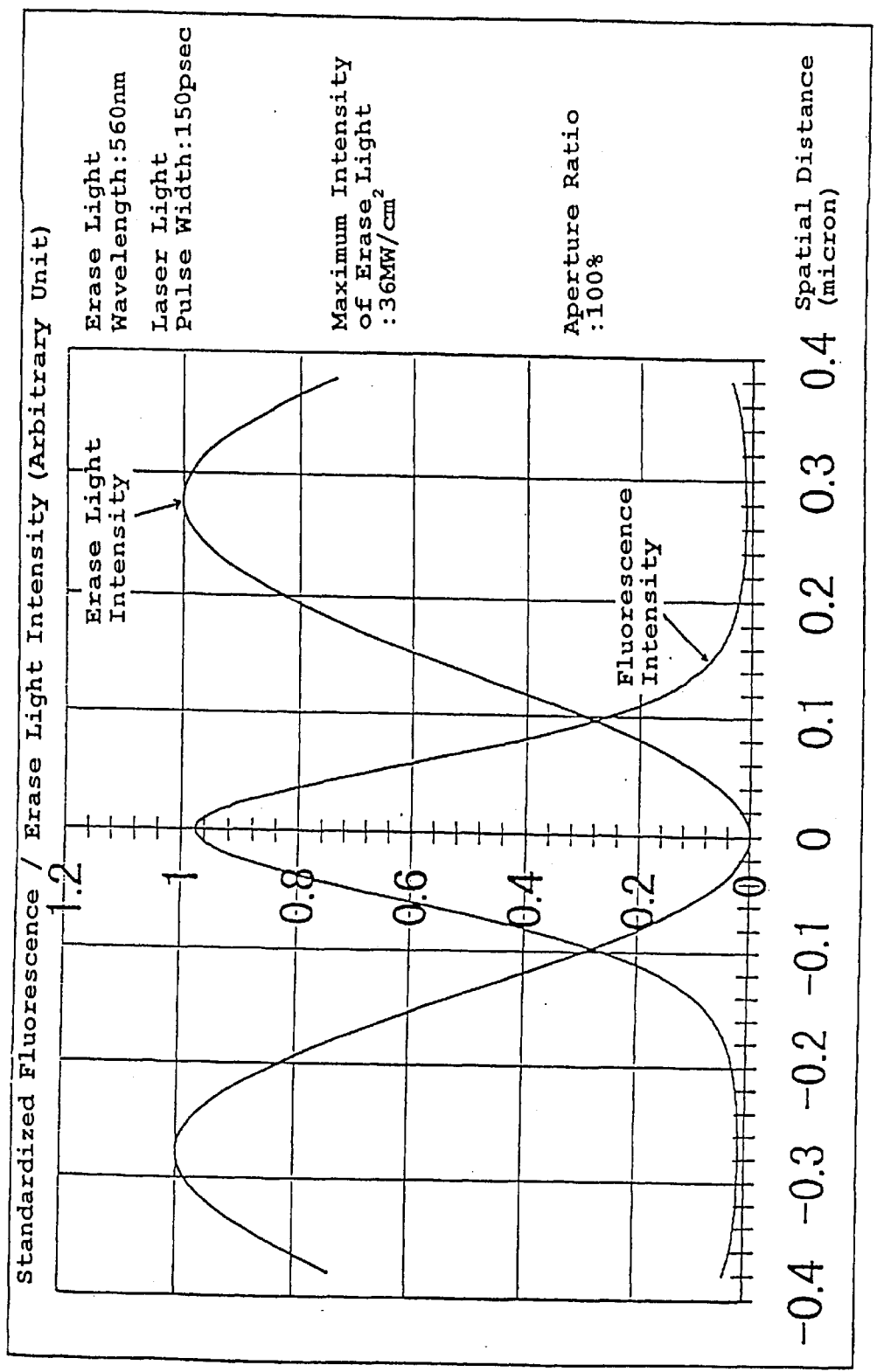
FIG. 25 is a diagram illustrating one example of an erase light condensed beam intensity and a fluorescent intensity in the microscope body of a microscope system of this invention of Example 3.

FIG. 25 illustrates an intensity distribution of a condensed beam of an erase light and a fluorescent intensity distribution, which are calculated when the specimen is dyed with the rhodamine 6G and the shading ratio of the pupil is 0 and the optical parameters and the environmental parameters a takes the values of the Table 1 and the Table 2, respectively.

It is apparent from FIG. 25 that the beam condensed by the ordinary condensing optical system having the phase plate is shaped to have a zero intensity at its central portion, thereby leaving the fluorescent region at its central portion. The Raileigh-limit of the condensing optical system is 455 nm but becomes 200 nm exceeding the diffraction limit of the condensing optical system if the half value width of the fluorescent intensity $F_1(x, y)$ is the spatial resolution capable of detecting the Rhodamine 6G. It is, therefore, understood that an excellent super-resolution is achieved.

Example 4

Figure 26:
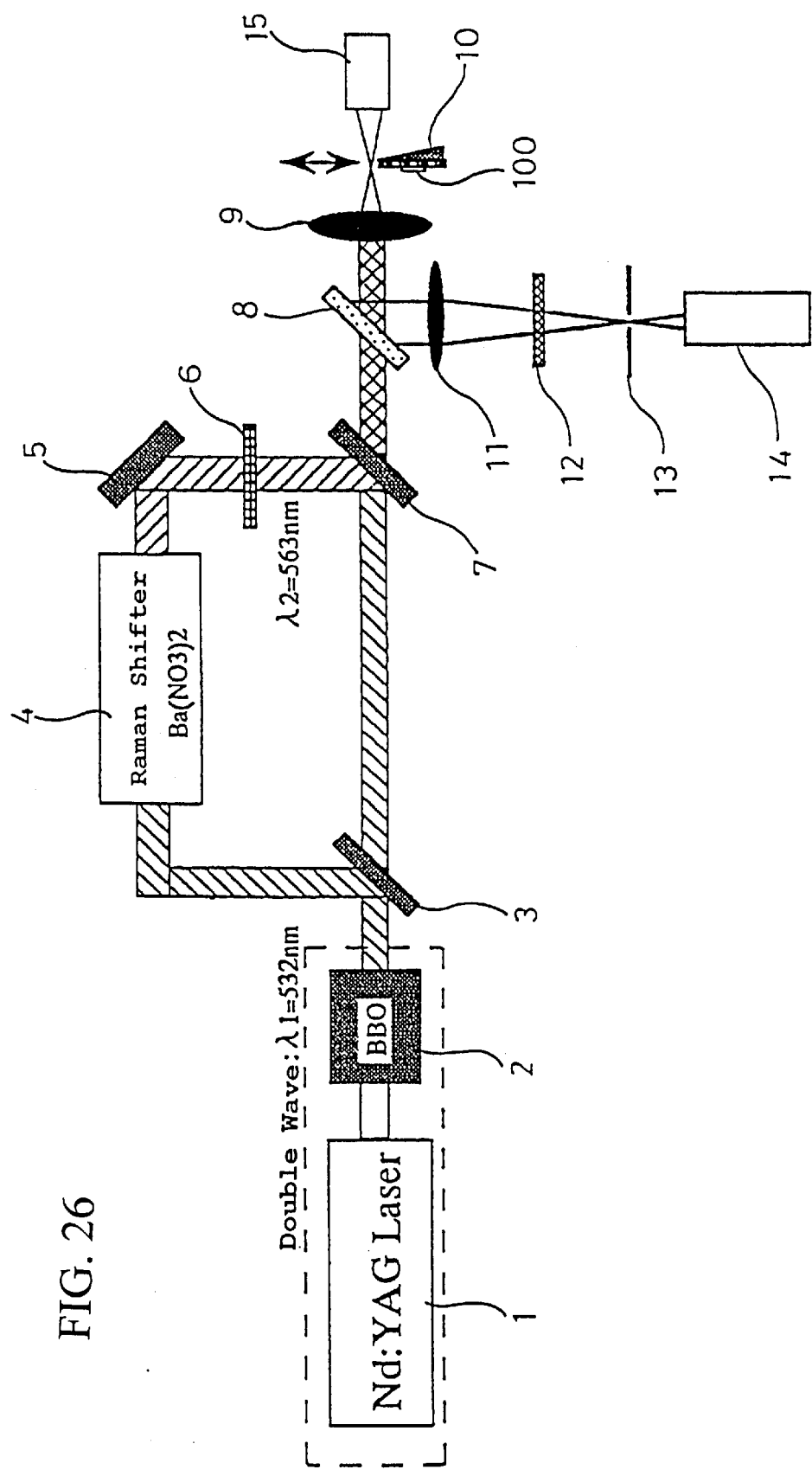
FIG. 26 is a construction diagram showing an essential portion of one example of the microscope system of this invention.

FIG. 26 illustrates one example of the microscope system of this invention having a super-resolution microscope function.

In this microscope system illustrated in FIG. 26, an adjusted specimen (100) is dyed with the Rhodamine 6G used as the fluorescence labeler molecule.

There are provided a mode-locked type Nd:YAG laser (1) as the light sources for the pump light which is the light of the wavelength λ1 and the erase light which is the light of the wavelength λ2 and a BBO crystal (2).which is a nonlinear crystal as the nonlinear medium for their wavelength conversions. The fundamental-wave of the Nd:YAG laser (1) is subjected to a wavelength conversion with the BBO crystal (2), thereby oscillating the 2-nd-harmonics of 532 nm as the pump light.

On the optical path of this pump light, there is provided a half mirror (3), by which a portion of the 2-nd harmonics, i.e., the pump light is extracted and subjected to a wavelength conversion to 563 nm by a Raman shifter (4) made of a $Ba(NO_3)_2$ crystal as the nonlinear crystal thereby to produce the erase light.

This erase light irradiates a phase plate (6) of the Example 2 through a mirror (5) so that it is formed by the phase plate (6) into a hollow beam having a zero field intensity at its central portion.

The erase light and the pump light thus formed as the hollow beam are caused by a dichroic mirror (7) to follow the same optical path and are condensed through a next dichroic mirror (8) and a condensing objective lens (9) on the adjusted specimen (100) which is carried on a two-dimensional carriage stage (10) moving in the arrow direction as shown.

By the irradiations of the pump light and the erase light thus condensed, the fluorescence emitted from the adjusted specimen (100) is reflected by the dichroic mirror (8) and is condensed on a photomultiplier (14) by a fluorescence condenser lens (11) through a sharp cut filter (12) and a pin hole (13).

The dichroic mirror (8) is an interference filter capable of transmitting the pump light and the erase light and having a reflectivity in the fluorescent band. As a result, the pump light and the erase light can be separated from the fluorescence that is a signal light.

The sharp cut filter (12) arranged between the dichroic mirror (8) and the photomultiplier (14) is a band-pass filter for cutting the pump light and the erase light which are moved by surface scatter of the dichroic mirror (8) and the like, and the pin hole (13) functions as a spatial filter for cutting the stray light which is spatially diffused. By these sharp cut filter (12) and pin hole (13), the detection sensitivity of the fluorescence and the S/N ratio are improved.

In this microscope system of this invention, the intensity of the fluorescence can be monitored while moving the two-dimensional carriage stage (10) synchronously with the timing of irradiation of the pulse light of the Nd:YAG laser, thereby to produce a two-dimensional fluorescent image of the adjusted specimen (100).

Here, the intensities of the pump light and the erase light are monitored by a photomultiplier (15) so that the fluctuation of the graphic signal for each pixel due to the intensity conversion of the laser beam can be inhibited by adding the signal processing thereby to improve the image quality.

In this example shown in FIG. 26, each component can certainly be modified in various manners and another function can be added.

For example, if the ordinary optical lens is used as the condensing objective lens (9), it is possible to form a condensed beam of the erase light having a zero intensity at the center of the condensed point. Further, if the condensing objective lens (9) gives a boundary condition symmetric around the optical axis, it is possible to form a 1-st-order-Bessel-beam that is a nondiffractive beam.

Hereinafter, examples of an optical system as the condensing objective lens (9) capable of forming an 1-st-order-Bessel-beam are described.

(I) Zonal Optical System

Figure 27:
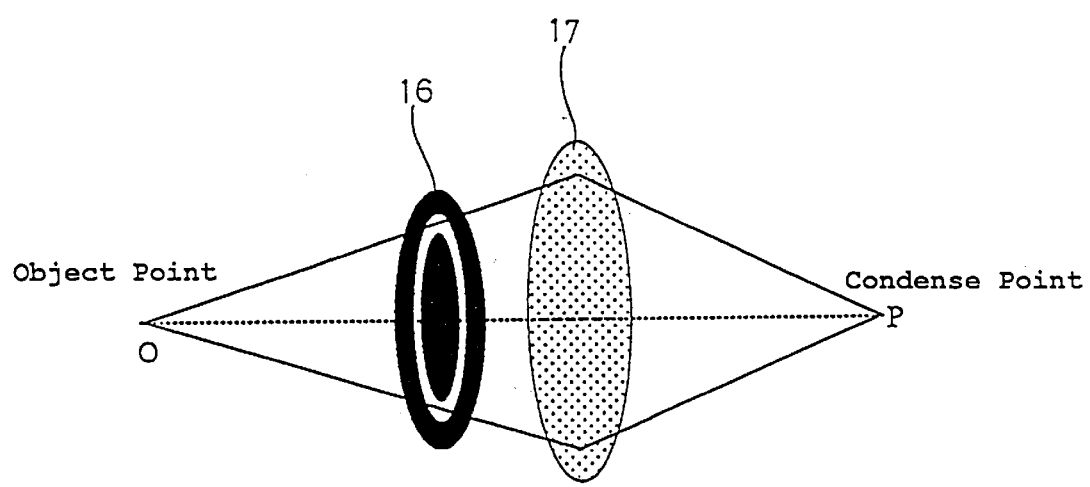
FIG. 27 is a diagram showing one example of a zonal optical system in which an annular zonal slit and an ordinary glass lens are combined.

This zonal optical system may be exemplified by combining an annular zonal slit (16) and an ordinary glass lens (17), as illustrated in FIG. 27. When the annular zonal slit (16) is employed for example, it is desireble to place the etalon(not-shown).in front of the zonal slit (16), thereby to increase the quantity of light passing therethrough by its one-dimensional diffractive light.

Figure 28:
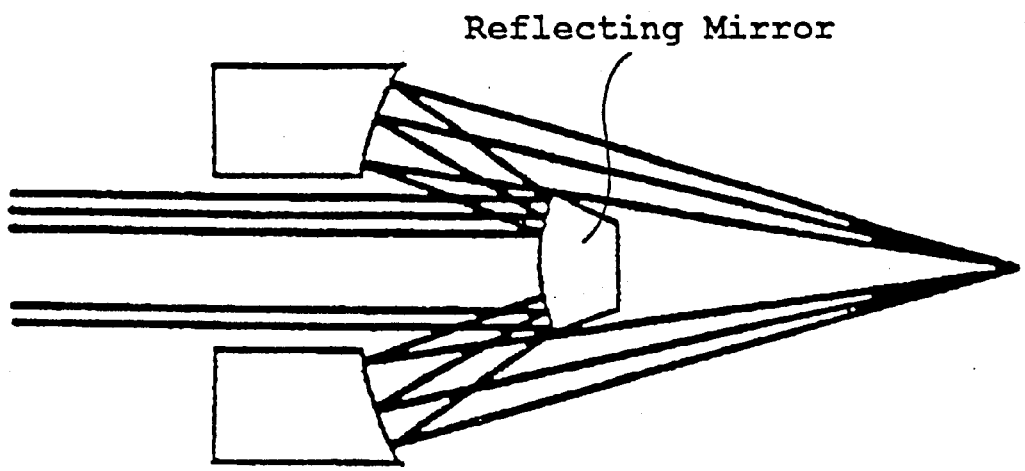
FIG. 28 is a diagram illustrating a reflecting type objective lens as one example of the zonal optical system.
Figure 29:
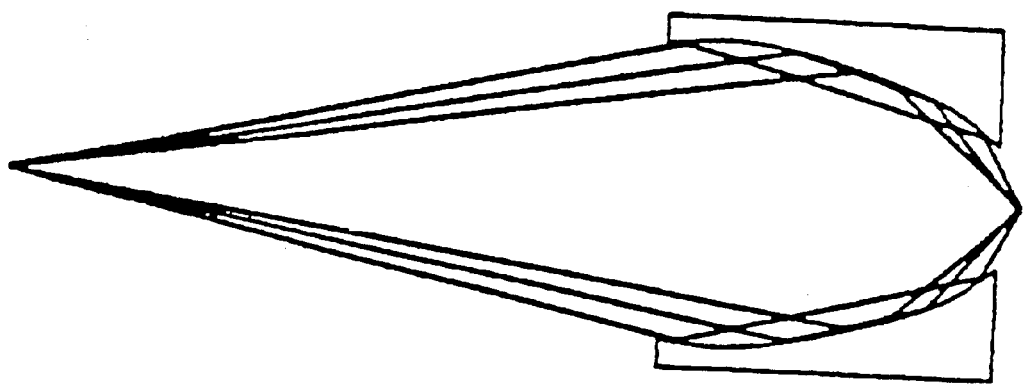
FIG. 29 is a diagram illustrating a Walter type lens as one example of the zonal optical system.

On the other hand, there is a zonal optical system intrinsically equipped with a zonal-pupil, which has a boundary condition necessary for forming the 1-st-order-Bessel-beam. This zonal optical system may be exemplified by a reflecting objective lens illustrated in FIG. 28. This reflecting objective lens of FIG. 28 is the Cassegrain or Schwaltshild type optical system, in which a convex reflecting mirror placed inside shades the central portion of the optical pupil so that it substantially plays a role similar to that of the aforementioned annular zonal slit (16). The reflecting type optical system is also exemplified by a Walter lens of the oblique-incident type, as illustrated in FIG. 29. This Walter lens is an extreme zonal optical system and is equivalent to the use of a substantially ideal annular zonal slit.

(II) Diffractive Optical System

An axially symmetric diffractive optical system (including the transmission type and the reflection type) gives a boundary condition symmetric around the optical axis to the aforementioned wave equation 12 so that it can be applied as the condensing optical system.

Figure 30:
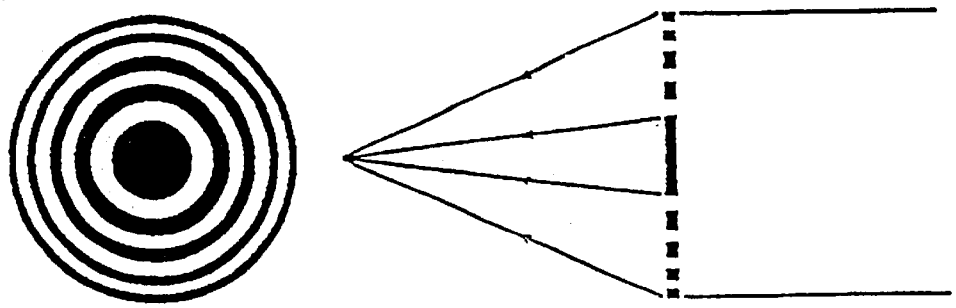
FIGS. 30 presents, at (a) and (b), transmission type and reflection type Fresnel zone plates as examples of diffracting optical systems, respectively.
Figure 30:
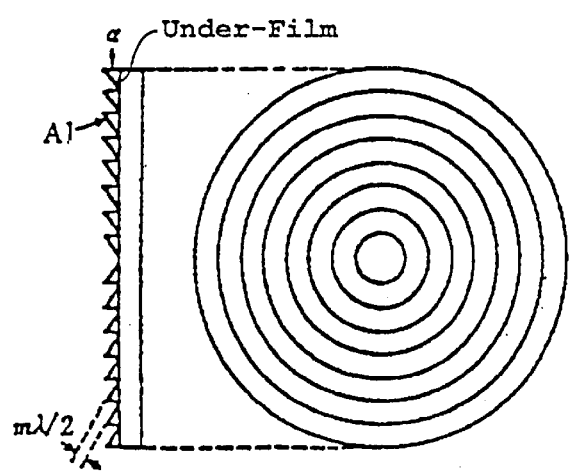

This diffractive optical system may be exemplified by a Fresnel zone plate. FIGS. 30(*a*) and 30(*b*), respectively, illustrates transmission-type Fresnel zone plate and a reflection-type Fresnel zone plate. Since the Fresnel zone plate intrinsically has a focusing ability, it has both a condensing ability and a boundary condition necessary for forming the 1-st-order-Bessel-beam.

Figure 31:
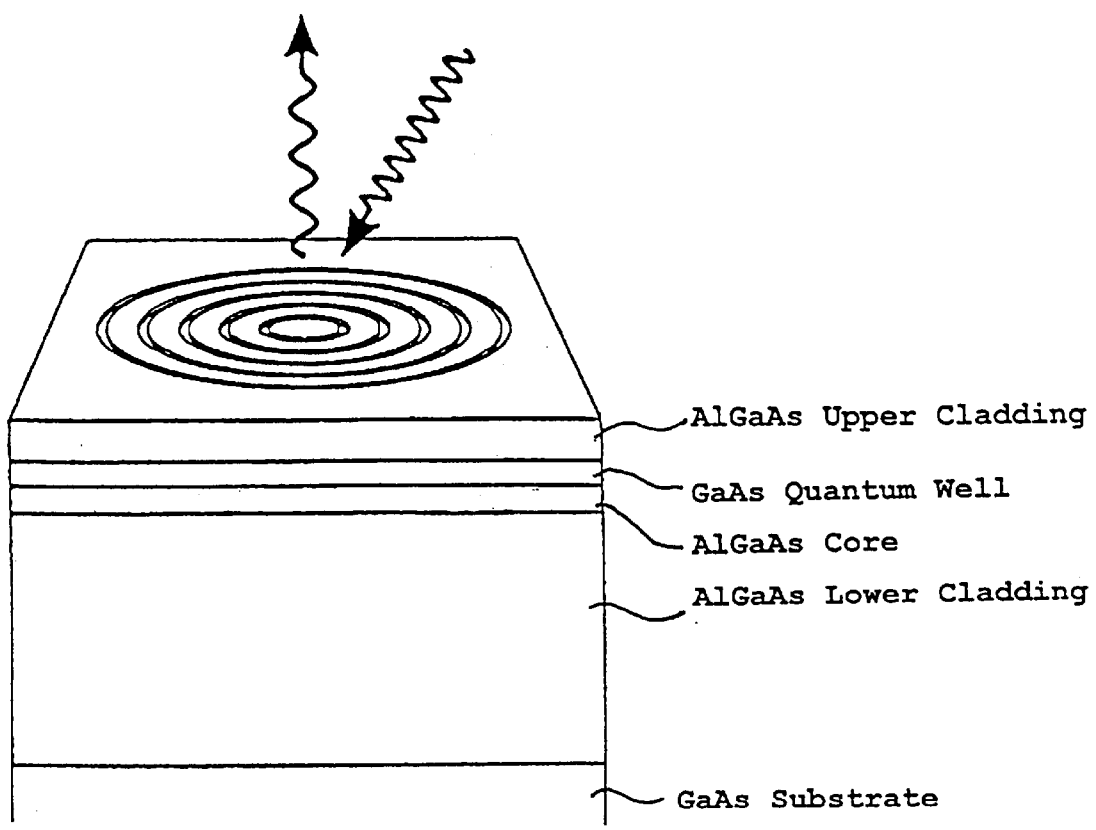
FIG. 31 is a diagram illustrating the transmission diffraction grating having grooves in concentric circles.

When it is intended to give only the boundary condition, on the other hand, there may be provided a diffraction grating which has grooves or spiral grooves in concentric circles, as illustrated in FIG. 31.

(III) Axicon

Figure 32:
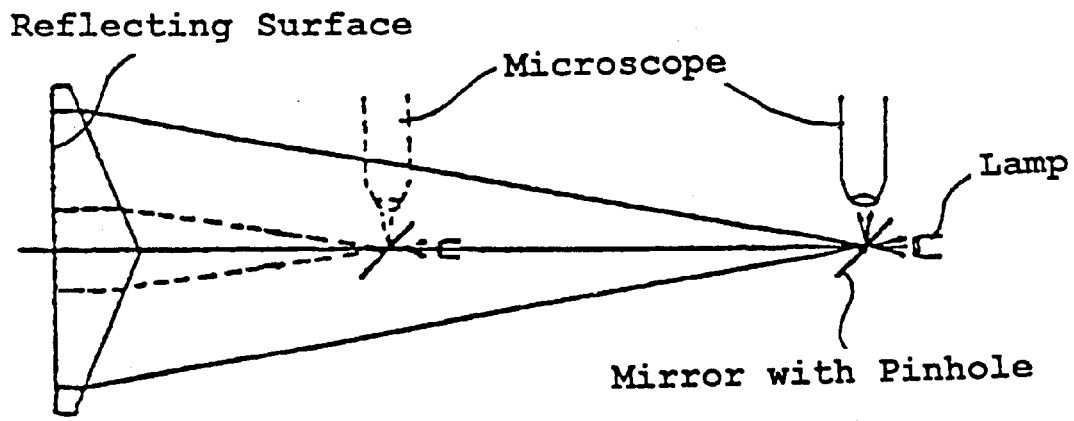
FIG. 32 is a diagram illustrating one example of an axicon optical system.

This axicon is also an axially symmetric 6optical system capable of focusing a-point light source on an axis over a wide range on the axis. FIG. 32 illustrates one example of the axicon. This axicon exemplified in FIG. 32 is a reflecting lens called the "McLeod" which has a conical surface and a plated flat surface. In this axicon, for a point on an axis within a predetermined range, there exists an identical point on the axis, and, for a point out of an axis, there exists an image point at a point symmetric with that point. This axicon also gives a boundary condition symmetric to the optical axis.

The optical system thus far described can be provided as the condensing objective lens (9).

In the example shown in FIG. 26, on the other hand, there may be provided as the fluorescence detector not only a photoelectron multiplier such as the photomultiplier (14) (15) but also a semiconductor detector such as a PIN photodiode or a CCD.

When the Rhodamine 6G is used as the fluorescence labeler molecule, another means for the light source can be employed. For example, in order to produce the erase light, the Raman shifter (4) can be replaced by an OPO or a dye laser. In this case, the erase light has a variable wavelength, so that the rhodamine group molecule such as Rhodamine 110 can be used as the labeler molecule.

Moreover, in the microscope system of FIG. 26, in order to produce a two-dimensional fluorescent image of the adjusted specimen (100), the two-dimensional carriage stage (10) is capable of moving two-dimensionally with respect to the condensing beam. In addition, as in the laser scanning type microscope of the prior art, for example, the optical system can be vibrated directly with a galvan-mirror and the like, thereby making it possible to scan the adjusted specimen (100) two-dimensionally with the beam.

Example 5

Figure 33:
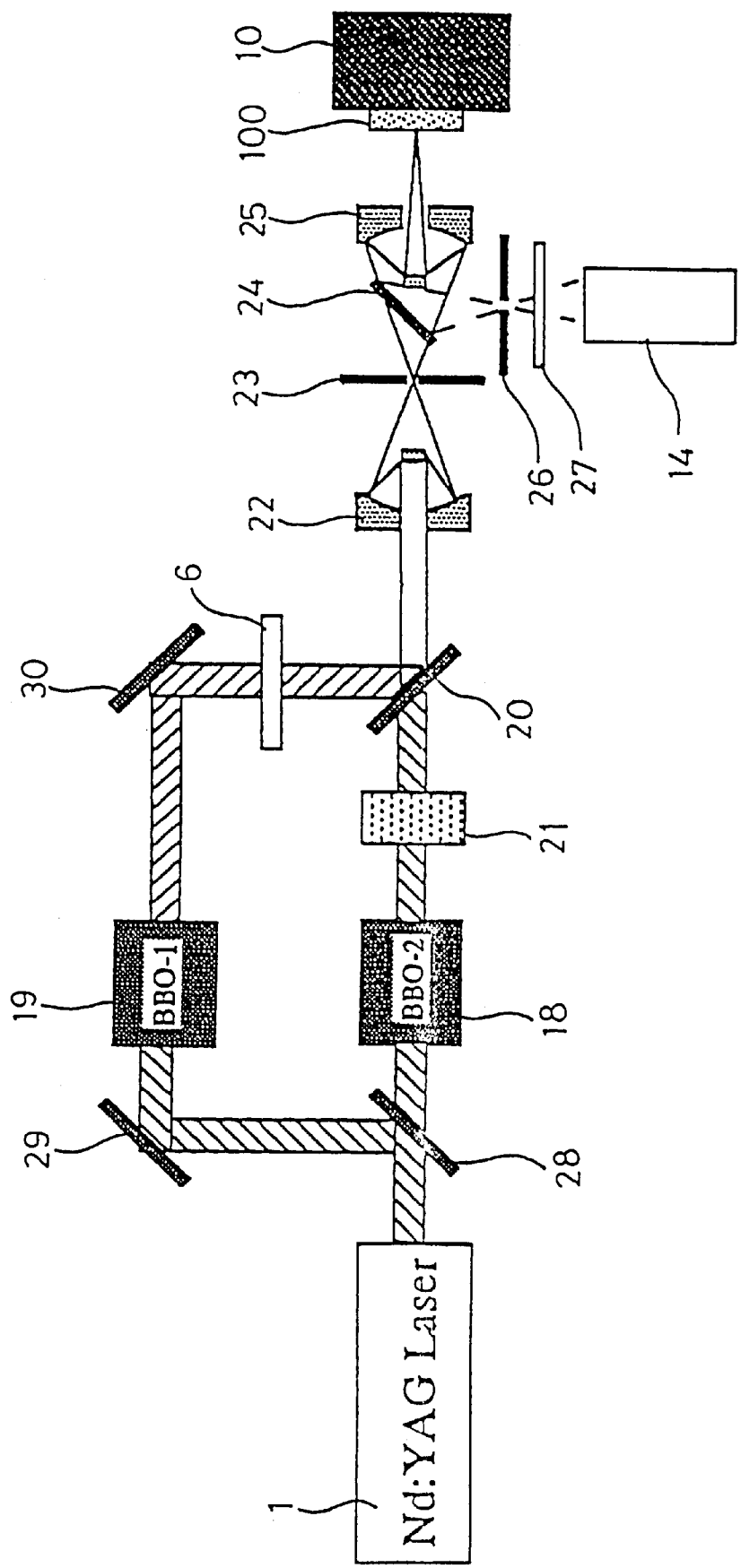
FIG. 33 is a construction diagram showing an essential portion of another example of the microscope system of this invention.

FIG. 33 illustrates one example of the microscope system of this invention having a confocal type super-resolution microscope function.

In this microscope system of FIG. 33, the adjusted specimen (100) is dyed with the Coumarin 500.

As the light sources for the pump light and the erase light, there is provided the mode-locked type Nd:YAG laser (1), and the fundamental-wave (1,064 nm).of this Nd:YAG laser (1) is diverged by a half mirror (28).

The fundamental-wave of one path is subjected to a wavelength conversion to 355 nm by a 3-rd harmonics generator (18) made of BBO-1 crystal, thereby making it into the pump light. The fundamental-wave of another path is introduced through a mirror (29) into a 2-nd harmonics generator. (19) made of BBO-2 crystal, by which it is subjected to a wavelength conversion to 532 nm, thereby making it into the erase light.

The erase light is guided by a mirror (30) to irradiate a phase plate (31), as exemplified in the Example 2, by which it is shaped to have a zero field intensity at its central portion.

Then, the erase light thus shaped into the hollow beam and the pump light are guided to follow the same optical path by a dichroic mirror (20).

Between the dichroic mirror (20) and the 3-rd harmonics generator (18), there is arranged a polarizer (21), by which the polarizing plane of the pump light can be freely rotated.

The pump light and the erase light, as arranged to have their optical paths on the common axis by the dichroic mirror (20), are guided to illuminate a pin hole (23) by a condenser lens (22) which is the Schwaltshild type reflecting optical system.

The image of the pin hole (23) illuminated with the condensed pump light and erase light is employed as the light source for forming a micro beam.

The pump light and erase light having passed through the pin hole (23) penetrate a dichroic mirror (24) and then are condensed by an objective lens (25) which is the Schwaltshild type reflecting optical system on the adjusted specimen (100) placed on the two-dimensional carriage stage (10).

The condenser lens (22) and the objective lens (25), i.e., the Schwaltshild type reflecting optical system have each mirror surface coated with a metal film such as aluminum and can focus a light of a wide wavelength range from infrared to ultraviolet without any chromatic aberration. As a result, they can focus the pump light and the erase light having different wavelengths on the adjusted specimen (100) in absolutely the same focusing performance and high resolution. This Schwaltshild type reflecting optical system is a zonal optical system and gives a boundary condition necessary for forming the 1-st-order-Bessel-beam when a shading ratio $\rho_0$ falls within a range from 0 to 1 by adjusting radius of its convex mirror placed inside The fluorescence emitted from the adjusted specimen (100) by irradiation of the condensed pump light and erase light It condensed is reflected through the objective lens (25) by the dichroic mirror (24). At this time, the scattered light and the stray light of the pump light and the erase light are not reflected by the dichroic mirror (24) so that only the fluorescent light that is the signal light can be separated.

Then, the fluorescent light reflected by the dichroic mirror (24) passes through a pin hole (26), and after the afterglows of the pump light and the erase light are cut by a sharp cut filter (27), it is condensed on the receiving surface of the photomultiplier (14).

This optical system of the microscope body in the microscope system of this invention, as illustrated in FIG. 33, is a confocal optical system, in which the pin holes (23) and (26) are located optically at the confocal position with the condensing point on the adjusted specimen (100) being a center. Hence, like the scanning-laser fluorescent microscope having a similar confocal optical system, it is possible to achieve an excellent S/N ratio and further, by the movement of the two-dimensional carriage stage (10) indirection of the optical axis, to produce a three-dimensional fluorescent image of the adjusted specimen (100) can be produced in an excellent S/N ratio.

In addition, by the polarizer (21), a new useful function is added to the super-resolution function. Generally, a molecule has an intense absorption for an electric vector in a specific direction, and the benzene derivative or the purine derivative, for example, absorbs a light having an electric vector in the same direction as the planar direction of the molecule plane. In this case, by turning the polarization direction of the pump light, it is possible to excite only the molecule spatially oriented in a specific direction, thereby to establish fluorescence. As a result, by taking a fluorescent image while changing the polarization direction of the pump light by the polarizer (21), spatial orientation characteristics of a specific molecule or structures of the adjusted specimen (100) can be analyzed.

Example 6

Figure 34:
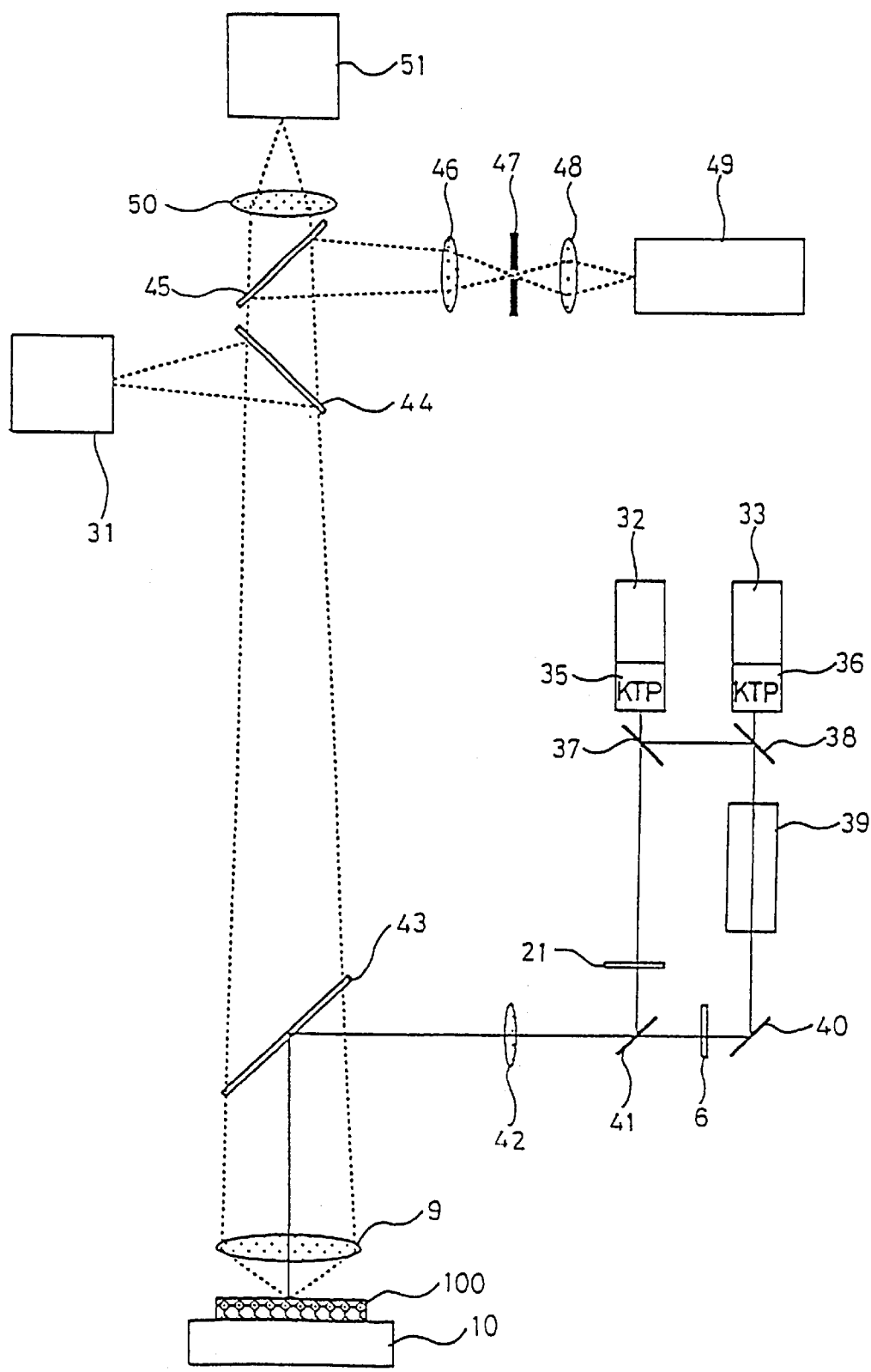
FIG. 34 is a construction diagram showing an essential portion of another example of the microscope system of this invention.

FIG. 34 illustrates another example of the microscope system of this invention.

The microscope system of FIG. 34 has not only the super-microscope function but also a micro-manipulator function using a hollow micro beam. The microscope system further has the ordinary fluorescent microscope function so that it can always monitor the fluorescent image from the adjusted specimen (100) on the real time without any laser scanning.

In this microscope system of FIG. 34, the adjusted specimen (100) is dyed with the Rhodamine 6G.

As a light source for the pump light and the erase light for the super-resolution microscope function and as a nonlinear medium for wavelength conversion, there are provided a mode-locked type Nd:YAG laser (32) and a KTP crystal (35) or the nonlinear crystal, respectively. As a laser light source for forming a hollow micro beam for the micro manipulator function and as a nonlinear medium for wavelength conversion, there are provided a Nd:YAG laser (33) of continuous oscillation CW and axiconTP crystal (36), respectively. Further, as a light source for the ordinary fluorescent microscope function, there is provided a mercury lamp (31).

First, here will be described the super-resolution microscope function.

The fundamental-wave of the Nd:YAG laser (32) are subjected to the wavelength conversion by the KTP crystal (35), so that the 2-nd harmonics of 532 nm are oscillated as the pump light. Part of this pump light is extracted by a half mirror (37) to go through a mirror (38) into a Raman shifter (39) made of $Ba(NO_3)$ crystal, then its wavelength is changed to 563 nm by the Raman shifter (39), thereby to produce the erase light.

Its The erase light goes into a dichroic mirror (40), by which the 2-nd harmonics of 532 nm having contaminated are removed, so that the only the light of 563 nm is extracted in a high purity.

This erase light is further shaped into the hollow beam having a zero field intensity at its central portion by the phase plate (6), such as the one exemplified in the Example 2.

These erase light and pump light thus shaped into the hollow beam are caused to pass through the same optical path by a dichroic mirror (41).

Between the half mirror (37) and the dichroic mirror (41), there is arranged the polarizer (21), by which the polarizing plane of the pump light can be freely rotated.

The pump light and the erase light, as arranged to have their optical paths on the common axis by the dichroic mirror (41), are shaped by a relay lens (42) and are reflected by a half mirror (43) to go into the objective lens (9), by which they are condensed on the adjusted specimen (100) carried on the two-dimensional carriage stage (10).

The fluorescence emitted from the adjusted specimen (100) by the irradiations of the pump light and the erase light passes through the half mirror (43) and a half mirror (44) and is reflected in a direction to go into a lens (46) by a half mirror (45). Then, the fluorescence is condensed at the center of a pin hole (47) by the lens (46) and goes through a lens (48) into a spectrometer (49).

The pin hole (47) functions as a spatial filter and plays a role to enhance S/N ratio for the measurements by cutting, for example, the fluorescence which is emitted from such as an optical system, other than the adjusted specimen (100).

In this example shown in FIG. 34, on the other hand, a spectrometer (49) is provided as a fluorescence detector thereby to make it possible not only to measure fluorescent intensity but also to observe fluorescence spectrum and measure time response to laser irradiation thereby to analyze chemical structure or composition of the adjusted specimen (100). Moreover, spatial orientation data of the composition can be obtained by changing the polarization planes of the pump light and the erase light relatively by the polarizer (7).

Thus, there is achieved a remarkably excellent super-resolution microscope function capable of making various measurements and analyses for the adjusted specimen (100).

Next, the micro manipulation function will be described.

When particles are to be captured in the micro manipulation, it is basically necessary to use a continuously oscillating light source. For this necessity, the Nd:YAG laser (33) of CW is provided as the continuously oscillating light source.

The fundamental-wave of this Nd:YAG laser (33) are subjected to a wavelength conversion by the KTP crystal (36) to produce 2-nd harmonics of 532 nm. The 2-nd harmonics are employed as a light source for generating the hollow micro beam to be used for the micro manipulation.

The 2-nd harmonics having passed through the half mirror (38) are subjected to a wavelength conversion to 563 nm by the Raman shifter (39), and the 2-nd harmonics of 532 nm having contaminated are removed by the dichroic mirror (40), so that only the light of 563 nm is extracted with high purity.

This light of 563 nm is shaped by the phase plate (6) to the hollow micro beam having a zero field intensity at its central portion, and passes through the dichroic mirror (41) and the relay lens (42), and is reflected by the half mirror (43) to go into the condensing objective lens (9), by which it is condensed on the adjusted specimen (100).

Thus, the hollow micro beam of 563 nm for the micro manipulation can employ the same optical system as the aforementioned one for the erase light for the super-resolution function.

Although the micro manipulation of the prior art, as called the "optical pincette", can only move a single particle, this micro manipulation using the hollow micro beam can confine a plurality of particles in the hollow micro beam and can function as the "optical pipette" for a high grade micro manipulation. Of course, the laser intensity can be a remarkably low level thus the damage on the specimen can be lowered.

The micro manipulation is performed while monitoring the entire microscope image. Thus, there is added the ordinary fluorescent microscope function for monitoring the microscope image.

As the light source for this fluorescent microscope function, there is provided the mercury lamp (31), and the light therefrom is guided through the half mirrors (44) and (43) and the condensing objective lens (9) to irradiate the adjusted specimen (100). Then, the fluorescent image emitted by that light irradiation is guided again through the condensing objective lens (9), and the half mirrors (43) and (44) to go into a CCD cameral focusing lens (50), by which it is directly focused on the receiving surface of a CCD camera (51). This fluorescent image can be directly monitored at any time on the CRT.

Accordingly, while monitoring the fluorescent image on the CRT, particles such as red blood cells can be micromanipulated at a high grade.

Example 7

In the microscope system of this invention, in order to give an excellent super-resolution and operability to its microscope body, its is desirable that the beam obtained by condensing the erase light be the 1-st-order-Bessel-beam.

The 1-st-order-Bessel-beam can be formed by using the zonal optical system, the diffractive optical system and the axicon, or the phase plate of the condensing optical system, as described hereinbefore. In addition, by giving the boundary condition necessary for forming the 1-st-order-Bessel-beam into the resonator of a gas laser, a sold laser or a semiconductor laser of the light source for the erase light, it is possible to make the erase light itself into the 1-st-order-Bessel-beam.

Figure 35:
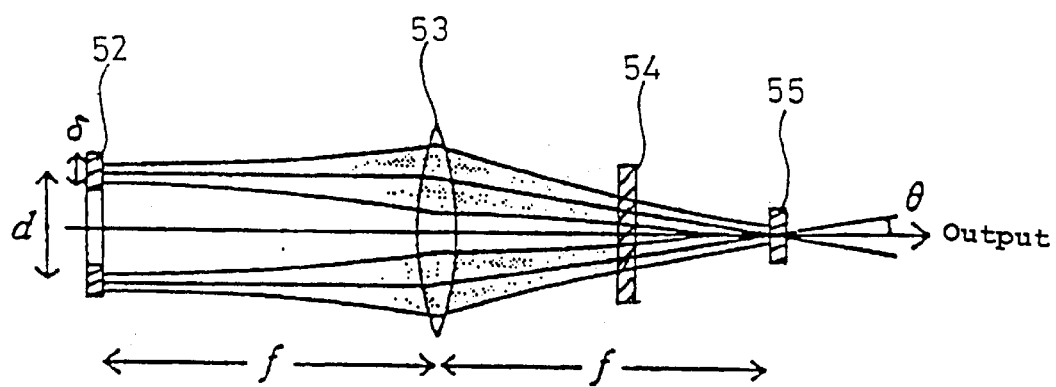
FIG. 35 is a construction diagram showing an essential portion of one example of a laser resonator capable of oscillating a primary Bessel beam directly.

FIG. 35 illustrates one example of a laser resonator provided with the boundary condition.

This laser resonator illustrated in FIG. 35 is provided with a lens (53) having an ordinary focal distance f, a phase plate (54) and an output mirror (55) and further with a ring-shaped zonal mirror (52) as a resonator mirror on the end face.

The 1-st-order-Bessel-beam can be directly produced by giving the boundary condition axially symmetric with respect to the beam optical axis in the ring-shaped zonal mirror (52) and by placing in the laser resonator the phase plate which gives the beam the phase difference in which the electric fields axially symmetric with respect to the electric field of the plane normal to the optical axis are shifted by $\pi$ from each other.

By placing such ring-shaped zonal mirror (52) or phase plate in the laser resonator to give the boundary condition, the structure of the condensing optical system of the microscope body can be simplified, thereby remarkably simplifing its alignment or the like.

Figure 36:
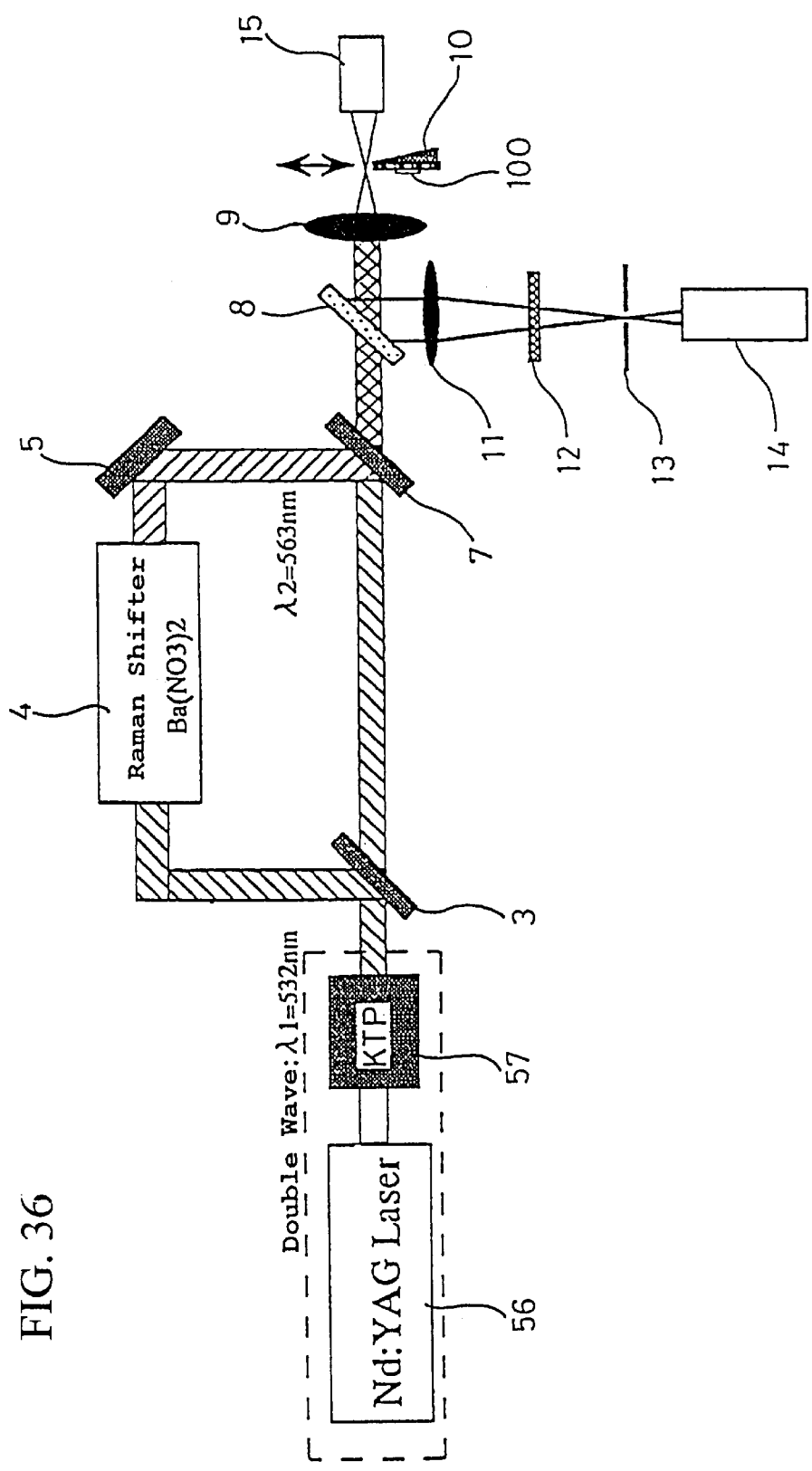
FIG. 36 is a construction diagram showing an essential portion of one example of the microscope system of this invention of the case in which a Nd:YAG laser has the laser resonator shown in FIG. 35.
Figure 37:
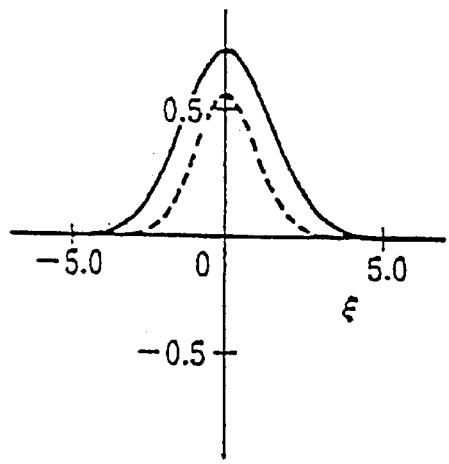
FIG. 37 presents, at (a), (b), (c), and (d), diagrams illustrating amplitude distributions and intensity distributions on beams of higher orders for n=0, n=1, n=2, and n=3, respectively.
Figure 37:
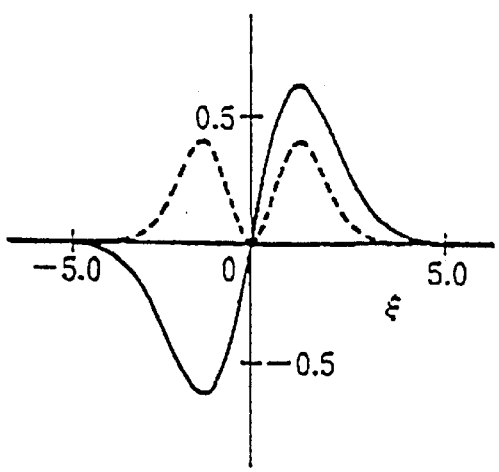
Figure 37:
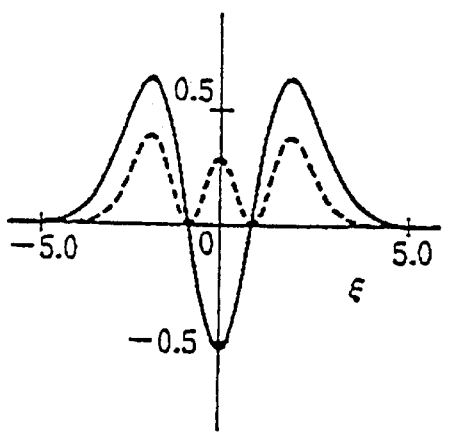
Figure 37:
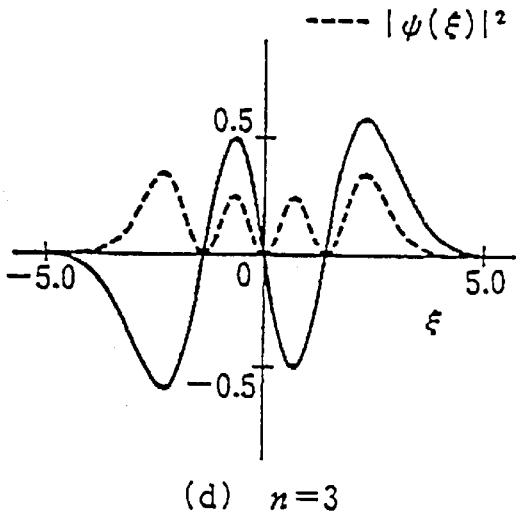

FIG. 36 illustrates one example of the microscope system of this invention when a Nd:YAG laser (56) has a laser resonator having the construction of FIG. 35.

In this example shown in FIG. 36, the adjusted specimen (100) is dyed with the Rhodamine 6G, and there is provided as the light source the mode-locked type Nd:YAG laser (56) which has a laser resonator of the construction of FIG. 35.

This Nd:YAG laser (56) can produce the fundamental-wave of the 1-st-order-Bessel-beam directly. The pump light is produced by converting the wavelength of the fundamental-wave into 2-nd harmonics of 532 nm by axiconTP crystal (57), and the erase light is produced by converting the wavelength of a portion of the 2-nd harmonics to 563 nm by the Raman shifter (4) made of a $Ba(NO_3)_2$ crystal.

Since this erase light is already the 1-st-order-Bessel-beam, the condensing optical system need not be provided, as in the foregoing embodiments, with the phase plate (6) for converting the erase light into the hollow beam or the Al optical system such as the zonal optical system for converting the same into the 1-st-order-Bessel-beam, thus the erase light can be condensed direcly on the adjusted specimen (100) through the dichroic mirrors (7) and (8) and the condensing objective lens (9).

Of course, the condensed beam on the adjusted specimen (100) is the 1-st-order-Bessel-beam.

Since the optical system for forming the 1-st-order-Bessel-beam is thus firmly assembled in the laser, the condensing optical system can have a simple construction but can be strong against dislocation and excellent in stability to improve the super-resolution and operability better.

As the optical system capable of giving the boundary condition for forming the 1-st-order-Bessel-beam, not only the aforementioned ring-shaped zonal mirror (52) or the phase plate for giving the beam the phase difference in which the electric fields axially symmetric with respect to the electric field of the plane normal to the optical axis but also the zonal diffraction grating, the Fresnel zone plate or the zonal aperture and the like can be placed in the resonator of the laser light source for the erase light.

Generally, the laser can generate beam patterns having various mode patterns in dependence upon the construction of its resonator. In the vibrational mode of a higher order of the Gauss's type, Laguerre's type or Hermitian's type, therefore, there exists a pattern in which the intensity is zero at the central portion of the laser beam, as illustrated in FIGS. 37(a) to 37(d).

Hence, the various lasers of the light source can have an excellent super-resolution, as the 1-st-order-Bessel-beam has, not only by giving the laser resonator the construction illustrated in FIG. 35, but also by oscillating the laser beam having the vibrational modes of higher orders of the Gauss's type, Laguerre's type or Hermitian's type.

Example 8

In the microscope system of this invention thus far described, the S/N ratio of the fluorescence signal to go into the emission detector from the specimen can be improved by using several filter elements.

In the super-resolution microscope, generally, there exist not only the fluorescence from the observatory specimen to be detected but also several background lights. These background lights are: i) the scattered light of the pump light; ii) the scattered light of the erase light; and iii) the fluorescence from the optical system other than the specimen.

i) This scattered light has the wavelength $\lambda 1$ of the pump light and is scattered mainly on the surface of the condenser lens or at the boundary of the cover glass for protecting the observatory specimen.

ii) This scattered light has the wavelength $\lambda 1$ of the erase light for the same reason as that of i). The erase light has a higher intensity than that of the pump light so that it raises an obstruction to the fluorescence detection.

iii) If the glass material for the lens or cover glass of the optical system is an ideal non-fluorescent quartz or a fluorite, there exists no fluorescence having a wavelength range of 250 nm or more. In a poor glass material, however, a fluorescence comes from the impure portion or color center.

These background lights may also be produced in the super-resolution microscope body of the microscope system of this invention. Therefore, the background lights are desirably prevented from migrating into the fluorescence and going into the detector, thereby to improve the S/N ratio.

Figure 38:
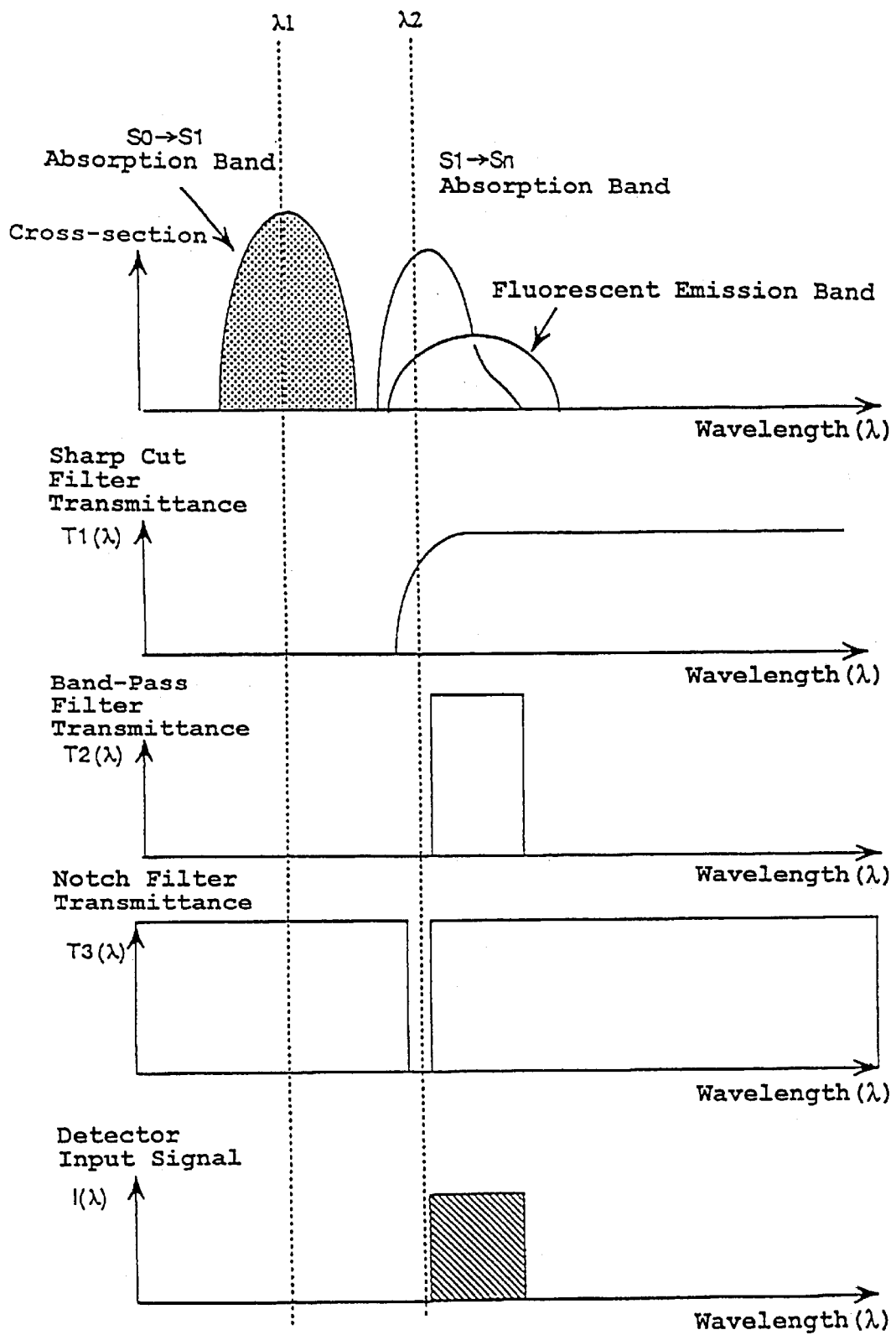
FIG. 38 are diagrams illustrating relations between the wavelength characteristics of various filters and the wavelength characteristics of detected lights.

As illustrated in FIG. 38, basically, the background lights can be completely eliminated by a combination of the optical filter and the spatial filter.

Ordinarily, the wavelength $\lambda 1$ of the pump light is the shortest, and the wavelength $\lambda 2$ of the erase light and the wavelength band of the fluorescence at the deexcitation from S1 to S0 on the longer wave side.

In the Rhodamine 6G, the absorption band from S1 to S2 and the fluorescence wavelength band from S1 to S0 overlap each other, and the wavelength λ2 and the fluorescence wavelength to be detected are close to each other. When such molecule is to be used as the fluorescence labeler molecule, therefore, the background lights are desired to be carefully eliminated.

First of all, the scattered light i) of the pump light can be eliminated, because the wavelengths of the pump light and the erase light are generally apart from each other, by providing a sharp cut filter which is prepared by diffusing a absorbent containing a polymer over the glass substrate or coating the glass substrate with an interference film.

It is apparent from FIG. 38, for example, that the shorter wave side than the wavelength λ2 can be completely eliminated by such sharp cut filter. For example, if the sharp cut filter using a dielectric multi-layer film is designed for the optimum, giving an interval of about±30 nm of the wavelength-separating-design position, the light on the shorter wave side of the wavelength width can be eliminated substantially by 100% whereas the light on the longer wave side can be transmitted. In the Rhodamine 6G, since the fluorescence measurement wavelength region and the pump light are apart from each other by 40 nm or more, as has been illustrated in FIG. 14, the scattered light of the pump light can be separated and eliminated from the fluorescence coming from the specimen by the sharp cut filter.

This sharp cut filter can be placed on the optical path of the fluorescence in front of the fluorescence detector (or the photomultiplier (14)), as illustrated in FIG. 26 of the foregoing Example 4.

Next, the erase light ii) can be eliminated by providing a notch filter. The notch filter is one using a dielectric multi-layered film not to transmit only a predetermined wavelength, as illustrated in FIG. 38. The light in a band of about 20 nm around the designed wavelength can be completely eliminated if more of the dielectric multi-layered film are laminated to optimize thickness of the dielectric multi-layered film.

Especially in the case of the Rhodamine 6G, the fluorescence emission region extends to 550 to 650 nm, and the wavelength of the erase light is 562 nm. By the notch filter, however, the scattered light of the erase light in the vicinity of 562 nm can be prevented from entering the detector.

On the other hand, when the emission of the fluorescence from the specimen is inhibited as in the Rhodamine 6G by making use of the double resonance absorption process and the induced emission, the absorption band from S1 to S2 and the fluorescence wavelength band from S1 to S0 overlap each other, so that the fluorescence going into the emission detector from the specimen is partially lost. By using the notch filter, however, only the fluorescence in a band of about 20 nm including 562 nm of the region of 550 to 650 nm is lost, so that the loss of the fluorescence to be observed can be minimized.

Furthermore, in order to eliminate the background light other than the fluorescence from the specimen more completely, it is also preferable to use a band-pass filter. This band-pass filter is prepared by coating the glass substrate with a dielectric multi-layered film and, on the contrary to the notch filter, contains a specific wavelength to transmit only the light of the wave region around that specific wavelength.

Consequently, with the band-pass filter not transmitting the wavelengths of the pump light and the erase light but transmitting only the fluorescence emission wavelength band, the wavelengths other than that of the fluorescence from the specimen can be completely cut.

As described hereinbefore, by providing the emission condensing optical system for condensing the emission from the specimen to the emission detector, for example, with the sharp cut filter, the notch filter and the band-pass filter, the fluorescence to be emitted when the fluorescence labeler molecule is to be deexcited can be detected at a remarkably excellent S/N ratio.

For the elimination of the fluorescence from the optical system other than the specimen iii), since the fluorescence is caused by the impurity or the color center of the glass material of the lens of the optical system or the cover glass, no problem arises if an ideal synthetic quarts (i.e., non-fluorescent quarts) or a fluorite is utilized.

Such glass material may be exemplified not only by the synthetic quarts but also by $CaF_2$, NaF, $Na_3AlF_6$, LiF, $MgF_2$, $SiO_2$, $LaF_3$, $NdF_3$, $Al_2O_3$, $CeF_3$, $PbF_2$, Mgo, $ThO_2$, $SnO_2$, $La_2O_3$ or SiO.

Of course, it is desired to provide a filter optical system for separating the fluorescence coming from the specimen and the fluorescence coming from the optical system other than the specimen. Such filter optical system may be exemplified by a spatial filter such as a slit or a pin hole.

Figure 39:
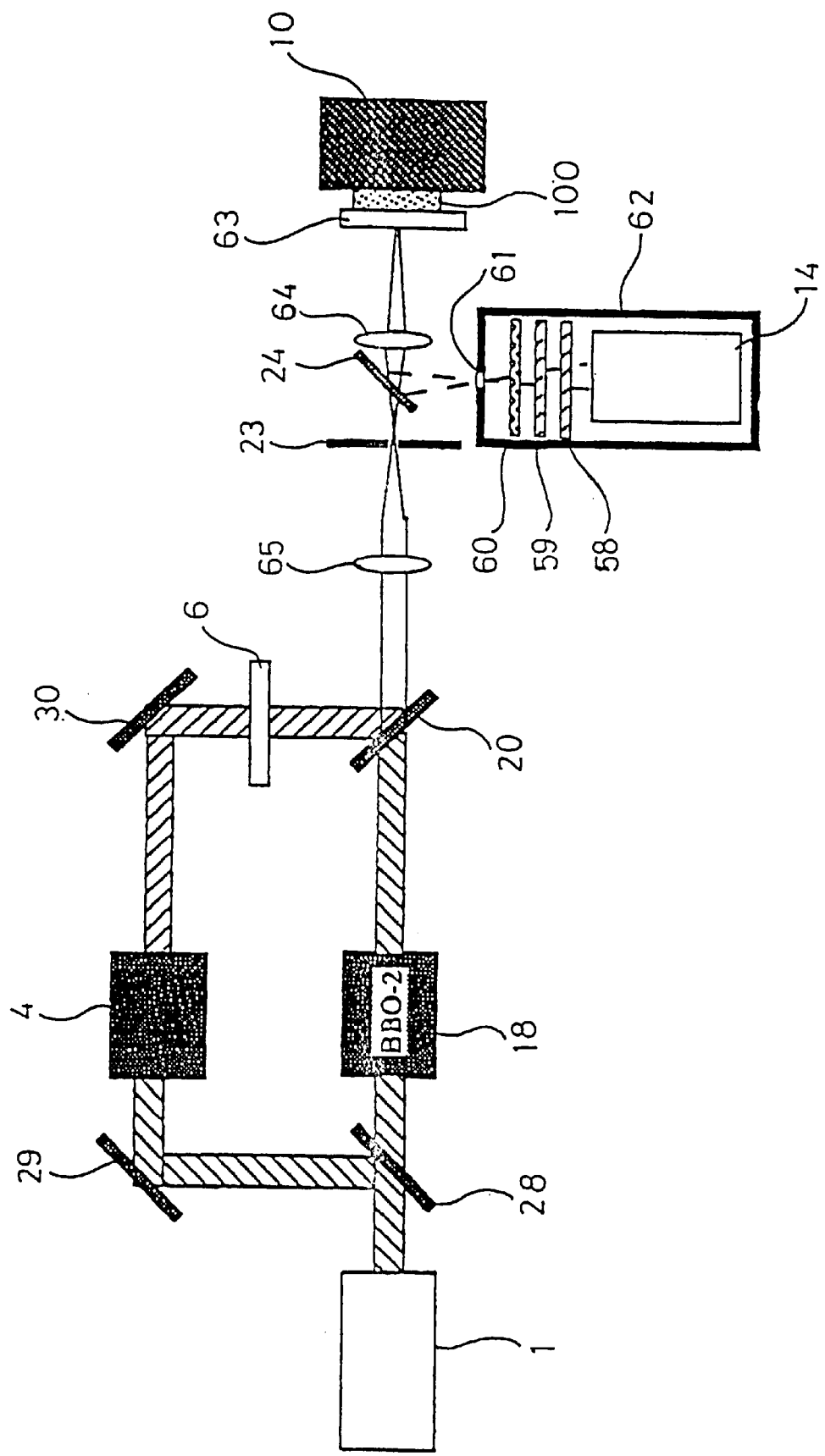
FIG. 39 is a construction diagram showing an essential portion of one example of the microscope system of this invention, which is provided with a filter optical system.

FIG. 39 illustrates one example of the microscope system of this invention, which is provided with the filter optical system.

In the filter optical system of this microscope system of FIG. 39, there are arranged, in a shade box (62) and in front of the notch filter (14), a notch filter (58), a band-pass filter (59) and a sharp cut filter (60) in the recited order. Moreover, a pin hole (61) is formed in the facial portion of the shade box (62) facing the dichroic mirror (24).

On the other hand, the side of the adjusted specimen (100) to which the laser beam is irradiated is covered with and protected by a cover glass (63). This cover glass (63) is formed of the aforementioned glass material, for example.

In this microscope system of FIG. 39, the pin hole (23) and the pin hole (61) functioning as a spatial filter take confocal positions with respect to an objective lens (64) and the face of the adjusted specimen (100). Although apparent from a ray tracing in the case of such confocal optical system, the fluorescence emitted from other than the focal point of the pump light and the erase light, i.e., other than the specimen face cannot pass through the pin hole (61) and cannot reach the receiving face of the photomultiplier (14) that is an emission detector.

For example, the fluorescence emitted from the cover glass (63) is not focused on the pin hole (61) if it passes through the objective lens (64). As a result, the unfocused numerous fluorescences cannot pass through the pin hole (61). On the other hand, the fluorescence emitted from the face of the objective lens (64) is not condensed directly on the pin hole (61) by the objective lens (64) so that it does not pass through the pin hole (61) or reach the receiving face of the photomultiplier (4).

According to the notations of FIG. 38, the fluorescence intensity $I_{signal}$ going into the emission detector can be expressed by the following equation:

$$I_{signal} = \int_{\lambda_{ex1}}^{\lambda_{ex2}} I(\lambda) d\lambda = \int_{\lambda_{ex1}}^{\lambda_{ex2}} T_1(\lambda) T_2(\lambda) T_3(\lambda) F(\lambda) d\lambda \quad \text{Equation 19}$$

In this equation, $F(\lambda k)$ indicates a fluorescent intensity of the fluorescence labeler molecule, and $\lambda_{ex1}$ and $\lambda_{ex2}$ indicate the lower limit wavelength and the upper limit wavelength of the sensitivity range of the emission detector, respectively. As shown in FIG. 38, $I_{signal}$ corresponds to the fluorescent intensity from the specimen without migration of the background lights.

Here in FIG. 39, if the objective lens (64) is a reflecting objective lens, there is no fluorescence from the lens glass material so that the SIN ratio can be better improved.

Example 9

Figure 40:
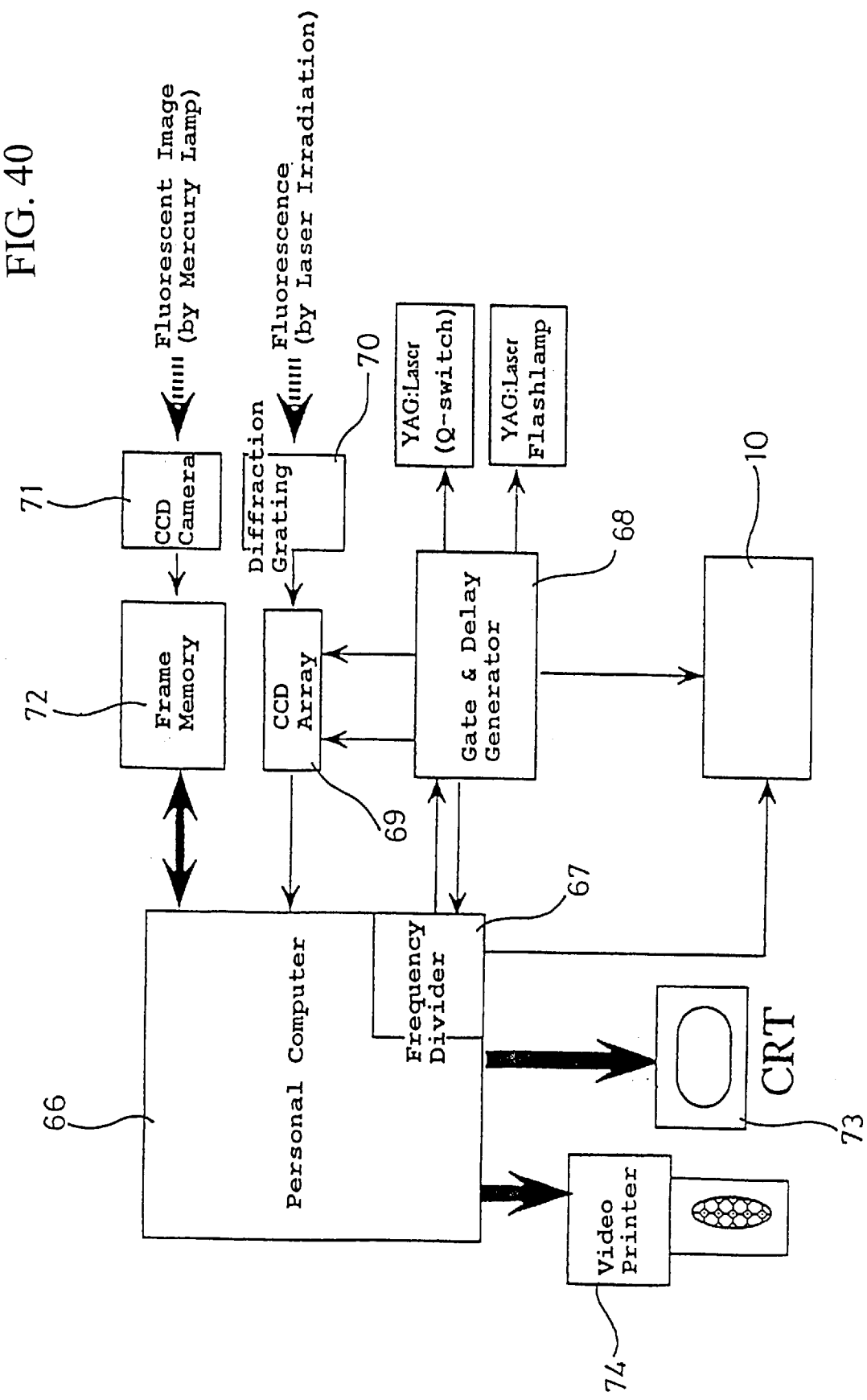
FIG. 40 is a construction diagram showing an essential portion of one example of an electric system corresponding to the microscope system of this invention of FIG. 34.

FIG. 40 shows one example of an electric system corresponding to the microscope system of this invention, as illustrated in FIG. 34 of Example 6.

In the example shown in FIG. 40, all the systems in the microscope system of this invention are controlled basically by a personal computer (66).

This personal computer (66) controls the oscillations of the YAG laser and the drive of the two-dimensional carriage stage (10) that is a scanning stage of the adjusted specimen (100) of FIG. 34, for example.

The timings of the system are all based on the clock of the personal computer (66). This clock is divided by a frequency divider (67) into a frequency capable of oscillating a laser, and the clock signal thus divided becomes a Q-switch signal and a flash lamp signal for the laser control by delay and waveform shape with a gate & delay generator (68) to control the YAG laser.

The fluorescent spectrum at each laser shot is monitored by a CCD array (69). More specifically, in response to the laser shot, more specifically, the fluorescence emitted from the adjusted specimen (100) is divided by a diffraction grating (70) and then is detected as a fluorescent spectrum by the one-dimensional CCD array (69).

The stored data of each pixel of the CCD array (69) are transferred at each laser shot to the memory of the personal computer (66) while being synchronized with the movement of the two-dimensional carriage stage (10) and the laser emission.

From the fluorescent spectral data stored in the memory of the personal computer (66), only the data of a predetermined fluorescent wavelength are extracted by the numerical operations of the personal computer (66), and with this extracted data, a two-dimensional scanned image of the adjusted specimen (100) is formed.

By analyzing a two-dimensional scanned image graphically is for each measured wavelength, it is possible not only to achieve a mere fluorescent image but also to analyze the two-dimensional composition.

Moreover, the fluorescent image of the adjusted specimen (100), as obtained by the irradiation of the mercury lamp (31), is simultaneously monitored by a CCD camera (71), and its fluorescent image data can be stored in a frame memory (72) at any time.

As a result, separately of the two-dimensional scanned image, the entire fluorescent image of the adjusted specimen (100) can be monitored at any time. This function is remarkably convenient especially for the micro manipulation using the hollow micro beam, as has been described hereinbefore.

In addition, the personal computer (66) can control a CRT (73) and the frame memory (72) to display and process the image whenever necessary. The graphic data thus prepared can be outputted by the CRT (73) or a video printer (74), for example.

This invention should not be limited to the foregoing Examples but can take various modes in detail.

INDUSTRIAL APPLICABILITY

According to this invention, as has been described in detail hereinbefore, there is provided a novel microscope system which is capable to condense, in an excellent beam profile, an erase light exciting a molecule in the first excited state to the second excited state by using a simple, compact optical system and which has high stability and operability and an excellent super-resolution. Also provided is a novel microscope system which has a micro manipulator function to capture and move specimen particles, without damaging the specimen, by using the erase light being a hollow beam.

Figure 5:
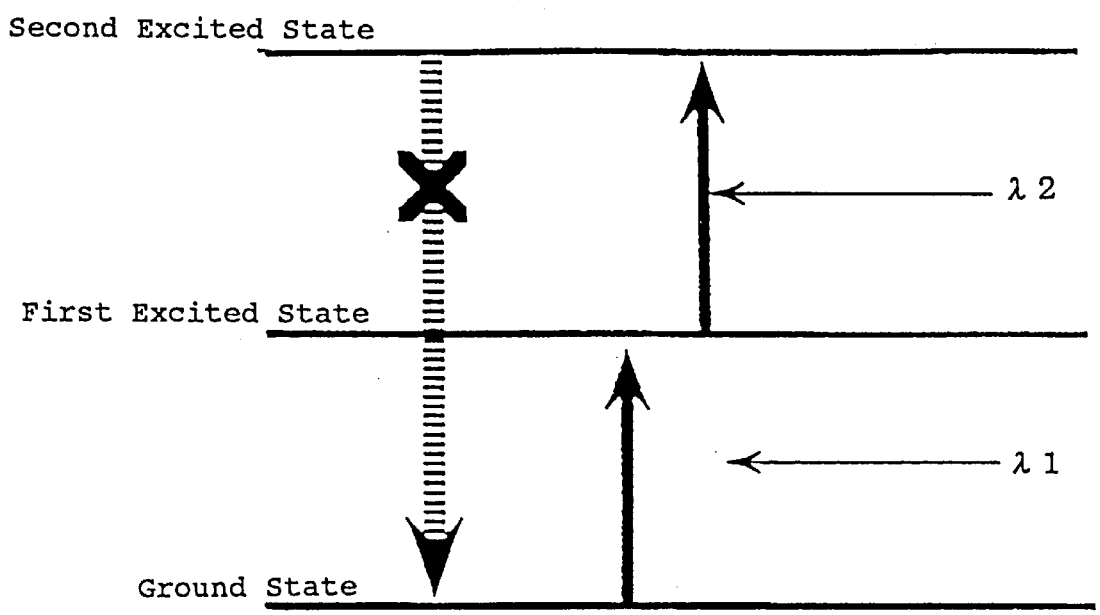
FIG. 5 is a conceptional diagram illustrating a principle of a super-resolution microscope for a molecule having a low emission yield in the second excited state.
Figure 6:
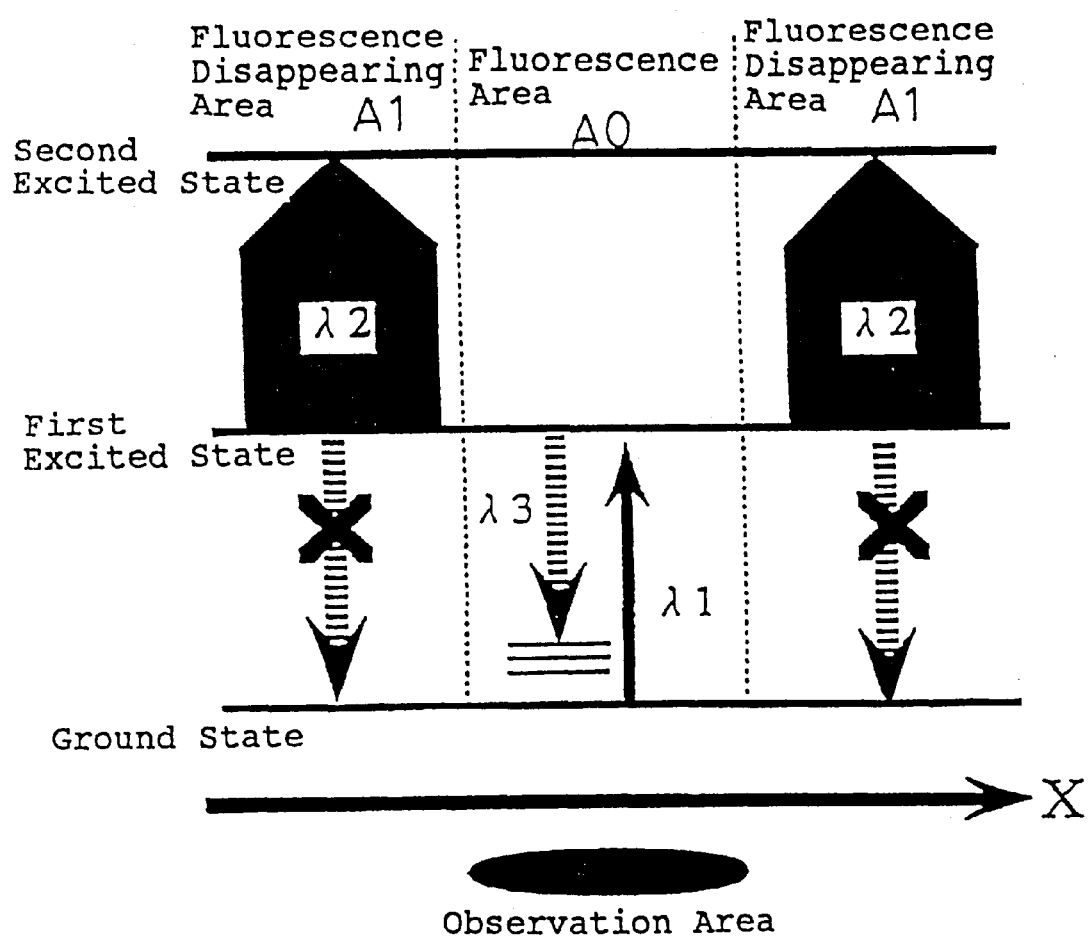
FIG. 6 is a diagram illustrating a double resonance absorption process.
Figure 7:
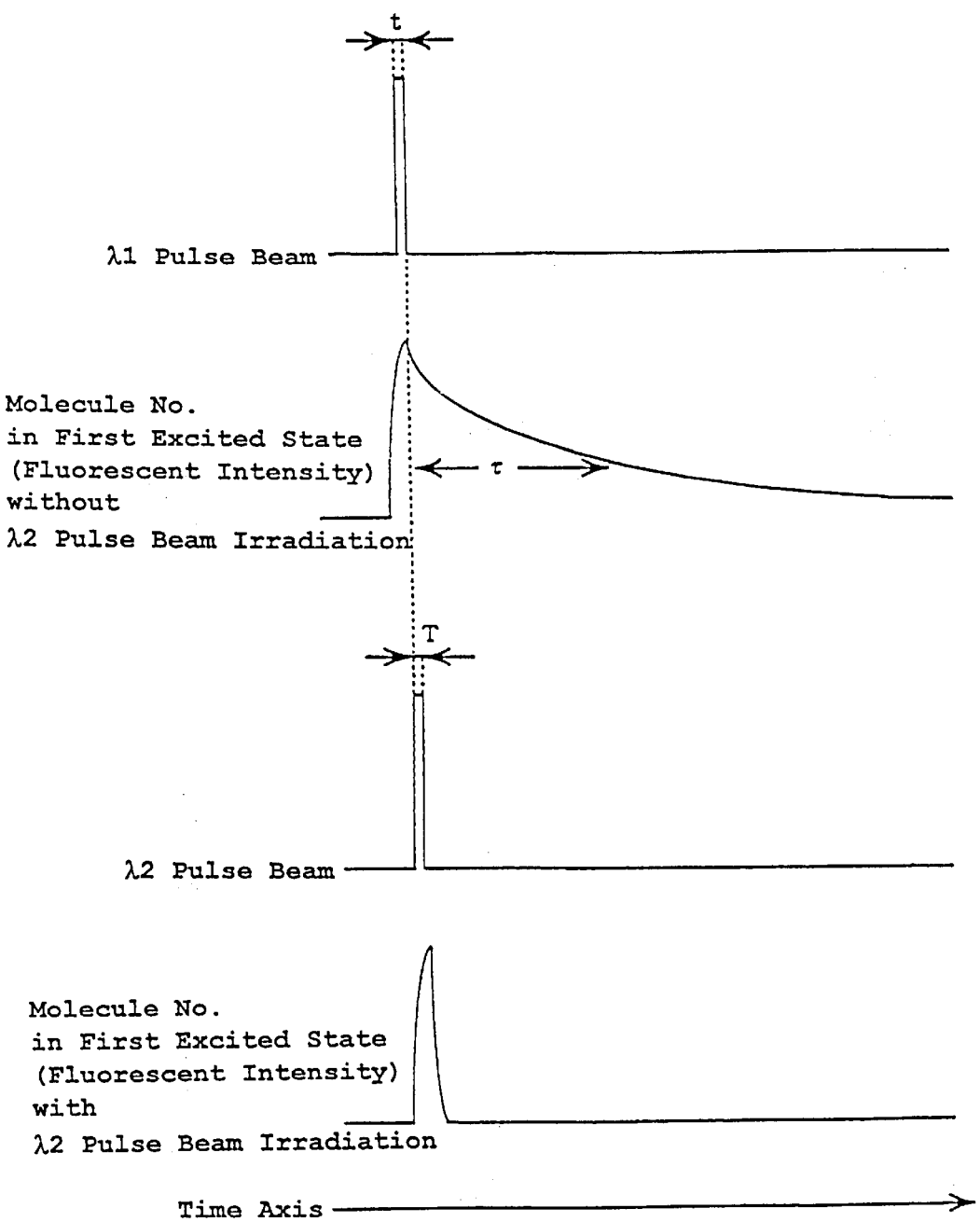
FIG. 7 is a diagram illustrating one example of irradiation timings of lights of wavelengths λ1 and λ2 and the number of molecules in the first excited state.
Figure 8:
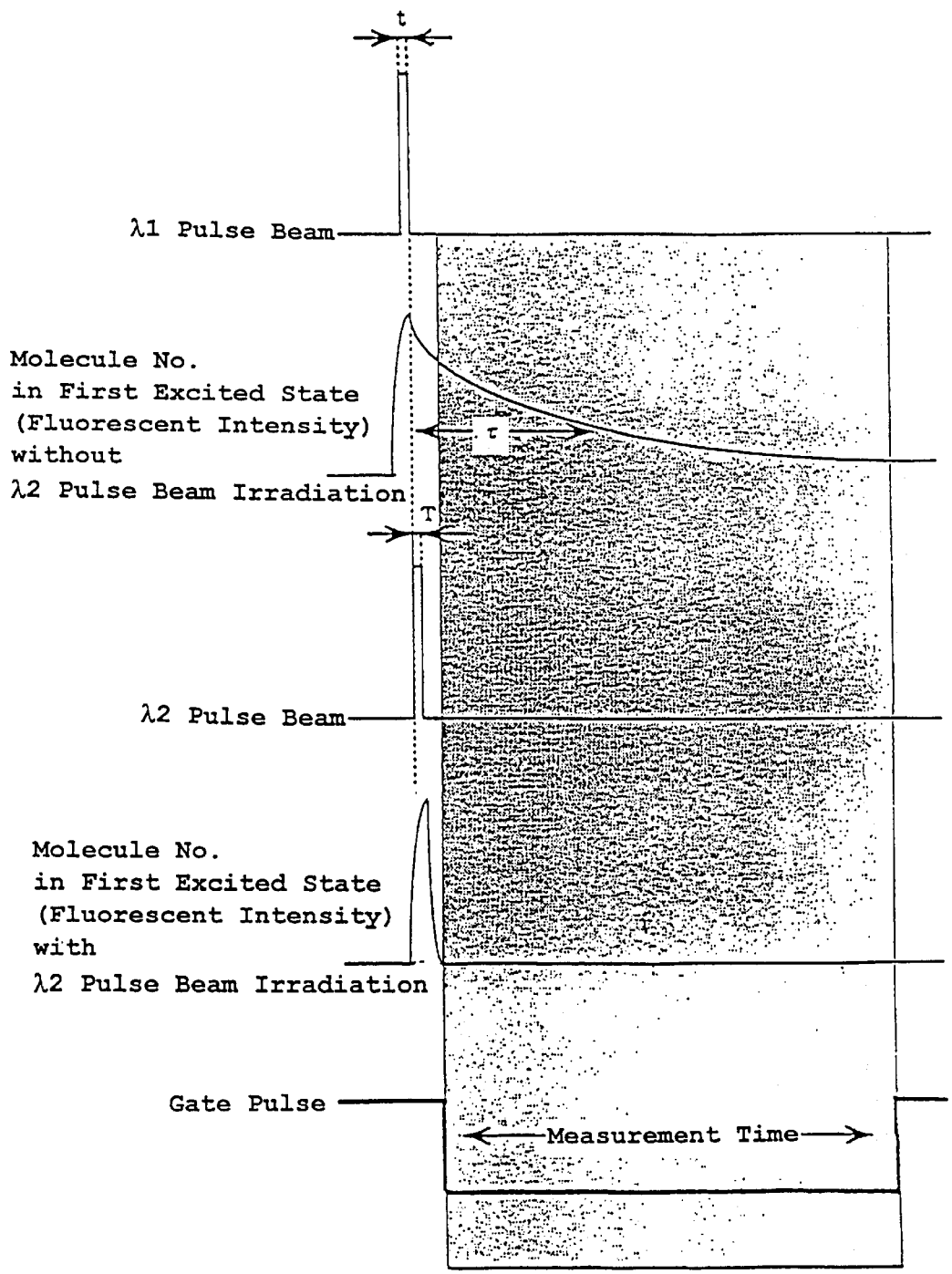
FIG. 8 is a diagram illustrating one example of irradiation timings of the lights of the wavelengths λ1 and λ2 and measurement timings.
Figure 9:
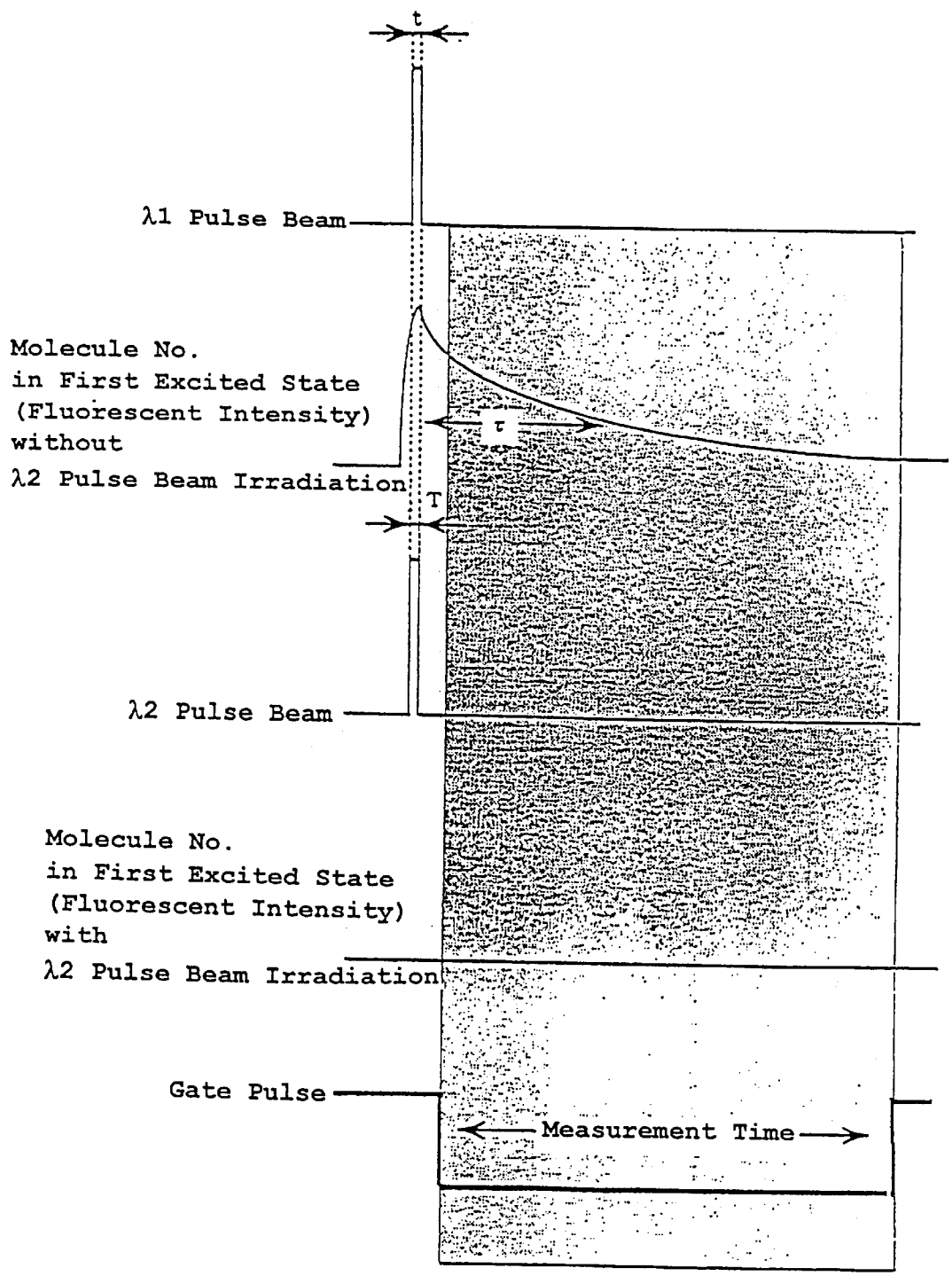
FIG. 9 is a diagram illustrating another example of the irradiation timings of the lights of the wavelengths λ1 and λ2 and the measurement timings.
Figure 10:
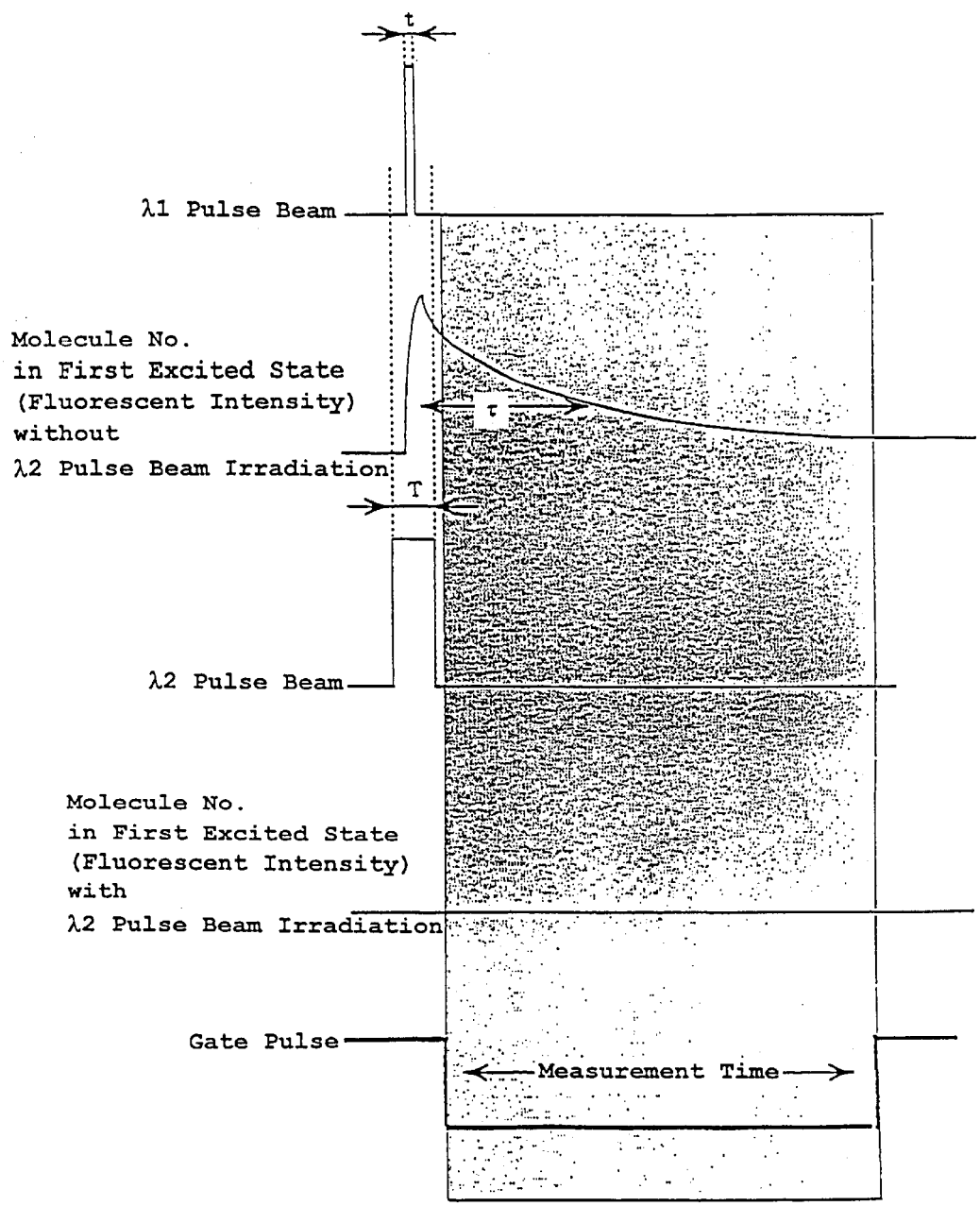
FIG. 10 is a diagram illustrating another example of the irradiation timings of the lights of the wavelengths λ1 and λ2 and the measurement timings.
Figure 11:
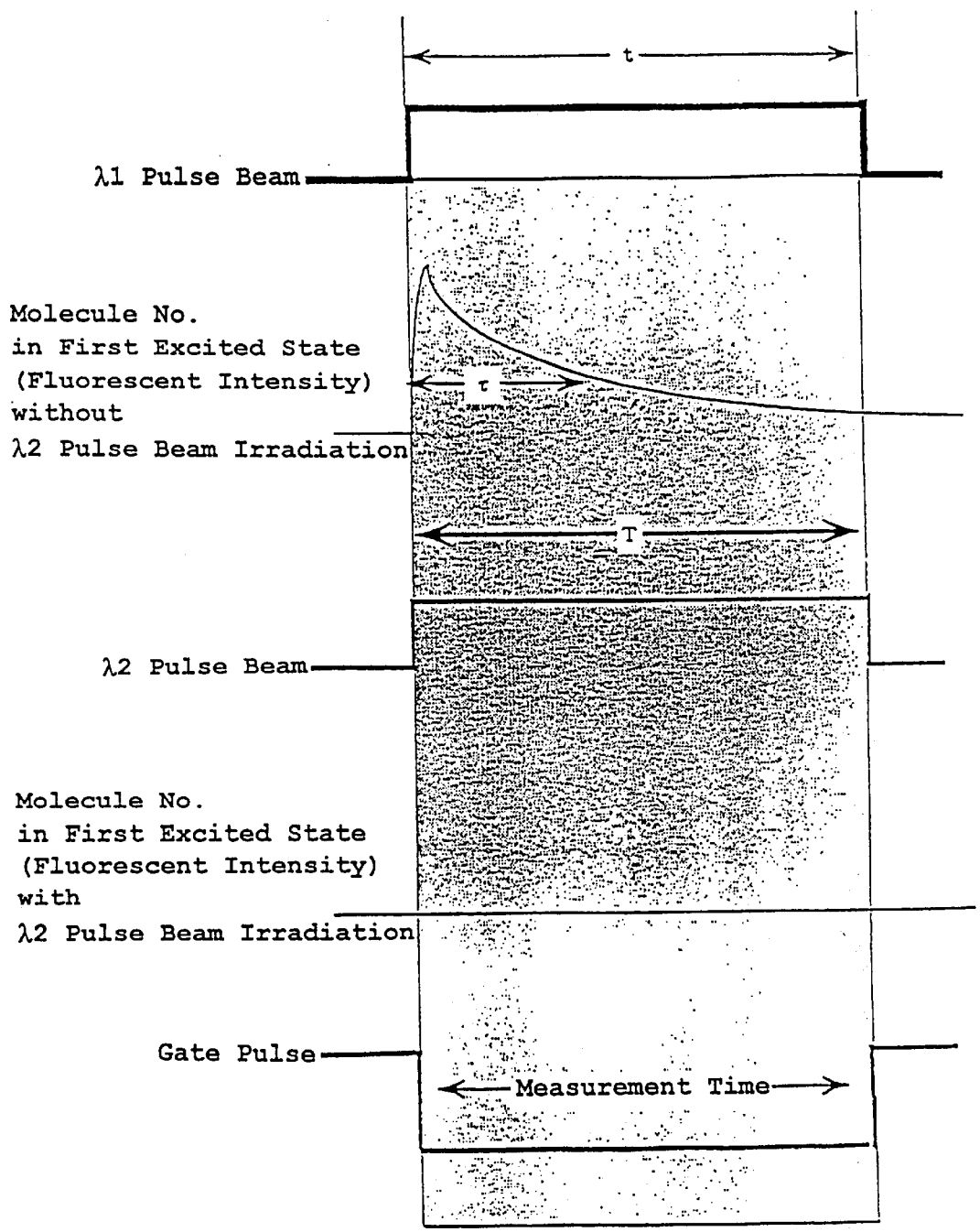
FIG. 11 is a diagram illustrating another example of the irradiation timings of the lights of the wavelengths λ1 and λ2 and the measurement timings.

FIGS. 1 to 4
  Valence Orbit 4 (Vacant Orbit)
  Valence Orbit 3 (Vacant Orbit)
  Valence Orbit 2
  Valence Orbit 1
  Inner-shell Orbit
  Occupant Electron
  Wavelength $\lambda 1$
  Wavelength $\lambda 2$
  Fluorescence or
  Phosphorescence
FIG. 5
  Second Excited State
  First Excited State
  Ground State
FIG. 6
  Fluorescence Disappearing Area A1
  Fluorescence Area A0
  Second Excited State
  First Excited State
  Ground State
  Observation Area
FIGS. 7 to 11
  $\lambda 1$ Pulse Beam
  Molecule No.
  in First Excited State
  (Fluorescent Intensity)
  without
  $\lambda 2$ Pulse Beam Irradiation
  $\lambda 2$ Pulse Beam
  Molecule No.
  in First Excited State
  (Fluorescent Intensity)
  with
  $\lambda 2$ Pulse Beam Irradiation
  Time Axis
  Gate Pulse
  Measurement Time
FIG. 12
  Vibrational Relaxation
  Vibrational Relaxation
  Vibrational Relaxation
  Vibrational Relaxation
  Internal Conversion
  Internal Conversion
  Inter-System Crossing
  Light Absorption
  Fluorescence
  Phosphorescence
FIG. 14
  Cross-section Wave Number
Wavelength (nm)
Harmonic Curve
Rhodamine6G
(Ethanol Solution)

FIG. 19
Pupil
where
Maximum Transmittance of Objective
Maximum Transmittance of Multilayer
Shading Ratio FIGS. 20, 24 & 25
Standardized Fluorescence / Erase Light Intensity
(Arbitrary Unit)
Spatial Distance
(micron)
Erase Light
Intensity
Fluorescence
Intensity
Erase Light
Wavelength: 560 nm
Laser Light
Pulse Width: 150 psec
Maximum Intensity
of Erase Light
:36 MW/cm$^2$
Aperture Ratio
:100%

FIG. 23
Magnesium Fluoride Film
Glass Substrate

FIG. 26
Double Wave
Raman Shifter

FIG. 27
Object Point
Condense Point

FIG. 28
Cassegrain (Schwalzschild) Type
Reflecting Mirror

FIG. 29
Walter Type

FIG. 30
Under-Film

FIG. 31
AlGaAs Upper Cladding
GaAs Quantum Well
AlGaAs Core
AlGaAs Lower Cladding
GaAs Substrate FIG. 32
Reflecting Surface
Microscope
Lamp
Mirror with Pinhole FIG. 35
Output FIG. 36
Double Wave
Raman Shifter FIG. 38
Cross-section
Wavelength ($\lambda$)
Wavelength ($\lambda$)
Wavelength ($\lambda$)
Wavelength ($\lambda$)
Wavelength ($\lambda$)
Absorption Band
Absorption Band
Fluorescent Emission Band
Sharp Cut
Filter
Transmittance
Band-Pass
Filter
Transmittance
Filter
Transmittance
Detector
Input Signal FIG. 40
66 Personal Computer
67 Frequency Divider
68 Gate & Delay Generator
69 CCD Array
70 Diffraction Grating Fluorescence (by Laser Irradiation)
71 CCD Camera Fluorescent image (by mercury lamp)
72 Frame memory
74 Video Printer (Q-switch) flashlamp

What is claimed is:

1. A microscope system comprising:
an adjusted specimen; and
a microscope body;
wherein said adjusted specimen is dyed with a molecule which has three electron states including at least a ground state and which has an excited wavelength band from a first electron excited state to a second electron excited state which overlaps a fluorescent wavelength band upon deexcitation through a fluorescence process from the first electron excited state to a vibrational level in the ground state;
wherein said microscope body includes:
a light source operable to provide light having a wavelength $\lambda 1$ for exciting the molecule from the ground state to the first electron excited state;
a light source operable to provide light having a wavelength $\lambda 2$ for exciting the molecule in the first electron excited state to the second or higher electron excited state;
a condensing optical system operable to condense the light having the wavelength $\lambda 1$ and the light having the wavelength $\lambda 2$ on said adjusted specimen;
an overlap device operable to partially overlap an irradiation region of the light having the wavelength $\lambda 1$ and an irradiation region of the light having the wavelength $\lambda 2$ on said adjusted specimen; and
an emission detector operable to detect an emission upon deexcitation of the excited molecule to the ground state;

wherein a region of the emission upon deexcitation of the molecule from the first electron excited state to the ground state is inhibited by irradiating the light having the wavelength λ1 and the light having the wavelength λ2 through said overlap device; and wherein a beam obtained by condensing the light having the wavelength λ2 has a phase distribution in which the phase is shifted by π at a symmetric position with respect to an optical axis of the beam in a plane normal to the optical axis.

2. A microscope system of claim 1, wherein the beam obtained by condensing the light having the wavelength λ2 has a phase distribution in which the phase changes continuously from 0 to 2π when turned once around the optical axis in a plane normal to the optical axis.

3. A microscope system of claim 1, wherein an excitation wavelength band from the first electron excited state to the second electron excited state and an excitation wavelength band from the ground state to the first electron excited state are different.

4. A microscope system of claim 1, wherein an optical axis of a beam obtained by condensing the light having the wavelength λ1 and the optical axis of the beam obtained by condensing the light having the wavelength λ2 are coaxial.

5. A microscope system of claim 1, wherein the beam obtained by condensing the light having the wavelength λ2 has a phase distribution in which the phase changes discontinuously from 0 to 2π when turned once around the optical axis in the plane normal to the optical axis.

6. A microscope system of claim 1, wherein the beam obtained by condensing the light having the wavelength λ2 is a Bessel beam.

7. A microscope system of claim 6, wherein the Bessel beam is a 1-st-order-Bessel-beam.

8. A microscope system of claim 1, wherein the beam obtained by condensing the light having the wavelength λ2 is a laser beam having a vibrational mode of any one of a Gauss's type, Laguerre's type and Hermitian's type.

9. A microscope system of claim 1, wherein any of a gas laser, a solid laser and a semiconductor laser is provided as said light source for the light having the wavelength λ1.

10. A microscope system of claim 9, wherein an oscillation wavelength of any of the gas laser, the solid laser and the semiconductor laser is the wavelength λ1.

11. A microscope system of claim 9, wherein a harmonic-wave of an oscillation wavelength of any of the gas laser, the solid laser and the semiconductor laser has the wavelength λ1.

12. A microscope system of claim 9, wherein a sum frequency of, or a difference frequency between, an oscillation wavelength of any of the gas laser, the solid laser and the semiconductor laser and a harmonic-wave of the oscillation wavelength has the wavelength λ1.

13. A microscope system of claim 9, wherein the gas laser is any one of an excimer laser, a copper vapor laser, an argon laser, a He-Ne laser, a $CO_2$ laser, a He-Cd laser and a nitrogen laser.

14. A microscope system of claim 13, wherein the gas laser is of a mode-locked type.

15. A microscope system of claim 9, wherein the solid laser is any one of a Nd:YAG laser, a Ti sapphire laser, a YLF laser and a ruby laser.

16. A microscope system of claim 15, wherein the solid laser is of a semiconductor-laser-excited type.

17. A microscope system of claim 15, wherein the solid laser is of a mode-locked type.

18. A microscope system of claim 9, wherein said microscope body has at least one of a nonlinear media and a wavelength modulating element for converting a wavelength of a laser beam from the gas laser, the solid laser or the semiconductor laser.

19. A microscope system of claim 18, wherein the nonlinear media or the wavelength modulating element is a nonlinear crystal.

20. A microscope system of claim 18, wherein the nonlinear media or the wavelength modulating element is a Raman shifter.

21. A microscope system of claim 18, wherein the light having the wavelength λ1 is prepared by modulating a wavelength of a fundamental-wave of the gas laser or the solid laser with the nonlinear media or the wavelength modulating element.

22. A microscope system of claim 18, wherein the light having the wavelength λ1 is prepared by modulating a wavelength of harmonic-wave of the gas laser or the solid laser with the nonlinear media or the wavelength modulating element.

23. A microscope system of claim 18, wherein the light having the wavelength λ2 is prepared by modulating a wavelength of a fundamental-wave of the gas laser or the solid laser with the nonlinear media or the wavelength modulating element.

24. A microscope system of claim 18, wherein the light having the wavelength λ2 is prepared by modulating a wavelength of a harmonic-wave of the gas laser or the solid laser with the nonlinear media or the wavelength modulating element.

25. A microscope system of claim 9, wherein in a resonator of the gas laser, the solid laser or the semiconductor laser, there is provided at least one of a ring-shaped zonal mirror, a zonal diffraction grating, a Fresnel zone plate, a zonal aperture, and a phase plate which gives a phase difference in which electric fields axially symmetric in a plane normal to the optical axis are shifted by π from each other.

26. A microscope system of claim 1, wherein any of a gas laser, a solid laser and a semiconductor laser is provided as said light source for the light having the wavelength λ2.

27. A microscope system of claim 26, wherein an oscillation wavelength of any of the gas laser, the solid laser and the semiconductor laser is the wavelength λ2.

28. A microscope system of claim 26, wherein a harmonic-wave of an oscillation wavelength of any of the gas laser, the solid laser and the semiconductor laser has the wavelength λ2.

29. A microscope system of claim 26, wherein a sum frequency of, or a difference frequency between, an oscillation wavelength of any of the gas laser, the solid laser and the semiconductor laser and a harmonic-wave of the oscillation wavelength has the wavelength λ2.

30. A microscope system of claim 1, wherein said condensing optical system for the light having the wavelength λ2 has a phase plate having a refractive-index distribution or an optical-path-difference distribution which gives, to the beam obtained by condensing the light having the wavelength of the λ2, a phase difference distribution in a plane normal to an optical axis of the beam.

31. A microscope system of claim 1, wherein said condensing optical system for the light having the wavelength λ2 has a zonal optical system.

32. A microscope system of claim 1, wherein said condensing optical system for the light having the wavelength λ2 has a diffractive optical system.

33. A microscope system of claim 1, wherein said condensing optical system for the light having the wavelength λ2 has an axicon.

34. A microscope system of claim 1, wherein said microscope body has an emission condensing optical system for condensing an emission from the molecule to said emission detector.

35. A microscope system of claim 34, wherein said emission condensing optical system has a sharp cut filter.

36. A microscope system of claim 34, wherein said emission condensing optical system has a notch filter.

37. A microscope system of claim 34, wherein said emission condensing optical system has a band-pass filter.

38. A microscope system of claim 37, wherein the band-pass filter transmits the emission from the molecule while not transmitting the light having the wavelength $\lambda 1$ and the light having the wavelength $\lambda 2$.

39. A microscope system of claim 1, wherein said adjusted specimen is sealed by a seal device made of a substance transmitting the light having the wavelength $\lambda 1$ and the light having the wavelength of $\lambda 2$.

40. A microscope system of claim 39, wherein the substance is synthetic quartz SiO2, CaF2, NaF, Na3AlF6, LiF, MgF2, SiO2, LaF3, NdF3, Al2O3, CeF3, PbF2, MgO, ThO2, SnO2, La2O3 or SiO.

41. A microscope system of claim 1, wherein said adjusted specimen is covered by a cover device made of a substance transmitting the light having the wavelength $\lambda 1$ and the light having the wavelength of $\lambda 2$.

42. A microscope system of claim 1, what said microscope body has a continuous-wave laser which is separate from said light sources for the light having the wavelength $\lambda 1$ and the light having the wavelength $\lambda 2$, and wherein a beam obtained by condensing the continuous-wave laser on said adjusted specimen has a phase distribution in which the phase is shifted by $\pi$ at a symmetric position with respect to the optical axis of the beam in the plane normal to the optical axis.

43. A microscope system of claim 1, wherein said microscope body has a device for relatively scanning, on said adjusted specimen, with a beam obtained by condensing a continuous-wave laser on said adjusted specimen, independently of a beam obtained by condensing the light having the wavelength $\lambda 1$ and the beam obtained by condensing the light having the wavelength of $\lambda 2$.

44. A microscope system comprising:
an adjusted specimen; and
a microscope body;
wherein said adjusted specimen is dyed with a molecule which has three electron states including at least a ground state;
wherein said microscope body includes:
a light source operable to provide light having a wavelength $\lambda 1$ for exciting the molecule from the ground state to the first electron excited state;
a light source operable to provide light having a wavelength $\lambda 2$ for exciting the molecule in the first electron excited state to the second or higher electron excited state;
a condensing optical system operable to condense the light having the wavelength $\lambda 1$ and the light having the wavelength $\lambda 2$ on said adjusted specimen;
an overlap device operable to partially overlap an irradiation region of the light having the wavelength $\lambda 1$ and an irradiation region of the light having the wavelength $\lambda 2$ on said adjusted specimen; and
an emission detector operable to detect an emission upon deexcitation of the excited molecule to the ground state;
wherein a region of the emission upon deexcitation of the molecule from the first electron excited state to the ground state is inhibited by irradiating the light having the wavelength $\lambda 1$ and the light having the wavelength $\lambda 2$ through said overlap device; and
wherein a beam obtained by condensing the light having the wavelength $\lambda 2$ has a phase distribution in which the phase is shifted by $\pi$ at a symmetric position with respect to an optical axis of the beam in a plane normal to the optical axis.

45. A microscope system of claim 44, wherein the beam obtained by condensing the light having the wavelength $\lambda 2$ has a phase distribution in which the phase changes continuously from 0 to $2\pi$ when turned once around the optical axis in a plane normal to the optical was.

46. A microscope system of claim 44, wherein an excitation wavelength band from the first electron excited state to the second electron excited state and an excitation wavelength band from the ground state to the first electron excited state are different.

47. A microscope system of claim 44, wherein an optical axis of a beam obtained by condensing the light having the wavelength $\lambda 1$ and the optical axis of the beam obtained by condensing the light having the wavelength $\lambda 2$ are coaxial.

48. A microscope system of claim 44, wherein the beam obtained by condensing the light having the wavelength $\lambda 2$ has a phase distribution in which the phase changes discontinuously from 0 to $2\pi$ when turned once around the optical axis in the plane normal to the optical axis.

49. A microscope system of claim 44, wherein the beam obtained by condensing the light having the wavelength $\lambda 2$ is a Bessel beam.

50. A microscope system of claim 44, wherein the beam obtained by condensing the light having the wavelength $\lambda 2$ is a laser beam having a vibrational mode of any one of a Gauss's type, Laguerre's type and Hermitian's type.

51. A microscope system of claim 44, wherein any of a gas laser, a solid laser and a semiconductor laser is provided as said light source for the light having the wavelength $\lambda 1$.

52. A microscope system of claim 44, wherein any of a gas laser, a solid laser and a semiconductor laser is provided as said light source for the light having the wavelength $\lambda 2$.

53. A microscope system of claim 44, wherein said condensing optical system for the light having the wavelength $\lambda 2$ has a phase plate having a refractive-index distribution or an optical-path-difference distribution which gives, to the beam obtained by condensing the light having the wavelength of the $\lambda 2$, a phase difference distribution in a plane normal to an optical axis of the beam.

54. A microscope system of claim 44, wherein said condensing optical system for the light having the wavelength $\lambda 2$ has a zonal optical system.

55. A microscope system of claim 44, wherein said condensing optical system for the light having the wavelength $\lambda 2$ has a diffractive optical system.

56. A microscope system of claim 44, wherein said condensing optical system for the light having the wavelength $\lambda 2$ has an axicon.

57. A microscope system of claim 44, wherein said microscope body has an emission condensing optical system for condensing an emission from the molecule to said emission detector.

58. A microscope system of claim 44, wherein said adjusted specimen is sealed by a seal device made of a substance transmitting the light having the wavelength $\lambda 1$ and the light having the wavelength $\lambda 2$.

59. A microscope system of claim 44, wherein said adjusted specimen is covered with a cover device made of a substance transmitting the light having the wavelength $\lambda 1$ and the light having the wavelength $\lambda 2$.

60. A microscope system of claim 44, wherein said microscope body has a continuous-wave laser which is separate from said light sources for the light having the wavelength $\lambda 1$ and the light having the wavelength $\lambda 2$, and wherein a beam obtained by condensing the continuous-wave laser on said adjusted specimen has a phase distribution in which the phase is shifted by $\pi$ at a symmetric position with respect to the optical axis of the beam in the plane normal to the optical axis.

61. A microscope system of claim 44, wherein said microscope body has a device for relatively scanning, on said adjusted specimen, with a beam obtained by condensing a continuous-wave laser on said adjusted specimen, independently of a beam obtained by condensing the light having the wavelength $\lambda 1$ and the beam obtained by condensing the light having the wavelength $\lambda 2$.

62. A method for illuminating an adjusted specimen using a microscope body, said method comprising:

dying the adjusted specimen with a molecule which has three electron states including at least a ground state and which has an excited wavelength band from a first electron excited state to a second electron excited state which overlaps a fluorescent wavelength band upon deexcitation through a fluorescence process from the first electron excited state to a vibrational level in the ground state;

providing light having a wavelength $\lambda 1$ for exciting the molecule from the ground state to the first electron excited state;

providing light having a wavelength $\lambda 2$ for exciting the molecule in the first electron excited state to the second or higher electron excited state;

condensing the light having the wavelength $\lambda 1$ and the light having the wavelength $\lambda 2$ on the adjusted specimen;

partially overlapping an irradiation region of the light having the wavelength $\lambda 1$ and an irradiation region of the light having the wavelength $\lambda 2$ on the adjusted specimen; and detecting an emission upon deexcitation of the excited molecule to the ground state;

inhibiting a region of the emission, upon deexcitation of the molecule from the first electron excited state to the ground state, by irradiating the light having the wavelength $\lambda 1$ and the light having the wavelength $\lambda 2$; and wherein a beam obtained by condensing the light having the wavelength $\lambda 2$ has a phase distribution in which the phase is shifted by $\pi$ a symmetric position with respect to an optical axis of the beam in a plane normal to the optical axis.

63. A method for illuminating an adjusted specimen using a microscope body, said method comprising:

dying the adjusted specimen with a molecule which has three electron states including at least a ground state;

providing light having a wavelength $\lambda 1$ for exciting the molecule from the ground state to the first electron excited state;

providing light having a wavelength $\lambda 2$ for exciting the molecule in the first electron excited state to the second or higher electron excited state;

condensing the light having the wavelength $\lambda 1$ and the light having the wavelength $\lambda 2$ on the adjusted specimen;

partially overlapping an irradiation region of the light having the wavelength $\lambda 1$ and an irradiation region of the light having the wavelength $\lambda 2$ on the adjusted specimen; and detecting an emission upon deexcitation of the excited molecule to the ground state;

inhibiting a region of the emission, upon deexcitation of the molecule from the first electron excited state to the ground state, by irradiating the light having the wavelength $\lambda 1$ and the light having the wavelength $\lambda 2$; and wherein a beam obtained by condensing the light having the wavelength $\lambda 2$ has a phase distribution in which the phase is shifted by $\pi$ at a symmetric position with respect to an optical axis of the beam in a plane normal to the optical axis.

* * * * *